United States Patent

Lowe et al.

(10) Patent No.: US 6,498,168 B2
(45) Date of Patent: Dec. 24, 2002

(54) MUSCARINIC ANTAGONISTS

(75) Inventors: Derek Lowe, Scotch Plains, NJ (US); Wei Chang, Livingston, NJ (US); Joseph Kozlowski, Princeton, NJ (US); Joel G. Berger, Cedar Grove, NJ (US); Robert McQuade, Scotch Plains, NJ (US); Allen Barnett, Pine Brook, NJ (US); Margaret Sherlock, Bloomfield, NJ (US); Wing Tom, Cedar Grove, NJ (US); Sundeep Dugar, Bridgewater, NJ (US); Lian-Yong Chen, Edison, NJ (US); John W Clader, Cranford, NJ (US); Samuel Chackalamannil, East Brunswick, NJ (US); Wang Yuguang, North Brunswick, NJ (US); Stuart W. McCombie, Caldwell, NJ (US); Jayaram R. Tagat, Westfield, NJ (US); Susan F. Vice, Mountainside, NJ (US); Wayne Vaccaro, Yardley, PA (US); Michael J. Green, Skillman, NJ (US); Margaret E. Browne, Bloomfield, NJ (US); Theodros Asberom, West Orange, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/902,849

(22) Filed: Jul. 11, 2001

(65) Prior Publication Data

US 2002/0103205 A1 Aug. 1, 2002

Related U.S. Application Data

(60) Division of application No. 09/482,168, filed on Jan. 12, 2000, which is a division of application No. 09/195,742, filed on Nov. 19, 1998, now Pat. No. 6,037,352, which is a division of application No. 08/602,403, filed on Feb. 16, 1996, now Pat. No. 5,883,096, which is a continuation-in-part of application No. 08/457,712, filed on Jun. 2, 1995, now abandoned, which is a continuation-in-part of application No. 08/392,697, filed on Feb. 23, 1995, now abandoned.

(51) Int. Cl.[7] ................ C07D 401/02; A61K 31/445

(52) U.S. Cl. .............. 514/316; 546/186; 546/187; 546/188; 546/189

(58) Field of Search .................. 514/316; 546/186, 546/187, 188, 189

(56) References Cited

U.S. PATENT DOCUMENTS 2,819,723 A    1/1958    Drain et al. ............. 260/294.3

(List continued on next page.)

FOREIGN PATENT DOCUMENTS

DE           963424           11/1956

(List continued on next page.)

OTHER PUBLICATIONS

Baumgold, et al., European Journal of Pharmacology 251 (1994) 315–317.

(List continued on next page.)

Primary Examiner—Sabiha Qazi
(74) Attorney, Agent, or Firm—Anita W. Magatti

(57) ABSTRACT

Di-N-substituted piperazine or 1,4 di-substituted piperadine compounds in accordance with formula I (including all isomers, salts, esters, and solvates)

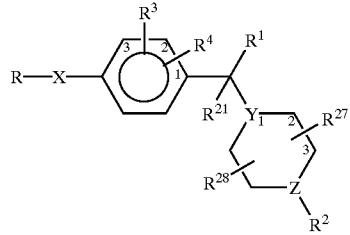

wherein R, $R^1$, $R^2$, $R^3$, $R^4$, $R^{21}$, $R_{27}$, $R^{28}$, X, Y, and Z are as defined herein are muscarinic antagonists useful for treating cognitive disorders such as Alzheimer's disease. Pharmaceutical compositions and methods of preparation are also disclosed. Also disclosed are synergistic combinations of compounds of the above formula or other compounds capable of enhancing acetylcholine release with acetylcholinesterase inhibitors.

5 Claims, 5 Drawing Sheets

U.S. PATENT DOCUMENTS

| | | | |
|---|---|---|---|
| 3,852,455 A | | 12/1974 | Carr .......................... 424/267 |
| 4,895,841 A | | 1/1990 | Sugimoto et al. ........... 514/212 |
| 5,889,006 A | | 3/1999 | Lowe et al. ................. 519/252 |
| 5,952,349 A | | 9/1999 | Asberom et al. ........... 514/316 |
| 5,977,138 A | | 11/1999 | Wang et al. ................ 514/316 |
| 6,043,255 A | * | 3/2000 | Lowe et al. ................. 514/316 |
| 6,066,636 A | * | 5/2000 | Kozlowski et al. ......... 514/252 |
| 6,288,068 B1 | * | 9/2001 | Lowe et al. ................. 514/256 |
| 6,387,930 B1 | * | 5/2002 | Baroudy et al. ............ 514/316 |
| 6,391,865 B1 | * | 5/2002 | Baroudy et al. .............. 514/63 |

FOREIGN PATENT DOCUMENTS

| | | |
|---|---|---|
| EP | 0 229 391 | 7/1987 |
| GB | 807835 | 1/1959 |
| WO | WO 91/10651 | 7/1991 |
| WO | 0121590 * | 3/2001 |

OTHER PUBLICATIONS

Melchiorre, et al., J. Med. Chem, 1993, 36, 3734–3737.

Doods, et al., Life Sciences, vol. 52, pp. 497–503 (1993).

Eberlein, et al., Trends in Pharmacol Sci Dec. 1989 pp. 50–54.

Borroni, et al., Biochem Soc. Trans, Aug. 1994, 22(3) pp. 755–758.

Logemann, et al., Brit. J. Pharmacol (1961) 17, 286–296.

Wilkerson et al, *J. Med. Chem.*, *36* (20) (1993), pp. 2899–2907.

Vidaluc et al, *J. Med. Chem.*, *37* (5) (1994), pp. 689–695.

Drukarch et al, *Eur. J. Pharmacol.*, *141* (1–2) (1987), pp. 153–157.

Provan et al, Brit. J. Pharmacol., 111(4) (1994), pp. 1103–1110.

Cheng et al, *Biochem. Pharmacol.*, *22* (1973), pp. 3099–3108.

Watson et al, *J. Pharmacol. Exp. Ther.*, *237* (1986), pp. 411–418.

Protiva et al, *Collect. Czech. Chem. Comm.*, *40*, 12 (1975), pp. 3904–3923.

*Chemical Abstracts*, *53*, abstract 9254b.

\* cited by examiner

MUSCARINIC ANTAGONISTS

CROSS REFERENCE TO RELATED APPLICATIONS

This application is a divisional of U.S. Ser. No. 09/482,168, filed Jan. 12, 2000, allowed, which is a divisional of U.S. Ser. No. 09/195,742, filed Nov. 19, 1998, now U.S. Pat. No. 6,037,352, which is a divisional of U.S. Ser. No. 08/602,403, filed Feb. 16, 1996, now U.S. Pat. No. 5,883,096, which is a continuation-in-part of U.S. Ser. No. 08/457,712, filed Jun. 2, 1995, abandoned, which is a continuation-in-part of U.S. Ser. No. 08/392,697, filed Feb. 23, 1995, abandoned.

BACKGROUND OF THE INVENTION

The present invention relates to di-N-substituted piperazines and 1,4-di-substituted piperidines useful in the treatment of cognitive disorders, pharmaceutical compositions containing the compounds, methods of treatment using the compounds, and to the use of said compounds in combination with acetylcholinesterase inhibitors.

Alzheimer's disease and other cognitive disorders have received much attention lately, yet treatments for these diseases have not been very successful. According to Melchiorre et al. (J. Med. Chem. (1993), 36, 3734–3737), compounds that selectively antagonize M2 muscarinic receptors, especially in relation to M1 muscarinic receptors, should possess activity against cognitive disorders. Baumgold et al. (Eur. J. of Pharmacol., 251, (1994) 315–317) disclose 3-α-chloroimperialine as a highly selective m2 muscarinic antagonist.

The present invention is predicated on the discovery of a class of di-N-substituted piperazines and 1,4-di-substituted piperidines, some of which have m2 selectivity even higher than that of 3-α-chloroimperialine. Logemann et al (Brit. J. Pharmacol. (1961), 17, 286–296) describe certain di-N-substituted piperazines, but these are different from the inventive compounds of the present invention. Furthermore, the compounds of Logemann et al. are not disclosed to have activity against cognitive disorders.

SUMMARY OF THE INVENTION

The present invention relates to compounds according to the structural formula 1,

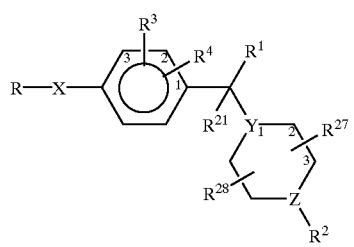

I including all isomers and pharmaceutically acceptable salts, esters, and solvates thereof,
wherein
one of Y and Z is N and the other is N, CH, or C-alkyl;
X is —O—, —S—, —SO—, —$SO_2$—, —$NR^6$—, —CO—, —$CH_2$—, —CS—, —$C(OR^5)_2$—, —$C(SR^5)_2$—, —$CONR^{20}$—, —$C(alkyl)_2$—, —C(H)(alkyl)—, —$NR^{20}$—$SO_2$—, —$NR^{20}CO$—,

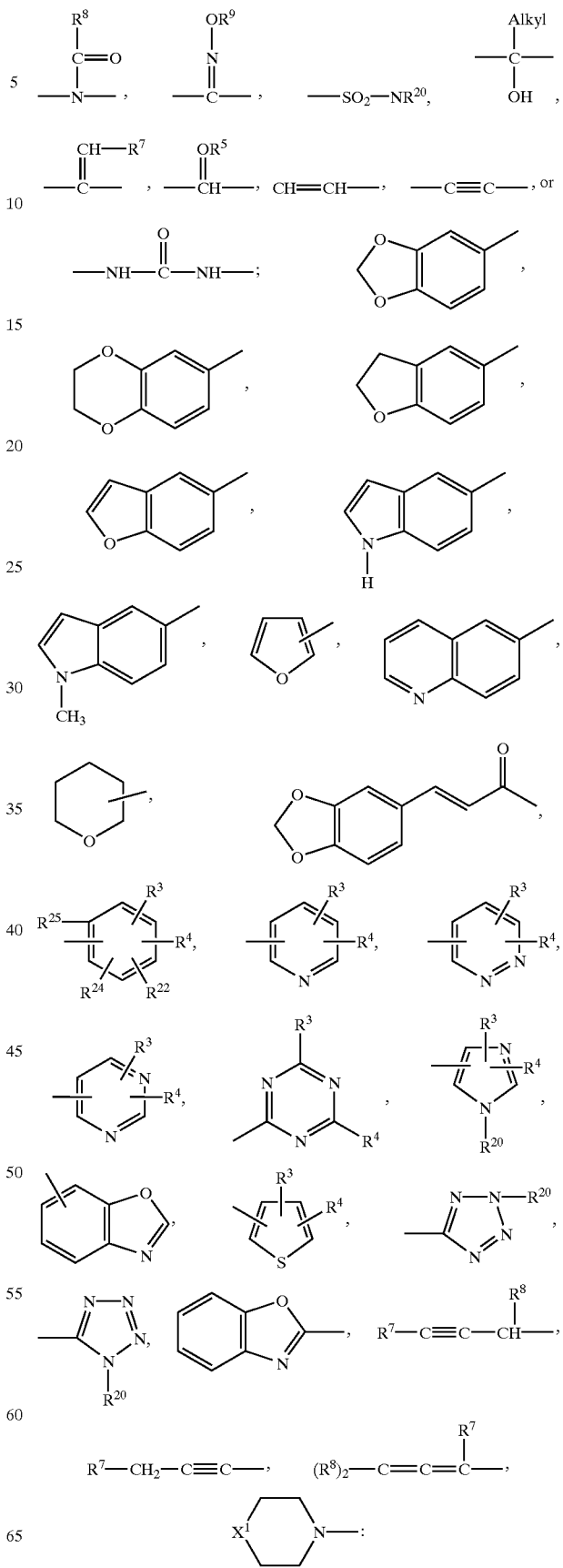

(wherein $X^1$ is —$CH_2$—, —O—, or —$NR^7$—),

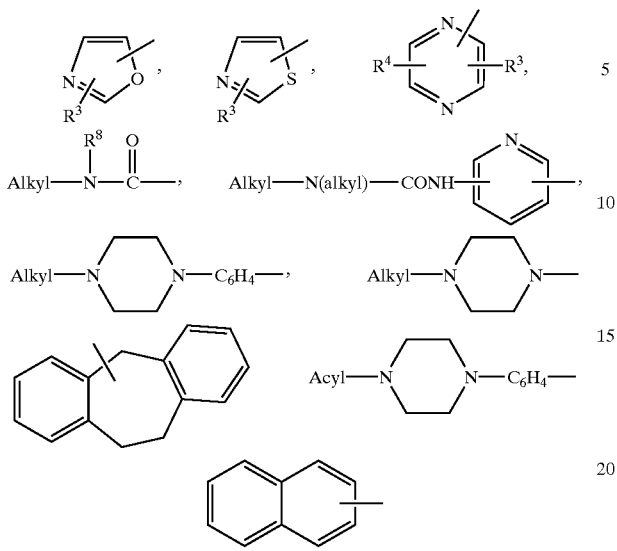

hydrogen, acyl, alkyl, alkenyl, cycloalkyl, cycloalkyl substituted with up to two alkyl groups, cycloalkenyl, bicycloalkyl, arylalkenyl, benzyl, benzyl substituted with up to three independently selected $R^3$ groups, cycloalkylalkyl, polyhaloacyl, benzyloxyalkyl, hydroxy$C_2$-$C_{20}$alkyl, alkenylcarbonyl, alkylarylsulfonyl, alkoxycarbonylaminoacyl, alkylsulfonyl, or arylsulfonyl, additionally, when X is —$CH_2$—, R may also be —OH; in further addition, when X is not N, R may also be hydroxymethyl, in further addition, R and X may combine to form the group Prot-(NOAA)$_r$—NH— wherein r is an integer of 1 to 4, Prot is a nitrogen protecting group and when r is 1, NOAA is a naturally occuring amino acid or an enantiomer thereof, or when r is 2 to 4, each NOAA is a peptide of an independently selected naturally occuring amino acid or an enantiomer thereof;

$R^1$ and $R^{21}$ are independently selected from the group consisting of alkyl, alkenyl, cycloalkyl, cycloalkenyl, bicycloalkyl, alkynyl, cyano, aminoalkyl, alkoxycarbonyl, aminocarbonyl, hydroxyguanidino, alkoxycarbonylalkyl, phenyl alkyl, alkylcarbonlyoxyalkyl,

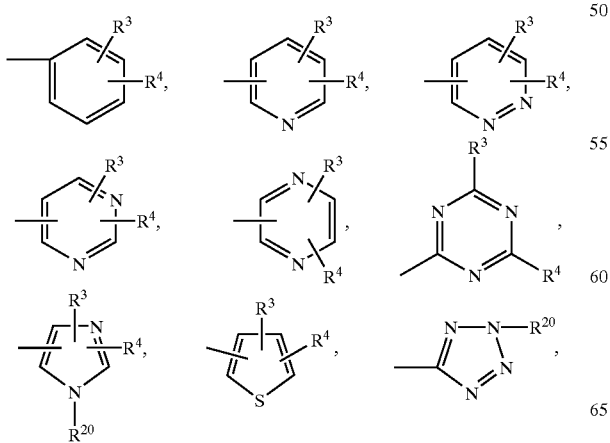

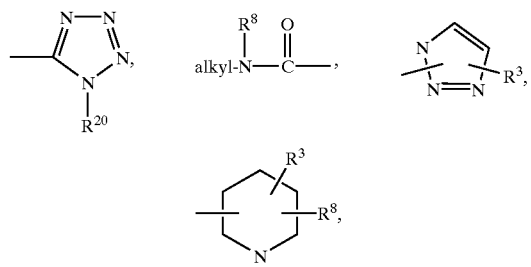

H, —OH, (provided $R^1$ and $R^{21}$ are both not —OH and Y is not N), formyl, —CO alkyl, —COacyl, —COaryl, and hydroxyalkyl; additionally $R^1$ and $R^{21}$ together may form the group

=$CH_2$, =N—$OR^5$, =N—CN, =N—$N(R^5)_2$,

=CH—Alkyl, alkylene, =O, =C(Alkyl)—Alkyl, =C(halo)$_2$, in further addition, $R^1$ and $R^{21}$ together with the carbon atom to which they are attached may form the group

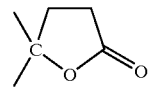

or $R^1$ and $R^{21}$ together with the carbon atom to which they are attached may form a saturated heterocyclic ring containing 3 to 7 carbon atoms and one group selected from S, O, and NH;

$R^2$ is H, alkyl, alkenyl, cycloalkyl, cycloalkyl substituted with 1 to 3 independently selected $R^3$ groups, cycloalkenyl, hydroxy$C_2$-$C_{20}$alkyl, alkynyl, alkylamide, cycloalkylalkyl, hydroxyarylalkyl, bicycloalkyl, alkynyl, acylaminoalkyl, arylalkyl, hydroxyalkoxyalkyl, azabicyclo, alkylcarbonyl, alkoxyalkyl, aminocarbonylalkyl, alkoxycarbonylaminoalkyl, alkoxycarbonylamino(alkyl)alkyl; alkylcarbonyloxyalkyl, arylhydroxyalkyl, alkylcarbonylamino(alkyl)alkyl, dialkylamino,

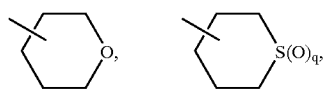

(wherein q is an integer of 0 to 2)

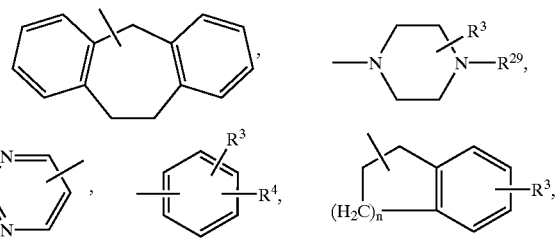

-continued wherein n is 1–3 wherein m is an integer of 4 to 7, wherein t is an integer of 3 to 5, (wherein $R^{29}$ is H, alkyl, acyl, alkoxycarbonyl, aminocarbonyl, alkylaminocarbonyl, dialkylaminocarbonyl, alkylsulfonyl, arylsulfonyl), (wherein Q is O, NOH, or NO-alkyl), or when Z is —CH—, $R^2$ may also be alkoxycarbonyl, hydroxymethyl, —N($R^8$)$_2$;

$R^3$, $R^4$, $R^{22}$, $R^{24}$, and $R^{25}$ are independently selected from the group consisting of H, halo, alkoxy, benzyloxy, benzyloxy substituted by nitro or aminoalkyl, haloalkyl, polyhaloalkyl, nitro, cyano, sulfonyl, hydroxy, amino, alkylamino, formyl, alkylthio, polyhaloalkoxy, acyloxy, trialkylsilyl, alkylsulfonyl, arylsulfonyl, acyl, alkoxycarbonyl alkylsulfinyl; —OCONH$_2$, —OCONH-alkyl, —OCON(alkyl)$_2$, —NHCOO-alkyl, —NHCO-alkyl, phenyl, hydroxyalkyl, or morpholino;

each $R^5$ and $R^6$ is independently selected from the group consisting of H and alkyl, provided that when X is C(OR$^5$)$_2$ or C(SR$^5$)$_2$, both $R^5$ groups cannot be H, and in addition, when X is C(OR$^5$)$_2$ or C(SR$^5$)$_2$, the two $R^5$ groups in X may be joined to form —(CH$_2$)$_p$— wherein p is an integer of 2 to 4:

$R^7$ is independently selected from the group consisting of H, alkyl, arylalkyl, cycloalkyl, aryl and aryl substituted with $R^3$ and $R^4$ as defined herein;

each $R^8$ is independently selected from the group consisting of H, hydroxyalkyl, or alkyl or two $R^8$ groups may be joined to form an alkylene group;

$R^9$ is H, alkyl, or acyl:

$R^{20}$ is H, phenyl or alkyl; and $R^{27}$ and $R^{28}$ are independently selected from the group consisting of H, alkyl, hydroxyalkyl, arylalkyl, aminoalkyl, haloalkyl, thioalkyl, alkylthioalkyl, carboxyalkyl, imidazolylalkyl, and indolylalkyl, additionally $R^{27}$ and $R^{28}$ may combine to form an alkylene group.

In a preferred group of compounds Y and Z are N

In another preferred group of compounds Y is CH and Z is N

In another preferred group of compounds R is and X is O, SO or SO$_2$.

In another preferred group of compounds $R^3$ and $R^4$ are H and either $R^1$ is cycloalkyl, alkyl, or CN and $R^{21}$ is H or $R^1$ and $R^{21}$ together form =CH$_2$ or =O.

In another preferred group of compounds R is

X is O, SO or SO$_2$, $R^3$ and $R^4$ are H and either $R^1$ is cycloalkyl, alkyl, or CN and $R^{21}$ is H or $R^1$ and $R^{21}$ together form =CH$_2$ or =O.

In another preferred group of compounds Y and Z are N, $R^1$ is cycloalkyl, alkyl or CN, $R^{21}$ is H and $R^2$ is cycloalkyl or In another preferred group of compounds Y is CH, Z is N, and $R^2$ is cycloalkyl or In another preferred group of compounds at least one of $R^{27}$ and $R^{28}$ is alkyl.

In another preferred group of compound one of $R^{27}$ or $R^{28}$ is methyl and the other is hydrogen.

In another preferred group of compounds R is

Another preferred group of compounds is the group represented by the formula wherein R, X, $R^1$, $R^{27}$, and $R^{21}$ are as defined in the following table

| # from table of compounds | R | X | R$^1$ | R$^{21}$ | R$^{27}$ |
|---|---|---|---|---|---|
| 169 | 4(CH$_3$O)—C$_6$H$_4$ | SO iso A | CN | H | H |
| 227(−) | 2-pyrimidinyl | O | cyclohexyl | H | H |
| 289 | 4(CH$_3$O)—C$_6$H$_4$ | SO | CN | CH$_3$ | H |
| 269 | 2-pyrimidinyl | O | CH$_3$ | H | CH$_3$ |
| 214 | 4(CH$_3$O)—C$_6$H$_4$ | SO$_2$ | CO$_2$CH$_3$ | H | H |
| 232 | 2-pyrimidinyl | O | i-propyl | H | H |
| 123 | 4(CH$_3$O)—C$_6$H$_4$ | SO | CH$_3$ | H | H |
| 236 | 4(CH$_3$O)—C$_6$H$_4$ | SO | 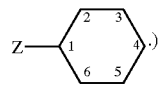 | H | H |
| 296 | 4-(CH$_3$O)—C$_6$H$_4$ | SO | CH$_3$ | CO$_2$Me | H | or having the structural formula

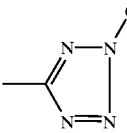

Another group of preferred compounds of formula I are: (in the table that follows, when R$^2$ is substituted cyclohexyl, the substituent positions are numbered as follows:

| compound # | 600 | 601 | 602 | 603 | 604 |
|---|---|---|---|---|---|
| R | phenyl | CH$_3$ | 4-(CH$_3$O)—C$_6$H$_4$ | 4-(CH$_3$O)—C$_6$H$_4$ | 4-(CH$_3$O)—C$_6$H$_4$ |
| R$^1$ | CH$_3$ | CH$_3$ | CH$_3$ | CH$_3$ | COOCH$_3$ |
| R$^2$ | cyclohexyl (chex) | chex | chex | chex | chex |
| R$^3$ | H | H | 2-Cl | H | H |
| R$^4$ | H | H | H | H | H |
| R$^{21}$ | CH$_3$ | H | H | H | H |
| R$^{27}$ | H | H | H | H | H |
| R$^{28}$ | H | H | H | H | H |
| X | dioxolane | —NHCNH— (C=O) | SO | SO | SO |
| Y | N | N | N | CH | N |
| Z | N | N | N | N | N |

-continued

| comp. no. | 605 | 606 | 607 | 608 | 609 | 610 | 611 |
|---|---|---|---|---|---|---|---|
| R | 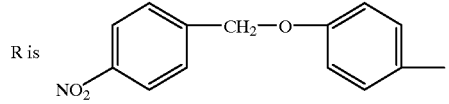 | | | 4-(CH$_3$O)—C$_6$H$_4$ | 4-(CH$_3$O)—C$_6$H$_4$ | *see below | 4-(CH$_3$O)—C$_6$H$_4$ |
| R$^1$ | chex | CH$_3$ | CN | CN | CN | CN | CN |
| R$^2$ | chex | chex | chex | chex | chex | chex | chex |
| R$^3$ | H | H | H | H | H | H | H |
| R$^4$ | H | H | H | H | H | H | H |
| R$^{21}$ | H | H | H | H | CH$_3$ | H | CH$_3$ |
| R$^{27}$ | H | H | H | H | H | H | H |
| R$^{28}$ | H | H | H | H | H | H | H |
| X | S | SO$_2$ | SO | SO$_2$ | SO | S | SO$_2$ |
| Y | N | N | N | CH | N | N | CH |
| Z | N | N | N | N | N | N | N |

*610. R is 4-nitrobenzyl 4-methylphenyl ether (O$_2$N—C$_6$H$_4$—CH$_2$—O—C$_6$H$_4$—CH$_3$)

| comp. no. | 612 | 613 | 614 | 615 | 616 | 617 |
|---|---|---|---|---|---|---|
| R | 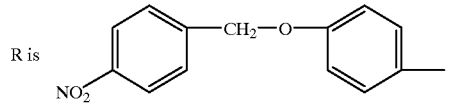 | 4-(CH$_3$O)—C$_6$H$_4$ | 4-(CH$_3$O)—C$_6$H$_4$ | 4-(CH$_3$O)—C$_6$H$_4$ | C$_6$H$_5$ | *see below |
| R$^1$ | CH$_3$ | CN | CN | CN | CN | CN |
| R$^2$ | chex | chex | chex | chex | chex | chex |
| R$^3$ | H | H | H | H | H | H |
| R$^4$ | H | H | H | H | H | H |
| R$^{21}$ | H | H | H | CH$_3$ | H | H |
| R$^{27}$ | H | (S)-3-CH$_3$ | H | H | H | H |
| R$^{28}$ | H | H | H | H | H | H |
| X | SO$_2$ | SO | SO | SO | —CH(OH)— | SO |
| Y | N | N | CH | N | N | N |
| Z | N | N | N | N | N | N |

*617. R is 4-nitrobenzyl 4-methylphenyl ether (O$_2$N—C$_6$H$_4$—CH$_2$—O—C$_6$H$_4$—CH$_3$)

| comp. no. | 618 | 619 | 620 | 621 | 622 | 623 |
|---|---|---|---|---|---|---|
| R | C$_6$H$_5$ | *see below | 2-(CH$_3$O)—C$_6$H$_4$ | 4-(CH$_3$O)—C$_6$H$_4$ | 4-(CH$_3$O)—C$_6$H$_4$ | 2-pyrimidinyl |
| R$^1$ | CH$_3$ | CH$_3$ | CN | 1-methyl-1,2,4-triazol-3-yl (CH$_3$-N-N=N with methyl) | CN | (R)-CH$_3$ |
| R$^2$ | chex | chex | chex | chex | chex | chex |
| R$^3$ | H | H | H | H | H | H |
| R$^4$ | H | H | H | H | H | H |
| R$^{21}$ | CH$_3$ | H | H | H | H | H |

-continued

| | | | | | | |
|---|---|---|---|---|---|---|
| R²⁷ | H | H | H | H | (R)-2-CH₃ | 2-CH₃ |
| R²⁸ | H | H | H | H | H | H |
| X | O | SO₂ | O | SO | SO₂ | O |
| Y | N | N | N | N | N | N |
| Z | N | N | N | N | N | N |

*619.

R is 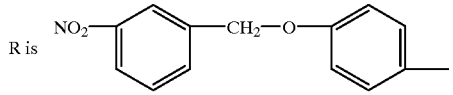

| comp. no. | 624 | 625 | 626 | 627 | 628 | 629 |
|---|---|---|---|---|---|---|
| R | *see below | 4-(CH₃O)—C₆H₄ | *see below | *see below | 4-(CH₃O)—C₆H₄ | (2-methylpyrimidinyl) |
| R¹ | CN | —CN | CN | CN | CN | CH₃ |
| R² | chex | (N-methylpiperidinyl) | chex | chex | chex | chex |
| R³ | H | H | H | H | H | H |
| R⁴ | H | H | H | H | H | H |
| R²¹ | H | H | H | H | H | H |
| R²⁷ | H | H | H | H | (R)-2-CH₃ | (R)-2-CH₃ |
| R²⁸ | H | H | H | H | H | H |
| X | S | S | S | SO | SO | O |
| Y | N | N | N | N | N | N |
| Z | N | CH | N | N | N | N |

*624.

R is 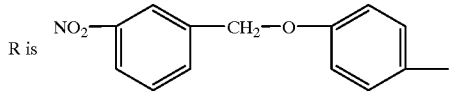

626 and 627

R is (4-aminobenzyl-O-p-tolyl)

| comp. no. | 630 | 631 | 632 | 633 | 634 | 635 |
|---|---|---|---|---|---|---|
| R | *see below | *see below | 4-(CH₃O)—C₆H₄ | 4-(CH₃O)—C₆H₄ | 4-(CH₃O)—C₆H₄ | 4-(CH₃O)—C₆H₄ |
| R¹ | CN | CN | with R²¹ forms = O | CN | CN | (1-methyl-5-tetrazolyl CH₃) |
| R² | chex | chex | chex | (N-methylpiperidinyl) | chex | chex |
| R³ | H | H | H | H | H | H |
| R⁴ | H | H | H | H | H | H |
| R²¹ | H | H | — | H | H | H |
| R²⁷ | H | H | H | H | (R)-2-CH₃ | H |
| R²⁸ | H | H | H | H | H | H |
| X | SO | SO | S | SO | S | SO |

-continued

| Y | N | N | CH | N | N | N |
| Z | N | N | N | CH | N | N |

*630.

R is [3-NO2-C6H4-CH2-O-C6H4-4-] (3-nitrobenzyl 4-methylphenyl ether group)

*631.

R is [C6H5-CH2-O-C6H4-4-] (benzyl 4-methylphenyl ether group)

| comp. no. | 636 | 637 | 638 | 639 | 640 | 641 |
|---|---|---|---|---|---|---|
| R | 2-methylpyrimidinyl | C6H5-CH3 (tolyl) | 4-(CH$_3$O)—C$_6$H$_4$ | chex | 4-(HO)—C$_6$H$_4$ | 4-(CH$_3$O)—C$_6$H$_4$ |
| R$^1$ | with R$^{21}$ forms = O | CN | with R$^{21}$ forms = O | CN | CN | with R$^{21}$ forms = N—OCH$_3$ |
| R$^2$ | chex | chex | chex | chex | chex | chex |
| R$^3$ | H | H | H | H | H | H |
| R$^4$ | H | H | H | H | H | H |
| R$^{21}$ | — | H | — | H | H | — |
| R$^{27}$ | H | (R)-2-CH$_3$ | H | H | H | H |
| R$^{28}$ | H | H | H | H | H | H |
| X | S | SO$_2$ | SO$_2$ | SO$_2$ | S | SO |
| Y | CH | N | CH | N | N | CH |
| Z | N | N | N | N | N | N |

| comp. no. | 642 | 643 | 644 | 645 | 646 | 647 |
|---|---|---|---|---|---|---|
| R | C$_6$H$_5$ | 4-(CH$_3$O)—C$_6$H$_4$ | 4-(CH$_3$O)—C$_6$H$_4$ | chex | 4-(CH$_3$O)—C$_6$H$_4$ | 4-(CH$_3$O)—C$_6$H$_4$ |
| R$^1$ | (S)-CH$_3$ | CN | CN | CN | with R$^{21}$ forms = O | with R$^{21}$ forms = N—OCH$_3$ |
| R$^2$ | chex | chex | chex | chex | chex | chex |
| R$^3$ | H | H | H | H | H | H |
| R$^4$ | H | H | H | H | H | H |
| R$^{21}$ | H | H | H | H | — | — |
| R$^{27}$ | (R)-2-CH$_3$ | (S)-2-CH$_3$ | H | H | H | H |
| R$^{28}$ | H | H | H | H | H | H |
| X | SO$_2$ | SO$_2$ | C=O | SO | SO | SO |
| Y | N | N | CH | N | CH | CH |
| Z | N | N | N | N | N | N |

| comp. no. | 648 | 649 | 650 | 651 | 652 | 653 |
|---|---|---|---|---|---|---|
| R | C$_6$H$_5$ | chex | 4-(CH$_3$O)—C$_6$H$_4$ | C$_6$H$_5$ | 4-(CH$_3$O)—C$_6$H$_4$ | 4-(CH$_3$O)—C$_6$H$_4$ |
| R$^1$ | (R)-CH$_3$ | CN | CN | with R$^{21}$ forms = O | with R$^{21}$ forms = O | CH$_3$ |
| R$^2$ | chex | chex | chex | chex | chex | chex |
| R$^3$ | H | H | H | H | H | H |
| R$^4$ | H | H | H | H | H | H |
| R$^{21}$ | H | H | H | — | — | — |
| R$^{27}$ | (R)-2-CH$_3$ | H | (R)-2-CH$_3$ | H | H | (R)-2-CH$_3$ |
| R$^{28}$ | H | H | H | H | H | H |
| X | SO$_2$ | S | SO | S | SO | S |
| Y | N | N | N | CH | CH | N |
| Z | N | N | N | N | N | N |

| comp. no. | 654 | 655 | 656 | 657 | 658 | 659 |
|---|---|---|---|---|---|---|
| R | C$_6$H$_5$ | 4-(CH$_3$O)—C$_6$H$_4$ | 4-(CH$_3$O)—C$_6$H$_4$ | 4-(CH$_3$O)—C$_6$H$_4$ | 4-(CH$_3$O)—C$_6$H$_4$ | 4-(F)-C$_6$H$_4$ |
| R$^1$ | with R$^{21}$ forms = CH$_2$ | CN | (R)-CH$_3$ | with R$^{21}$ forms =C(CH$_3$)$_2$ | CN | with R$^{21}$ forms = CH$_2$ |
| R$^2$ | chex | chex | chex | chex | N-methylpiperidinyl | chex |

-continued

| R³ | H | H | H | H | H | H |
|---|---|---|---|---|---|---|
| R⁴ | H | H | H | H | H | H |
| R²¹ | — | CH₃ | H | — | H | — |
| R²⁷ | H | H | (R)-2-CH₃ | H | H | H |
| R²⁸ | H | H | H | H | H | H |
| X | SO | SO | SO₂ | SO | SO | SO |
| Y | CH | CH | N | CH | N | CH |
| Z | N | N | N | N | CH | N |

| comp. no. | 660 | 661 | 662 | 663 | 664 | 665 |
|---|---|---|---|---|---|---|
| R | C₆H₅ | 4-(CH₃O)—C₆H₄ | 4-(F)-C₆H₄ | 4-(CH₃O)—C₆H₄ | 4-(CH₃O)—C₆H₄ | 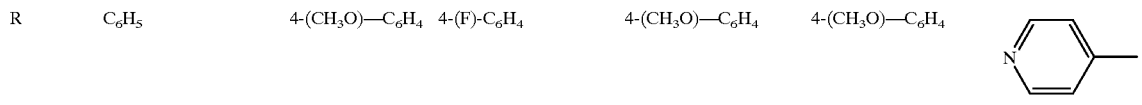 |
| R¹ | with R²¹ forms = O | —CONH₂ | with R²¹ forms = O | with R²¹ forms = CH₂ | —COOCH₃ | with R²¹ forms = O |
| R² | chex | chex | chex | chex | 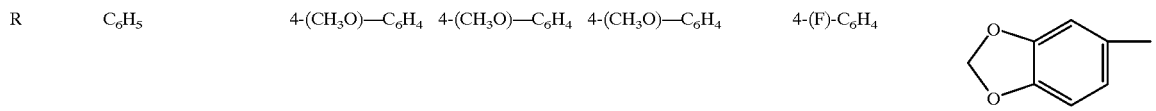 | chex |
| R³ | H | H | H | H | H | H |
| R⁴ | H | H | H | H | H | H |
| R²¹ | — | H | — | — | H | — |
| R²⁷ | H | H | H | H | H | H |
| R²⁸ | H | H | H | H | H | H |
| X | SO₂ | SO | SO₂ | SO₂ | SO | S |
| Y | CH | CH | CH | CH | N | CH |
| Z | N | N | N | N | CH | N |

| comp. no. | 666 | 667 | 668 | 669 | 670 | 671 |
|---|---|---|---|---|---|---|
| R | C₆H₅ | 4-(CH₃O)—C₆H₄ | 4-(CH₃O)—C₆H₄ | 4-(CH₃O)—C₆H₄ | 4-(F)-C₆H₄ | 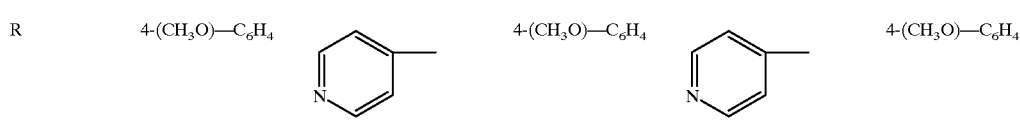 |
| R¹ | with R²¹ forms = CH₂ | (S)-CH₃ | —COOCH₃ | with R²¹ forms = N—OH | with R²¹ forms = O | with R²¹ forms = O |
| R² | chex | chex | chex | chex | chex | chex |
| R³ | H | H | H | H | H | H |
| R⁴ | H | H | H | H | H | H |
| R²¹ | — | H | H | — | — | — |
| R²⁷ | H | (R)-2-CH₃ | H | H | H | H |
| R²⁸ | H | H | H | H | H | H |
| X | SO₂ | SO₂ | SO | SO | SO | SO |
| Y | CH | N | CH | CH | CH | CH |
| Z | N | N | N | N | N | N |

| comp. no. | 672 | 673 | 674 | 675 | 676 |
|---|---|---|---|---|---|
| R | 4-(CH₃O)—C₆H₄ |  | 4-(CH₃O)—C₆H₄ |  | 4-(CH₃O)—C₆H₄ |
| R¹ | —CF₃ | with R²¹ forms = CH₂ | see note | with R²¹ forms = CH₂ | with R²¹ forms = CH₂ |
| R² | chex | chex | chex | chex |  |
| R³ | H | H | H | H | H |
| R⁴ | H | H | H | H | H |
| R²¹ | H | — | — | — | — |
| R²⁷ | H | H | H | H | H |
| R²⁸ | H | H | H | H | H |
| X | SO | S | SO | SO | SO |

-continued

| Y | N | CH | CH | CH | CH |
|---|---|---|---|---|---|
| Z | N | N | N | N | N |

674. R¹ and R²¹ together with the carbon atom to which they are attached form 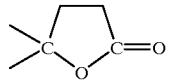

| comp. no. | 677 | 678 | 679 | 680 | 681 | 682 |
|---|---|---|---|---|---|---|
| R | 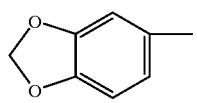 | 4-(CH₃O)—C₆H₄ | 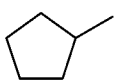 | 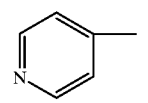 | 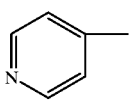 | 4-(CH₃O)—C₆H₄ |
| R¹ | with R²¹ forms = NOCH₃ Isomer A | F₃C— | with R²¹ forms = O | with R²¹ forms = O | with R²¹ forms = CH₂ | with R²¹ forms = CH₂ |
| R² | chex | chex | chex | chex | chex | 4(C₆H₅)chex |
| R³ | H | H | H | H | H | H |
| R⁴ | H | H | H | H | H | H |
| R²¹ | — | H | — | — | — | — |
| R²⁷ | H | H | H | H | H | H |
| R²⁸ | H | H | H | H | H | H |
| X | SO Isomer 1 | SO₂ | SO | SO₂ | SO₂ | SO |
| Y | CH | N | CH | CH | CH | CH |
| Z | N | N | N | N | N | N |

| comp. no. | 683 | 684 | 685 | 686 | 687 |
|---|---|---|---|---|---|
| R | 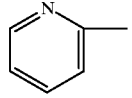 | 4(F)C₆H₄ | 4-(CH₃O)—C₆H₄ | 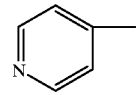 | 4-(CF₃)—C₆H₄ |
| R¹ | with R²¹ forms = O | with R²¹ forms = CH₂ | with R²¹ forms = CH₂ | with R²¹ forms = O | with R²¹ forms = CH₂ |
| R² | chex | chex | 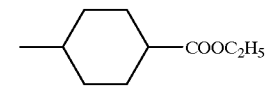 | chex | chex |
| R³ | H | H | H | H | H |
| R⁴ | H | H | H | H | H |
| R²¹ | — | — | — | — | — |
| R²⁷ | H | H | H | H | H |
| R²⁸ | H | H | H | H | H |
| X | S | SO₂ | S | SO | SO |
| Y | CH | CH | CH | CH | CH |
| Z | N | N | N | N | N |

| comp. no. | 688 | 689 | 690 | 691 | 692 | 693 |
|---|---|---|---|---|---|---|
| R | 4-(CH₃O)—C₆H₄ | 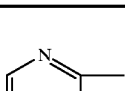 | 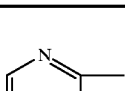 | 4-(CH₃O)—C₆H₄ | 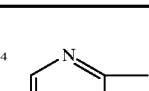 | 3-(CH₃O)—C₆H₄ |
| R¹ | with R²¹ forms = CH₂ | with R²¹ forms = O | with R²¹ forms = CH₂ | —CN | with R²¹ forms = CH₂ | with R²¹ forms = O |
| R² | 4(C₆H₅)chex | chex | chex | chex | chex | chex |
| R³ | H | H | H | H | H | H |
| R⁴ | H | H | H | H | H | H |
| R²¹ | — | — | — | H | — | — |
| R²⁷ | H | H | H | H | H | H |
| R²⁸ | H | H | H | H | H | H |
| X | SO₂ | SO₂ | S | SO | SO | SO₂ |
| Y | CH | CH | CH | CH | CH | CH |
| Z | N | N | N | N | N | N |

-continued

| comp. no. | 694 | 695 | 696 | 697 | 698 | 699 |
|---|---|---|---|---|---|---|
| R | 2-(CH$_3$O)—C$_6$H$_4$ | 4-(CH$_3$O)—C$_6$H$_5$ | 2-(CH$_3$O)—C$_6$H$_4$ | 2-methylpyridyl | 4-benzyloxy phenyl | 2-(CH$_3$O)—C$_6$H$_4$ |
| R$^1$ | with R$^{21}$ forms = O | —CH$_3$ | with R$^{21}$ forms = CH$_2$ | with R$^{21}$ forms = O | with R$^{21}$ forms = CH$_2$ | with R$^{21}$ forms = O |
| R$^2$ | chex | chex | chex | chex | chex | chex |
| R$^3$ | H | H | H | H | H | H |
| R$^4$ | H | H | H | H | H | H |
| R$^{21}$ | — | —CH$_3$ | — | — | — | — |
| R$^{27}$ | H | H | H | H | H | H |
| R$^{28}$ | H | H | H | H | H | H |
| X | SO$_2$ | SO$_2$ | O | SO | SO$_2$ | S |
| Y | CH | CH | CH | CH | CH | CH |
| Z | N | N | N | N | N | N |

| comp. no. | 700 | 701 | 702 | 703 | 704 | 705 |
|---|---|---|---|---|---|---|
| R | 4-(CH$_3$O)—C$_6$H$_4$ | 4-(CH$_3$O)—C$_6$H$_4$ | 4-(CH$_3$O)—C$_6$H$_5$ | 2-methylpyridyl | 3-(CH$_3$O)—C$_6$H$_5$ | 4-(CH$_3$O)—C$_6$H$_5$ |
| R$^1$ | with R$^{21}$ forms = O | with R$^{21}$ forms = O | —CN | with R$^{21}$ forms = CH$_2$ | with R$^{21}$ forms = O | —CH$_3$ |
| R$^2$ | chex | chex | chex | chex | chex | chex |
| R$^3$ | H | H | H | H | H | H |
| R$^4$ | H | H | H | H | H | H |
| R$^{21}$ | — | — | H | — | — | —CH$_3$ |
| R$^{27}$ | 2-(CH$_3$) | H | H | H | H | H |
| R$^{28}$ | H | H | H | H | H | H |
| X | SO$_2$ | SO$_2$—NH | SO | SO$_2$ | SO | SO |
| Y | CH | CH | CH | CH | CH | CH |
| Z | N | N | N | N | N | N |

| comp. no. | 706 | 707 | 708 | 709 | 710 |
|---|---|---|---|---|---|
| R | 4-(CH$_3$O)—C$_6$H$_5$ | 4-(CH$_3$O)—C$_6$H$_5$ | 4-(CH$_3$O)—C$_6$H$_4$ | 4-(CH$_3$O)—C$_6$H$_5$ | 3-(Cl)—C$_6$H$_4$ |
| R$^1$ | with R$^{21}$ forms = CH$_2$ | (S)-C$_2$H$_5$ | (R)-C$_2$H$_5$ | with R$^{21}$ forms = O | CH$_3$ |
| R$^2$ | chex | chex | chex | chex | 4-(N-COOC$_2$H$_5$)-piperidyl |
| R$^3$ | H | H | H | H | H |
| R$^4$ | H | H | H | H | H |
| R$^{21}$ | — | H | H | — | H |
| R$^{27}$ | 2(CH$_3$) | (R)-2-(CH$_3$) | (R)-2-(CH$_3$) | H | H |
| R$^{28}$ | H | H | H | H | H |
| X | SO$_2$ | SO$_2$ | SO$_2$ | SO$_2$ | SO$_2$ |
| Y | CH | CH | N | CH | N |
| Z | N | N | N | N | N |

| comp. no. | 711 | 712 | 713 | 714 | 715 | 716 |
|---|---|---|---|---|---|---|
| R | 4-(CH$_3$O)—C$_6$H$_4$ | see note 712. | 4-(CH$_3$O)—C$_6$H$_4$ | 4-(CH$_3$O)—C$_6$H$_4$ | 4-(CH$_3$O)—C$_6$H$_4$ | 4-(HO)—C$_6$H$_4$ |
| R$^1$ | with R$^{21}$ forms = CH$_2$ | with R$^{21}$ forms = O | —CN | (S)-2-propyl | —CH$_3$ isomer 1 | with R$^{21}$ forms = O |
| R$^2$ | 4-(N-COOt-butyl)-piperidyl | chex | chex | chex | chex | chex |
| R$^3$ | H | H | H | H | H | H |
| R$^4$ | H | H | H | H | H | H |
| R$^{21}$ | — | — | —CH$_3$ | H | H | — |
| R$^{27}$ | H | H | H | (R)-2(CH$_3$) | (R)-2-n-C$_3$H$_7$ | H |
| R$^{28}$ | H | H | H | H | H | H |
| X | SO$_2$ | SO$_2$ | SO$_2$ | SO$_2$ | SO$_2$ | SO$_2$ |

-continued

| | | | | | | |
|---|---|---|---|---|---|---|
| Y | CH | CH | CH | N | N | CH |
| Z | N | N | N | N | N | N |

712.    R is  H₃C—N(piperazine)N—C₆H₄

| comp. no. | 717 | 718 | 719 | 720 | 721 |
|---|---|---|---|---|---|
| R | 4-(CH₃O)—C₆H₄ | 4-(CH₃O)—C₆H₄ | 4-(CH₃O)—C₆H₄ | 4-(CH₃O)—C₆H₄ | 4-(CH₃O)—C₆H₄ |
| R¹ | with R²¹ forms = CH₂ | with R²¹ forms = O | with R²¹ forms = O | (R)-2-propyl | CH₃ isomer 2 |
| R² | 4-piperidinyl-NH | chex | 4-piperidinyl-N—COOC₂H₅ | chex | chex |
| R³ | H | H | H | H | H |
| R⁴ | H | H | H | H | H |
| R²¹ | — | — | — | H | H |
| R²⁷ | H | H | H | (R)-2(CH₃) | (R)-2-n-propyl |
| R²⁸ | H | H | H | H | H |
| X | SO₂ | —CONH— | SO₂ | SO₂ | SO₂ |
| Y | CH | CH | CH | N | N |
| Z | N | N | N | N | N |

| comp. no. | 722 | 723 | 724 | 725 | 726 |
|---|---|---|---|---|---|
| R | 4-(CF₃O)—C₆H₄ | 4-(O-morpholine-N)—C₆H₄ | 4-(CH₃O)—C₆H₄ | 4-(CH₃O)—C₆H₄ | 4-(CH₃O)—C₆H₄ |
| R¹ | with R²¹ forms = O | with R²¹ forms = O | —CH₃ | with R²¹ forms = O | (S)-CH₃ |
| R² | chex | chex | chex | 4-piperidinyl-N—COOC₂H₅ | cyclopentyl |
| R³ | H | H | H | H | H |
| R⁴ | H | H | H | H | H |
| R²¹ | — | — | —CN | — | H |
| R²⁷ | H | H | H | H | (R)-2-(CH₃) |
| R²⁸ | H | H | H | H | H |
| X | SO₂ | SO₂ | SO₂ | SO | SO₂ |
| Y | CH | CH | CH | CH | N |
| Z | N | N | N | N | N |

| comp. no. | 727 | 728 | 729 | 730 | 731 | 732 | 733 |
|---|---|---|---|---|---|---|---|
| R | 4-(CH₃O)—C₆H₄ | 4-(CH₃O)—C₆H₄ | 4-(CH₃O)—C₆H₄ | 4-(CH₃O)—C₆H₄ | 4-(CH₃O)—C₆H₄ | 4-(CH₃O)—C₆H₄ | 4-(CH₃O)—C₆H₄ |
| R¹ | (S)-CH₃ | (S)-CH₃ | CH₃ | with R²¹ forms = O | (S)-CH₃ | (S)-CH₃ | (S)-CH₃ |
| R² | cycloheptyl | cyclobutyl | 1-methylpiperidinyl | chex | cyclopropyl | cyclopentyl | cyclooctyl |
| R³ | H | H | H | H | H | H | H |
| R⁴ | H | H | H | H | H | H | H |
| R²¹ | H | H | H | — | H | H | H |
| R²⁷ | 3-(CH₃) | (R)-2-(CH₃) | H | (R)-2-(CH₃) | H | 3(CH₃) | (R)-2(CH₃) |
| R²⁸ | H | H | H | H | H | H | H |
| X | SO₂ | SO₂ | SO | SO₂ | SO₂ | SO₂ | SO₂ |
| Y | N | N | N | N | N | N | N |
| Z | N | N | CH | N | N | N | N |

-continued

| comp. no. | 734 | 735 | 736 | 737 | 738 | 739 |
|---|---|---|---|---|---|---|
| R | 4-(CH$_3$O)—C$_6$H$_4$ | 4-(CH$_3$O)—C$_6$H$_4$ | 4-(CH$_3$O)—C$_6$H$_4$ | 4-(CH$_3$O)—C$_6$H$_4$ | 4-(CH$_3$O)—C$_6$H$_4$ | 4-(CH$_3$O)—C$_6$H$_4$ |
| R$^1$ | (S)-CH$_3$ | CH$_3$ | (S)-CH$_3$ | (S)-CH$_3$ | (S)-CH$_3$ | (S)-CH$_3$ |
| R$^2$ | cyclobutyl | 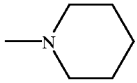 | 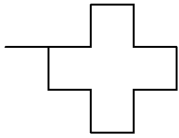 | cyclopropyl | cycloheptyl | cyclooctyl |
| R$^3$ | H | H | H | H | H | H |
| R$^4$ | H | H | H | H | H | H |
| R$^{21}$ | H | H | H | H | H | H |
| R$^{27}$ | 3(CH$_3$) | H | (R)-2(CH$_3$) | 3(CH$_3$) | (R)-2(CH$_3$) | 3(CH$_3$) |
| R$^{28}$ | H | H | H | H | H | H |
| X | SO$_2$ | SO$_2$ | SO$_2$ | SO$_2$ | SO$_2$ | SO$_2$ |
| Y | N | N | N | N | N | N |
| Z | N | CH | N | N | N | N |

| comp. no. | 740 | 741 | 742 | 743 | 744 | 745 | 746 |
|---|---|---|---|---|---|---|---|
| R | 4-(CH$_3$O)—C$_6$H$_4$ | 4-(CH$_3$O)—C$_6$H$_4$ | 44-(CH$_3$O)—C$_6$H$_4$ | See note 743 | See Note | See Note | See Note |
| R$^1$ | with R$^{21}$ forms = CH$_2$ | (S)-CH$_3$ | (S)-CH$_3$ | CH$_3$ | CH$_3$ | CH$_3$ | CN |
| R$^2$ | chex | chex | 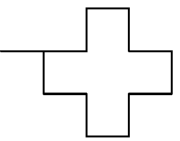 | chex | chex | chex | chex |
| R$^3$ | H | H | H | H | H | H | H |
| R$^4$ | H | H | H | H | H | H | H |
| R$^{21}$ | — | H | H | H | H | H | H |
| R$^{27}$ | with R$^{28}$ forms 3,5-(CH$_2$)$_2$— | 3-(CH$_3$) | 3-(CH$_3$) | H | H | H | H |
| R$^{28}$ | — | H | H | H | H | H | H |
| X | SO$_2$ | SO$_2$ | SO$_2$ | —CONH— | —CONH— | —CONH— | S |
| Y | CH | N | N | N | N | N | N |
| Z | N | N | N | N | N | N | N |

743. R is 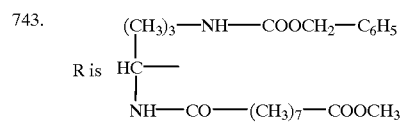

744. R is 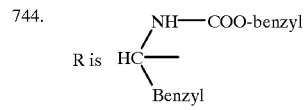

745. R is 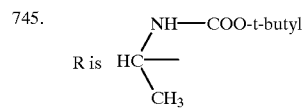

746. R is 4-[CH$_3$—N(CH$_3$)—COO]—C$_6$H$_4$

| comp. no. | 747 | 748 | 749 | 750 | 751 | 752 | 753 | 754 |
|---|---|---|---|---|---|---|---|---|
| R | See Note | 4-(CH$_3$O)—C$_6$H$_4$ | See Note | See Note | See Note | See Note | 4-(CH$_3$O)—C$_6$H$_4$ | 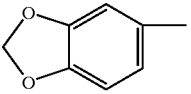 |

-continued

| R¹ | CH₃ | —OH | CH₃ | CH₃ | CH₃ | CN | 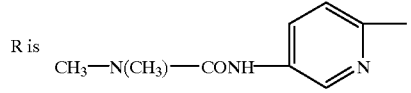 | with R²¹ forms = O |
|---|---|---|---|---|---|---|---|---|
| R² | chex | chex | chex | chex | chex | chex | chex | chex |
| R³ | H | H | H | H | H | H | H | H |
| R⁴ | H | H | H | H | H | H | H | H |
| R²¹ | H | H | H | H | H | H | H | — |
| R²⁷ | H | H | H | H | H | H | H | H |
| R²⁸ | H | H | H | H | H | H | H | H |
| X | O | SO | —CONH— | —CONH— | —CONH— | SO₂ | SO | SO |
| Y | N | CH | N | N | N | N | N | CH |
| Z | N | N | N | N | N | N | N | N |

747. R is 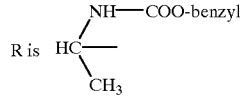

749. R is 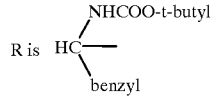

750 R is $$\text{HC} \begin{array}{c} \text{NHCOO-t-butyl} \\ | \\ \text{benzyl} \end{array}$$

751. R is 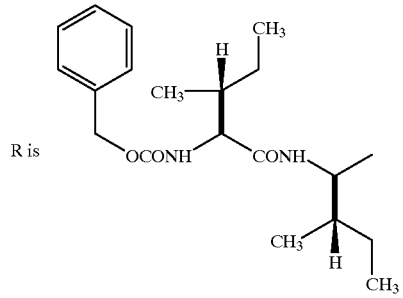

752. R is 4-[(CH₃)₂N—COO]—C₆H₄—

| comp. no. | 755 | 756 | 757 | 758 | 759 |
|---|---|---|---|---|---|
| R | 4-(CH₃O)—C₆H₄ | 4-(CH₃O)—C₆H₄ | 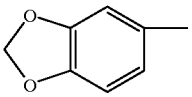 | 4-(CH₃O)—C₆H₄ | 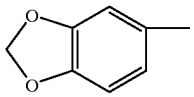 |
| R¹ | with R²¹ forms = O | OH | with R²¹ forms = O | —CH₃OH | OH |
| R² | chex | chex | chex | chex | chex |
| R³ | H | H | H | H | H |
| R⁴ | H | H | H | H | H |
| R²¹ | — | 2-propyl | — | H | CH₃ |
| R²⁷ | 1-(CH₃) | H | H | H | H |
| R²⁸ | H | H | H | H | H |
| X | SO | SO | SO | S | SO |
| Y | CH | CH | CH | CH | CH |
| Z | N | N | N | N | N |

-continued

| comp. no. | 760 | 761 | 762 | 763 | 764 |
|---|---|---|---|---|---|
| R | 4-(CH$_3$O)—C$_6$H$_4$ | 4-(CH$_3$O)—C$_6$H$_4$ | 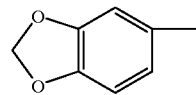 | 4-(CH$_3$O)—C$_6$H$_4$ | 4-(CH$_3$O)—C$_6$H$_4$ |
| R$^1$ | with R$^{21}$ forms = CH$_2$ | OH | with R$^{21}$ forms = CH$_2$ | with R$^{21}$ forms = CH$_2$ | —CHO |
| R$^2$ |  | chex | chex | 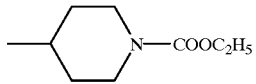 | chex |
| R$^3$ | H | H | H | H | H |
| R$^4$ | H | H | H | H | H |
| R$^{21}$ | — | ethyl | — | — | H |
| R$^{27}$ | H | H | H | H | H |
| R$^{28}$ | H | H | H | H | H |
| X | SO$_2$ | SO | SO | SO | S |
| Y | CH | CH | CH | CH | CH |
| Z | N | N | N | N | N |

| comp. no. | 765 | 766 | 767 | 768 | 769 |
|---|---|---|---|---|---|
| R | 4-(CH$_3$O)—C$_6$H$_4$ | 4-(CH$_3$O)—C$_6$H$_4$ | 4-(CH$_3$O)—C$_6$H$_4$ | 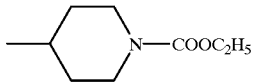 | 4-(CH$_3$O)—C$_6$H$_4$ |
| R$^1$ | with R$^{21}$ forms = CH$_2$ | —CH$_2$—OH | —CH$_2$—OH | with R$^{21}$ forms = N—OCH$_3$ Isomer B | —CH$_2$—OCO—CH$_3$ |
| R$^2$ | 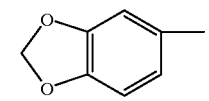 | chex | chex | chex | chex |
| R$^3$ | H | H | H | H | H |
| R$^4$ | H | H | H | H | H |
| R$^{21}$ | — | H | H | — | H |
| R$^{27}$ | H | H | H | H | H |
| R$^{28}$ | H | H | H | H | H |
| X | S | SO$_2$ | SO | SO Isomer 2 | SO |
| Y | CH | CH | CH | CH | CH |
| Z | N | N | N | N | N |

| comp. no. | 770 | 771 | 772 | 773 |
|---|---|---|---|---|
| R | 4-(CH$_3$O)—C$_6$H$_4$ | 4-(CH$_3$O)—C$_6$H$_4$ | 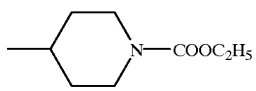 | 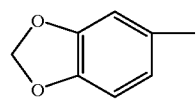 |
| R$^1$ | with R$^{21}$ forms = CF$_2$ | CH$_3$ | with R$^{21}$ forms = N—OCH$_3$ Isomer A | with R$^{21}$ forms = N—OCH$_3$ Isomer B |
| R$^2$ | chex | 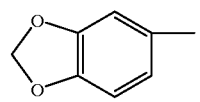 | chex | chex |
| R$^3$ | H | H | H | H |
| R$^4$ | H | H | H | H |
| R$^{21}$ | — | H | — | — |
| R$^{27}$ | H | H | H | H |
| R$^{28}$ | H | H | H | H |
| X | SO$_2$ | SO$_2$ | SO Isomer 2 | SO Isomer 1 |

-continued

| | | | | |
|---|---|---|---|---|
| Y | CH | CH | CH | CH |
| Z | N | N | N | N |

| comp. no. | 774 | 775 | 776 | 777 | 778 |
|---|---|---|---|---|---|
| R | 4-(CH$_3$O)—C$_6$H$_4$ | 4-(CH$_3$O)—C$_6$H$_4$ | 4-(CH$_3$O)—C$_6$H$_4$ | 4-(CH$_3$O)—C$_6$H$_4$ | omit |
| R$^1$ | CH$_3$—O—CO—CH$_3$ | with R$^{21}$ forms = CF$_2$ | with R$^{21}$ forms = CH$_2$ | CH$_3$ | |
| R$^2$ | chex | chex | —⌬—COOC$_2$H$_5$ | —⌬—N—SO$_2$—nC$_3$H$_7$ | |
| R$^3$ | H | H | H | H | |
| R$^4$ | H | H | H | H | |
| R$^{21}$ | H | — | — | H | |
| R$^{27}$ | H | H | H | (R)-2(CH$_3$) | |
| R$^{28}$ | H | H | H | H | |
| X | SO$_2$ | SO | SO$_2$ | SO$_2$ | |
| Y | CH | CH | CH | CH | |
| Z | N | N | N | N | |

| comp. no. | 779 | 780 | 781 | 782 | 783 |
|---|---|---|---|---|---|
| R | 4-(CH$_3$O)—C$_6$H$_4$ | 4-(CH$_3$O)—C$_6$H$_4$ | 4-(CH$_3$O)—C$_6$H$_4$ | 4-(CH$_3$O)—C$_6$H$_4$ | 4-(CH$_3$O)—C$_6$H$_4$ |
| R$^1$ | n-butyl isomer 1 | (CH$_3$)$_2$—C$_6$H$_4$ isomer 1 | with R$^{21}$ forms = CH$_2$ | with R$^{21}$ forms = CH$_2$ | (S)-CH$_3$ |
| R$^2$ | chex | chex | —⌬—O (tetrahydropyran) | —⌬—O (tetrahydropyran) | —⌬—N—COOC$_2$H$_5$ |
| R$^3$ | H | H | H | H | H |
| R$^4$ | H | H | H | H | H |
| R$^{21}$ | H | H | — | — | H |
| R$^{27}$ | (R)-2-(CH$_3$) | (R)-2-CH$_3$ | H | H | (R)-2-CH$_3$ |
| R$^{28}$ | H | H | H | H | H |
| X | SO$_2$ | SO$_2$ | SO$_2$ | S | SO$_2$ |
| Y | N | N | CH | CH | N |
| Z | N | N | N | N | N |

| comp. no. | 784 | 785 | 786 | 787 | 788 |
|---|---|---|---|---|---|
| R | 4-(CH$_3$O)—C$_6$H$_4$ | 4-(CH$_3$O)—C$_6$H$_4$ | 4-(CH$_3$O)—C$_6$H$_4$ | 4-(CH$_3$O)—C$_6$H$_4$ | 4-(CH$_3$O)—C$_6$H$_4$ |
| R$^1$ | n-butyl isomer 2 | —(CH$_2$)$_3$—C$_6$H$_5$ isomer 2 | cyclopentyl isomer 1 | with R$^{21}$ forms = CH$_2$ | (S)-CH$_3$ |
| R$^2$ | chex | chex | chex | —⌬—O (tetrahydropyran) | —⌬—N—COOC$_2$H$_5$ |
| R$^3$ | H | H | H | H | H |
| R$^4$ | H | H | H | H | H |
| R$^{21}$ | H | H | H | — | H |
| R$^{27}$ | (R)-2-CH$_3$ | (R)-2-CH$_3$ | (R)-2-CH$_3$ | H | (R)-2-CH$_3$ |
| R$^{28}$ | H | H | H | H | H |
| X | SO$_2$ | SO$_2$ | SO$_2$ | SO | SO$_2$ |
| Y | N | N | N | CH | N |
| Z | N | N | N | N | N |

| comp. no. | 789 | 790 | 791 | 792 |
|---|---|---|---|---|
| R | 4-(CH$_3$O)—C$_6$H$_4$ | 4-(CH$_3$O)—C$_6$H$_4$ | 4-(CH$_3$O)—C$_6$H$_4$ | (see note 792)- |
| R$^1$ | (S)-CH$_3$ | (R)-2-CH$_3$ | (S)-CH$_3$ | CN |
| R$^2$ | —⌬—N—COOC$_2$H$_5$ | —⌬—N—COOC$_2$H$_5$ | —⌬—N—COOnC$_3$H$_7$ | chex |
| R$^3$ | H | H | H | H |
| R$^4$ | H | H | H | H |
| R$^{21}$ | H | H | H | H |
| R$^{27}$ | (R)-2-(CH$_3$) | (R)-2-CH$_3$ | (R)-2-CH$_3$ | H |

-continued
| | | | | |
|---|---|---|---|---|
| R28 | H | H | H | H |
| X | S | S | SO2 | SO |
| Y | N | N | N | N |
| Z | N | N | N | N |
792. R is 4-[(CH3)2NCOO]—C6H4—
| comp. no. | 793 | 794 | 795 | 796 |
|---|---|---|---|---|
| R | 4-(CH3O)—C6H4 | 4-(CH3O)—C6H4 | 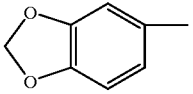 | 4-(CH3O)—C6H4 |
| R1 | (S)-CH3 | (S)-CH3 | (R)-CH3 | (S)-CH3 |
| R2 | H | 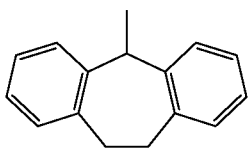 | chex | 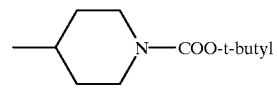 |
| R3 | H | H | H | H |
| R4 | H | H | H | H |
| R21 | H | H | H | H |
| R27 | (R)-2-CH3 | (R)-2-(CH3) | (R)-2-(CH3) | (R)-2-(CH3) |
| R28 | H | H | H | H |
| X | SO2 | SO2 | SO2 | S |
| Y | N | N | N | N |
| Z | N | N | N | N |
| comp. no. | 797 | 798 | 799 | 800 | 801 |
|---|---|---|---|---|---|
| R | 4-(CH3O)—C6H4 | 4-(CH3O)—C6H4 | 4-(CH3O)—C6H4 | 4-(CH3O)—C6H4 | 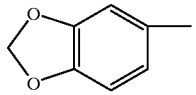 |
| R1 | (S)-CH3 | CH3 | (R)-CH3 | CH3 | (S)-CH3 |
| R2 | 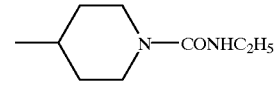 | 1-CH3-chex | 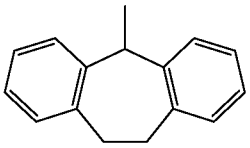 | chex | chex |
| R3 | H | H | H | H | H |
| R4 | H | H | H | H | H |
| R21 | H | H | H | CH3 | H |
| R27 | (R)-2-CH3 | H | (R)-2-CH3 | 2-CH3 | (R)-2-CH3 |
| R28 | H | H | H | H | H |
| X | SO2 | SO2 | SO2 | SO2 | SO2 |
| Y | N | N | N | CH | N |
| Z | N | N | N | N | N |
| comp. no. | 802 | 803 | 804 | 805 |
|---|---|---|---|---|
| R | 4-(CH3O)—C6H4 | 4-(CH3O)—C6H4 | 4-(CH3O)—C6H4 | 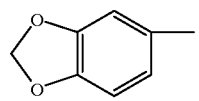 |
| R1 | CH3 | (S)-CH3 | (S)-CH3 | (S)-CH3 |

-continued

| | | | | |
|---|---|---|---|---|
| $R^2$ | chex | 4-(OH)-chex | trans 4-(OH)-chex | 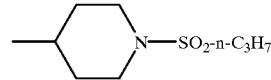 |
| $R^3$ | H | H | H | H |
| $R^4$ | H | H | H | H |
| $R^{21}$ | $CH_3$ | H | H | H |
| $R^{27}$ | 2-$CH_3$ | 3-$CH_3$ | (R)-2-($CH_3$) | (R)-2-$CH_3$ |
| $R^{28}$ | H | H | H | H |
| X | S | $SO_2$ | $SO_2$ | $SO_2$ |
| Y | CH | N | N | N |
| Z | N | N | N | N |

Another aspect of the invention is a pharmaceutical composition which comprises a compound having structural formula I as defined above in combination with a pharmaceutically acceptable carrier.

Another aspect of the invention is the use of a compound formula I for the preparation of a pharmaceutical composition useful in the treatment of cognitive disorders and neurodegenerative diseases such as Alzheimer's disease.

Yet another aspect of the invention comprises a method for making a pharmaceutical composition comprising mixing a compound of formula I with a pharmaceutically acceptable carrier.

Another aspect of this invention is a method for treating a cognitive or neurodegenerative disease comprising administering to a patient suffering from said disease an effective amount of a compound of formula I.

Another aspect of this invention is a method for treating cognitive and neurodegenerative diseases, such as Alzheimer's disease with a compound of formula I in combination with an acetylcholinesterase inhibitor.

Another aspect of this invention is a method for treating a cognitive or neurodegenerative disease comprising administering to a patient suffering from said disease an effective amount of a combination of a compound capable of enhancing acetylcholine release (preferably an m2 or m4 selective muscarinic antagonist) with an acetycholinesterase inhibitor.

Another aspect of this invention is a kit comprising in separate containers in a single package pharmaceutical compounds for use in combination to treat cognitive disorders in one container a compound of formula I or a compound capable of enhancing acetylcholine release (preferably an m2 or m4 selective muscarinic antagonist) in a pharmaceutically acceptable carrier and in a second container an acetylcholinesterase inhibitor in a pharmaceutically acceptable carrier, the combined quantities being an effective amount.

DETAILED DESCRIPTION

Figure 1:
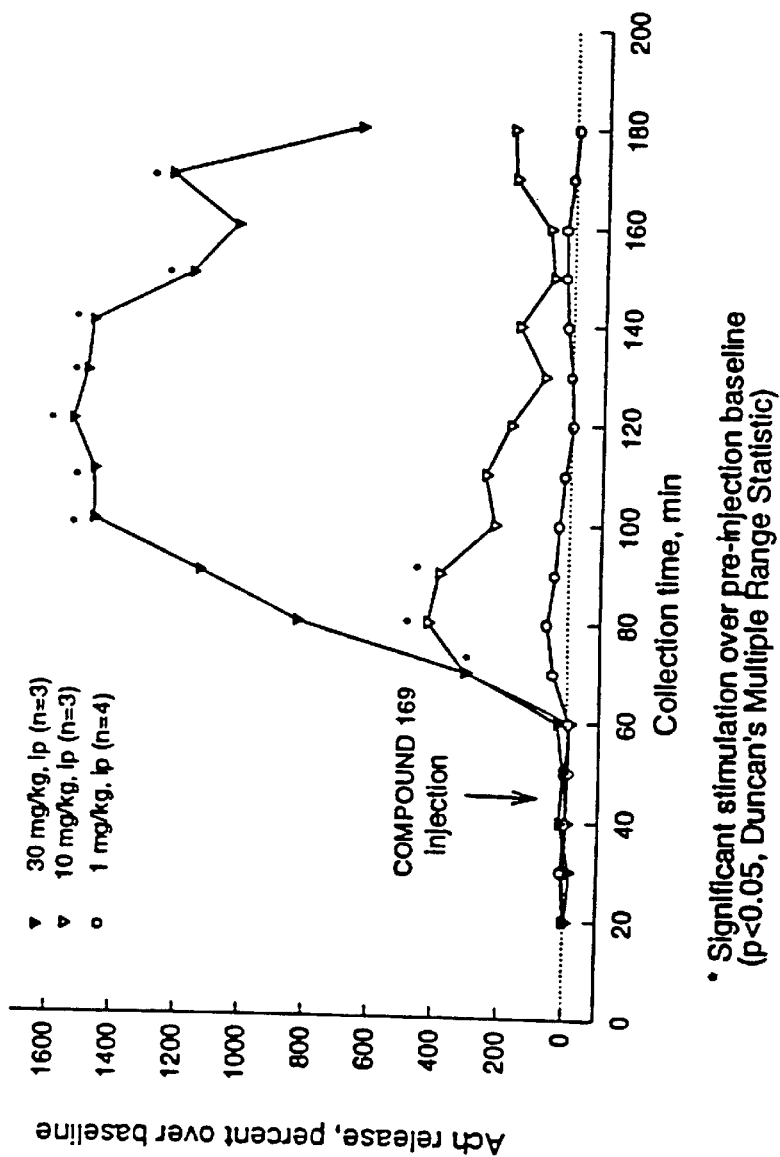
FIG. 1 illustrates the dose related effects of i.p. administration of a compound of this invention on acetylcholine (ACh) release from cortex of conscious rat.

Except where stated otherwise the following definitions apply throughout the present specification and claims. These definitions apply regardless of whether a term is used by itself or in combination with other terms. Hence the definition of "alkyl" applies to "alkyl" as well as the "alkyl" portions of "alkoxy", "haloalkyl", etc.

Alkyl represents a straight or branched saturated hydrocarbon chain having 1 to 20 carbon atoms, more preferably 1 to 8 carbon atoms.

Alkenyl represents a straight or branched hydrocarbon chain of from 2 to 15 carbon atoms, more preferably 2 to 12 carbon atoms, having at least one carbon-to-carbon double bond.

Alkynyl represents a straight or branched hydrocarbon chain of from 2 to 10 carbon atoms, more preferably 2 to 8 carbon atoms, having at least one carbon-to-carbon triple bond.

Cycloalkyl represents a saturated carbocyclic ring having 3 to 12 carbon atoms.

Cycloalkenyl represents a carbocyclic ring having from 5 to 8 carbon atoms and at least one carbon-to-carbon double bond in the ring.

Bicycloalkyl represents a saturated bridged carbocyclic ring having 5 to 12 carbon atoms.

Acyl represents a radical of the formula

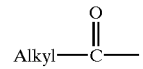

wherein alkyl is as defined previously.

Halo represents fluoro, chloro, bromo or iodo.

Aryl represents phenyl or naphthyl.

Polyhalo represent substitution of at least 2 halo atoms to the group modified by the term "polyhalo".

Hydroxyguanidino represents a group having the formula

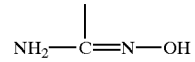

Azabicyclo represents a saturated bridged ring containing from 4 to 8 carbon atoms and at least one nitrogen atom.

Sulfonyl represents a group of the formula —$SO_2$—.

Sulfinyl represents a group of the formula —SO—.

Alkylene represents a group having the formula —$(CH_2)_q$, wherein q is an integer of from 1 to 20.

Naturally occurring amino acid (NOAA) means an acid selected from the group consisting of alanine (ala), arginine (arg), asparagine (asn), aspartic acid (asp), cysteine (cys), glutamine (gln), glutamic acid (glu), glycine (gly), histadine (his), isoleucine (ile), leucine (leu), lysine (lys), methionine (met), phenylalanine (phe), proline (pro), serine (ser), threonine (thr), tryptophan (trp), tyrosine (tyr), and valine (val).

Nitrogen protecting group (Prot) means a group capable of protecting a nitrogen on a naturally occurring amino acid (or an enantiomer thereof) from reaction. Preferred nitrogen protecting groups are carbobenzyloxy (CBZ), $CH_3OCO(CH_2)_9CO$, and t-butoxycarbonyl. Of course any operable nitrogen protecting group is included.

When a variable appears more than once in the structural formula, for example $R^5$ when X is $—C(OR^5)_2—$, the identity of each variable appearing more than once may be independently selected from the definition for that variable.

Compounds of this invention may exist in at least two stereo configurations based on the asymmetric carbon to which $R^1$ is attached, provided that $R^1$ and $R^{21}$ are not identical. Further stereoisomerism is present when X is SO, or $C(OR^5)_2$ (when the two $R^5$ groups are not the same) or when R is $—CR^5=C=CR^6,$. Also within formula I there are numerous other possibilities for stereoisomerism. All possible stereoisomers of formula I are within the scope of the invention.

Compound of formula I can exist in unsolvated as well as solvated forms, including hydrated forms. In general, the solvated forms, with pharmaceutically acceptable solvents such as water, ethanol and the like, are equivalent to the unsolvated forms for purposes of this invention.

A compound of formula I may form pharmaceutically acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

Compound in accordance with formula I may be produced by processes known to those skilled in the art as shown by the following reaction steps:

Process A (for compounds of formula I where $R^{21}$ is H and X is O, SO, or $SO_2$)

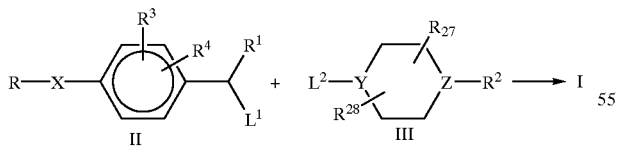

wherein $L^1$ is a leaving group and $L^2$ is H or an alkali metal and Y, Z, R, $R^1$, $R^2$, $R^3$, $R^4$, $R^{27}$ and $R^{28}$ are as defined above for formula I, and X is O, SO or $SO_2$.

Process A is preferably carried out neat or in a solvent such as DMF, DMSO, or acetonitrile, at temperatures ranging from 0° C. to 110° C. for a period of about 1–24 hours. It is preferable that $L^1$ be a chloride leaving group, but other leaving groups such as bromide, or mesylate, will suffice. It is preferable that $L^2$ be hydrogen.

Starting materials of formula II when X is O, SO, or $SO_2$ may be formed by the following reaction sequence

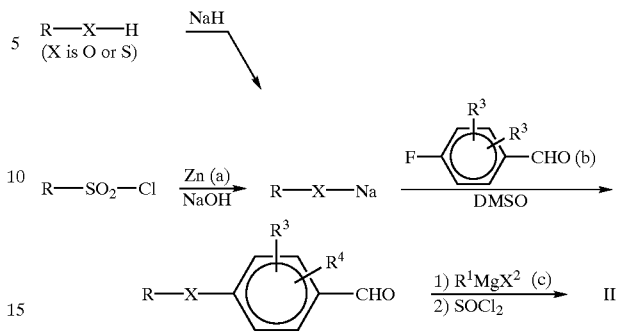

In step (a) the chloride compound is reacted with sodium hydroxide in presence of zinc in solvent such as water, at 50–95° C. for 1–3 hours. Alternatively R—X—H is reacted with NaH in solvent such as THF or DMF at 0° to room temperature for 1–3 hours. In step (b) the substituted benzaldehyde is added to the reaction mixture from step (a) and the reaction carried out for 1–24 hours at 20–70° C. In step (c) $X^2$ represents e.g. chloride or bromide. The reaction with $R^1MgX^2$ is carried out in THF or diethyl ether solvent at 0° C.–70° C. for 1–24 hours. Reaction with $SOCl_2$ is preferably done in excess thionyl chloride as solvent at 25–70° C. for 1–24 hours. Compounds of formula III are readily available. Some reaction schemes for making other compounds of formula II are shown below:

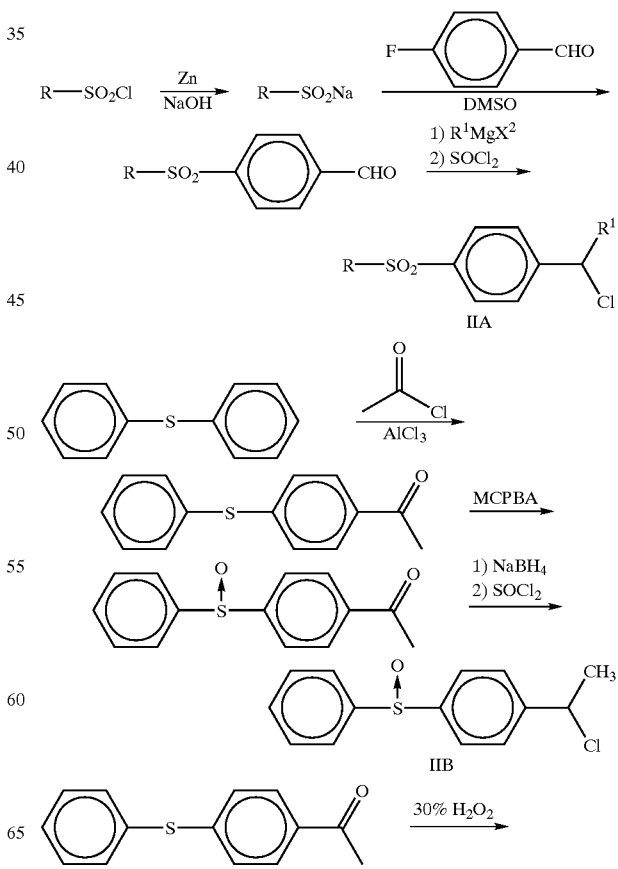

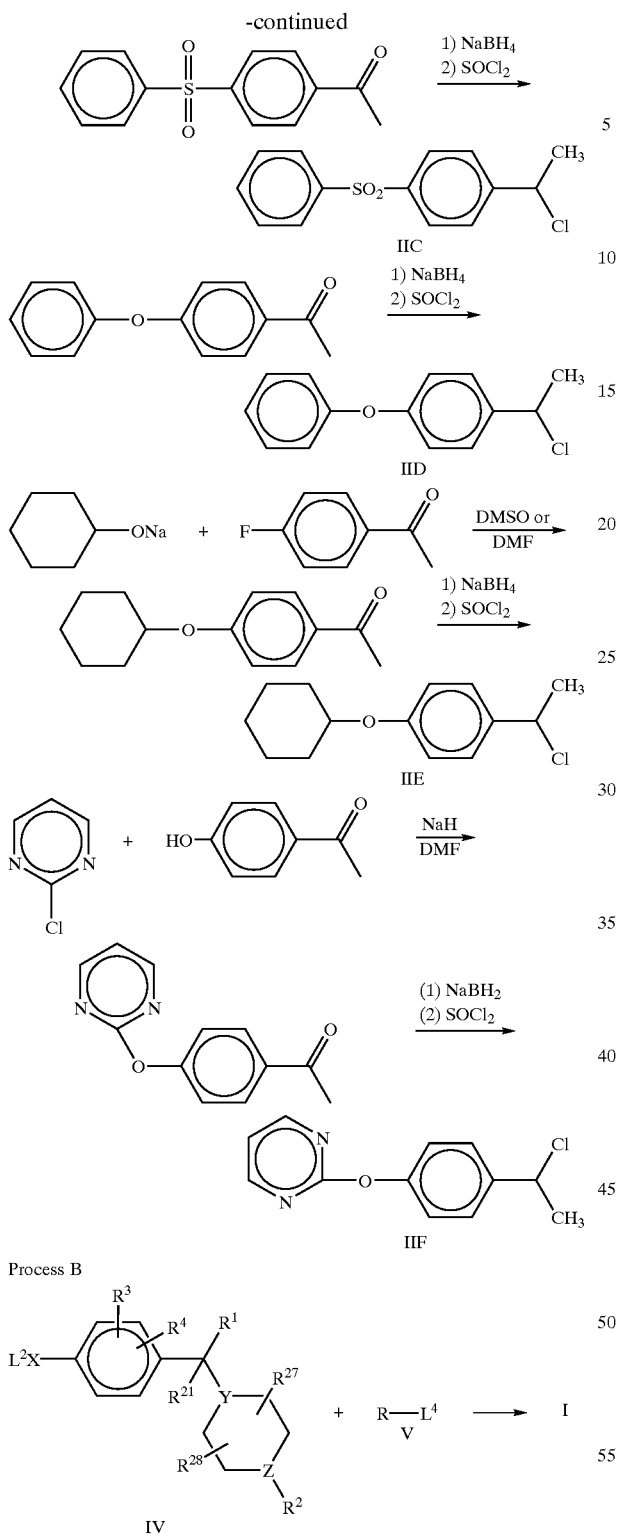

Compounds of formula IV may be produced by the following reaction scheme:

In the above reactions scheme $R^{1A}$ is preferably in accordance with the definition of $R^7$ for formula I.

Step (d) may be perfomed in acetone or DMF solvent at 20–100° C., for 1–24 hours under basic conditions, e.g. with $K_2CO_3$.

Step (e) may be performed neat or in methylene chloride, at 20–70° C., for 1–24 hours.

Step (f) may be performed in ethanol or methanol at 25–70° C. for 1–24 hours.

Process C (for compounds of formula I where $R^{21}$ is H)

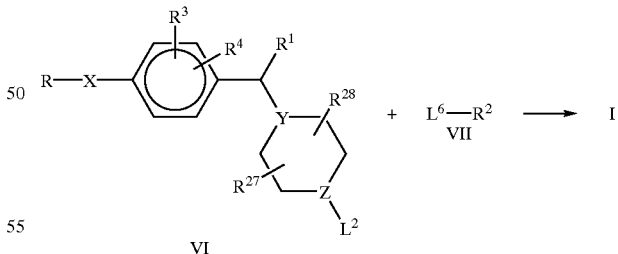

wherein $L^6$ is a leaving group and $L^2$ is H or alkali metal and X, Y, Z, R, $R^1$, $R^2$, $R^3$, $R^4$, $R^{27}$ and $R^{28}$ are as defined above for formula I.

Process C is preferably carried out in solvent such as DMF, DMSO or acetonitrile at about 0 to 110° C. for 1–24 hours. It is preferable that $L^2$ be hydrogen and that $L^6$ be a chloride leaving group.

Compounds of formula VI may be produced by the following reaction scheme:

wherein $L^4$ is a leaving group and $L^2$ is H or alkali metal and X, Y, Z, R, $R^1$, $R^2$, $R^3$, $R^4$, $R^{21}$, $R^{27}$ and $R^{28}$ are as defined above for formula I.

Process B is preferably carried out in solvent such as DMF at about 25 to 120° C. for about 1–24 hours. It is preferred that $L^2$ be Na or hydrogen and that $L^4$ be a chloride leaving group.

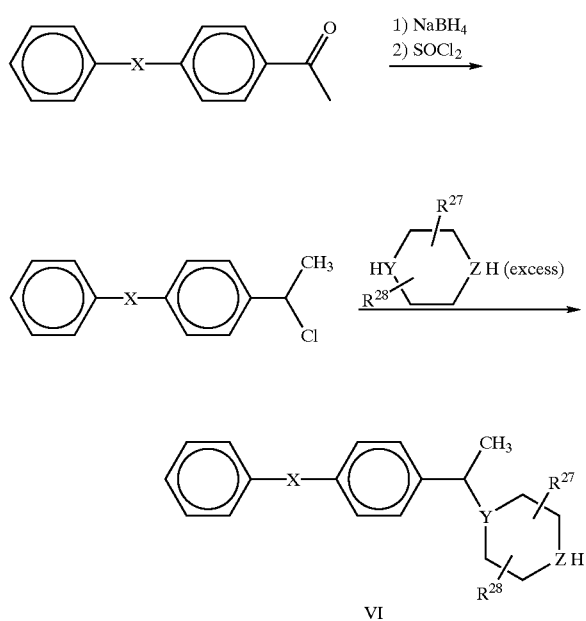

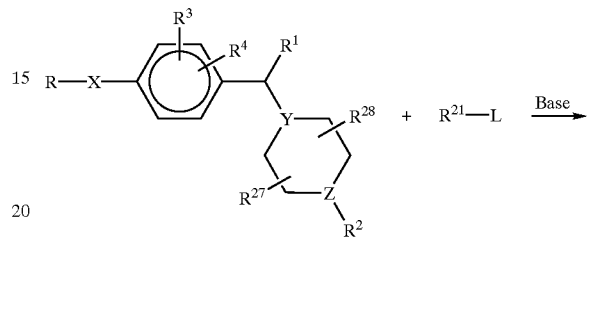

Other compounds of formula VI may be produced by similar reactions.

Process D (for compounds of formula I where $R^{21}$ is H)

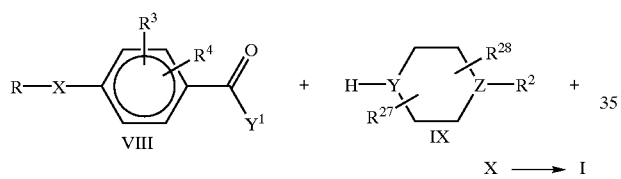

wherein $Y^1$ is H or alkyl, and compound X is $(alkyl)_2AlCN$ or a Grignard reagent.

Process D is preferably carried out by first treating a compound of formula VIII, titanium tetrachloride ($TiCl_4$) or titanium tetra isopropoxide, and a compound of formula IX neat or in solvent such as methylene chloride for about 1–24 hours at 20 to 70° C. Finally a compound of formula X is added and the mixture is stirred for 1–24 hours at 20–70° C. Compounds of formula VIII may be produced by steps (a) and (b) of process A.

Process E (for compounds wherein $R^{21}$ is not H)

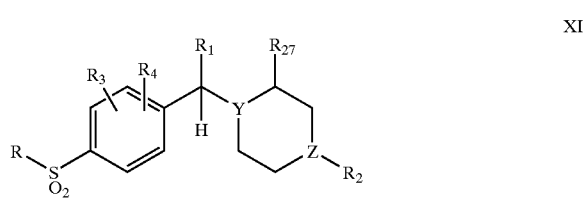

In the above reaction L is a leaving group. The reaction is performed in solvent, e.g. THF, at −70 C. to room temperature for ½ to 12 hours.

Process F (for compounds of structure XI or XII when Y and Z are both N, especially for non-racemic compounds where $R^1$ and $R^{27}$ are both $CH_3$)

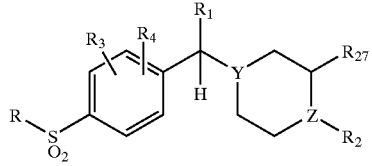

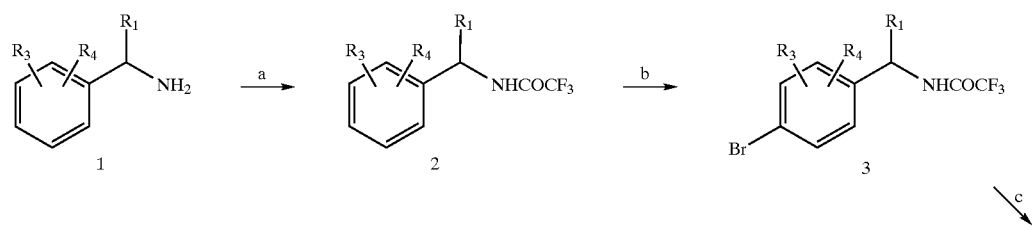

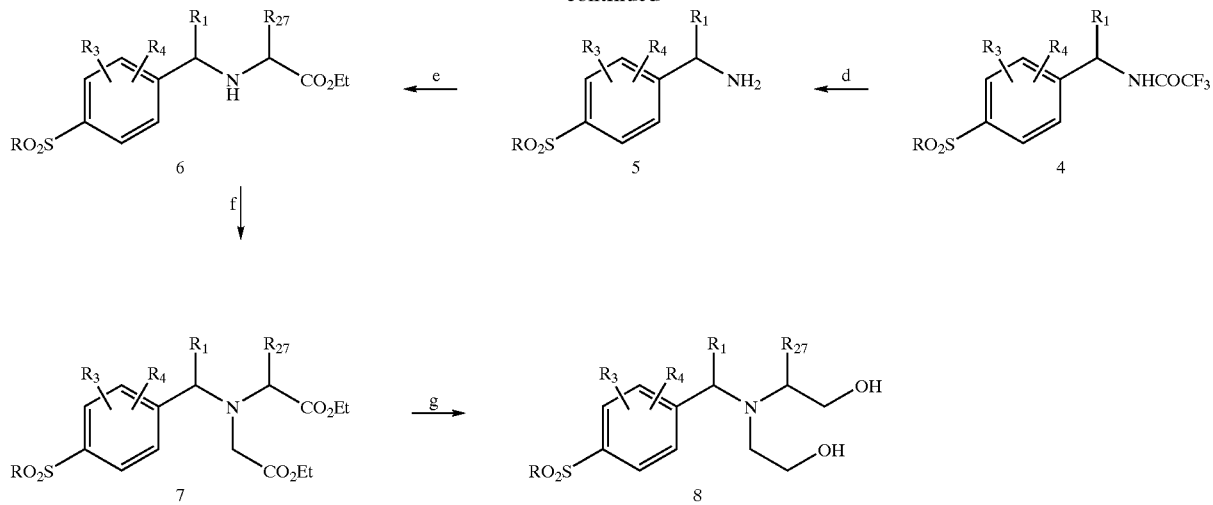

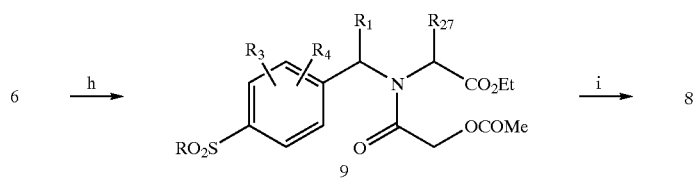

Reagents: a: $(CF_3CO)_2O$; b: dibromodimethylhydantoin, $CH_3SO_3H$; c: MeLi, then n-BuLi, then $RSO_2F$; d: NaOH; e: $R_{27}CH(OSO_2CF_3)CO_2Et$, $K_2CO_3$; f: $ICH_2CO_2Et$, $Na_2CO_3$; g: $LiAlH_4$; h: $AcOCH_2COCl$; i: $BH_3.Me_2S$.

Reaction of diol (8) with thionyl chloride gives a mixture of chlorides (10), which are in equilibrium with each other. This mixture is reacted with primary amines to afford compounds of the invention (11) and (12).

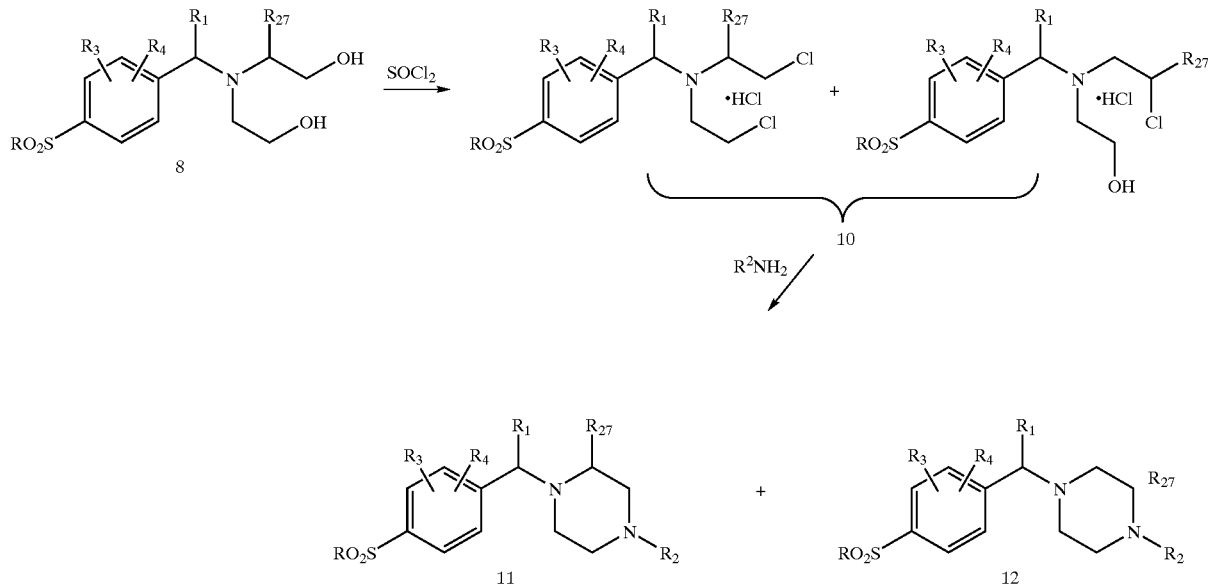

When the starting material 1 and reagent $R_{27}CH(OSO_2CF_3)CO_2Et$ are optically pure or enriched, the products 11 and 12 are non-racemic.

Process G

For compounds of formula I where $R^1$ is alkyl, $R^{21}$ is H, and Y is N, especially compounds of this type when X is $SO_2$ and the carbon to which $R^1$ and $R^{21}$ are attached is not racemic.

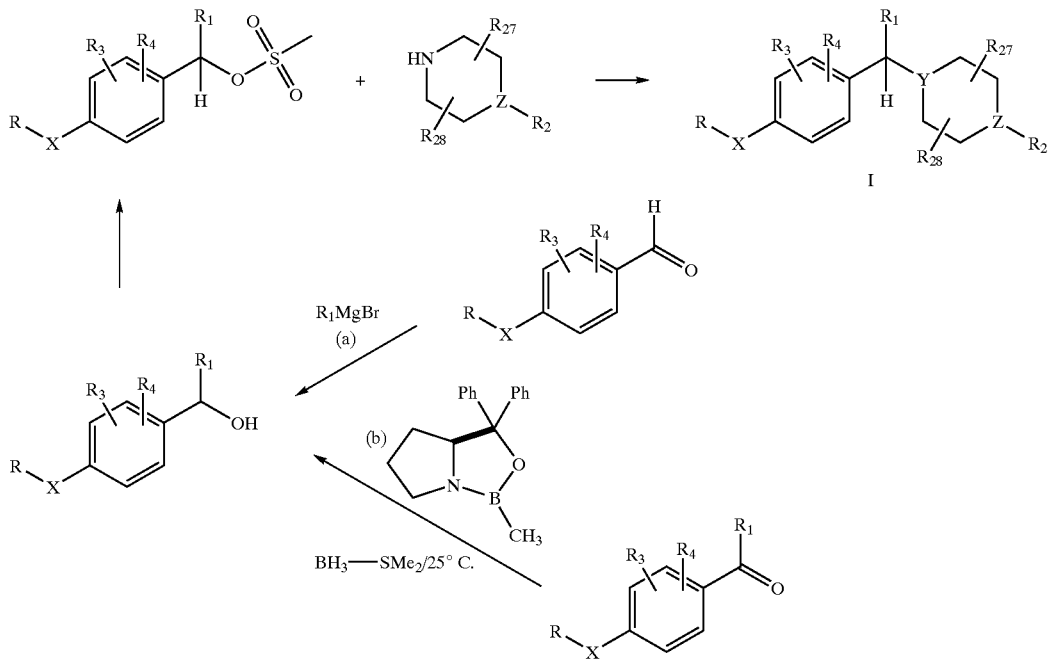

The above reactions may be followed if necessary or desired by one or more of the following steps; (a) removing any protective groups from the compound so produced; (b) converting the compound so-produced to a pharmaceutically acceptable salt, ester and/or solvate; (c) converting a compound in accordance with formula I so produced to another compound in accordance with formula I, and (d) isolating a compound of formula I, including separating stereoisomers of formula I.

Based on the foregoing reaction sequence, those skilled in the art will be able to select starting materials needed to produce any compound in accordance with formula I.

In the above processes it is sometimes desirable and/or necessary to protect certain groups during the reactions. Conventional protecting groups, familiar to those skilled in the art, are operable. After the reaction or reactions, the protecting groups may be removed by standard procedures.

The compounds of formula I exhibit selective m2 and/or m4 muscarinic antagonizing activity, which has been correlated with pharmaceutical activity for treating cognitive disorders such as Alzheimers disease and senile dementia.

The compounds of formula I display pharmacological activity in jest procedures designated to indicate m1 and m2 muscarinic antagonist activity. The compounds are non-toxic at pharmaceutically therapeutic doses. Following are descriptions of the test procedures.

Muscarinic Binding Activity

The compound of interest is tested for its ability to inhibit binding to the cloned human m1, m2, m3, and m4 muscarinic receptor subtypes. The sources of receptors in these studies were membranes from stably transfected CHO cell lines which were expressing each of the receptor subtypes. Following growth, the cells were pelleted and subsequently homogenized using a Polytron in 50 volumes cold 10 mM Na/K phosphate buffer, pH 7.4 (Buffer B). The homgenates were centrifuged at 40,000×g for 20 minutes at 4° C. The resulting supernatants were discarded and the pellets were resuspended in Buffer B at a final concentration of 20 mg wet tissue/ml. These membranes were stored at −80° C. until utilized in the binding assays described below.

Binding to the cloned human muscarinic receptors was performed using $^3$H-quinuclidinyl benzilate (QNB) (Watson et al., 1986). Briefly, membranes (approximately 8, 20, and 14 μg of protein assay for the m1, m2, and m4 containing membranes, respectively) were incubated with $^3$H-QNB (final concentration of 100–200 pM) and increasing concentrations of unlabeled drug in a final volume of 2 ml at 25° C. for 90 minutes. Non-specific binding was assayed in the presence of 1 μM atropine. The incubations were terminated by vacuum filtration over GF/B glass fiber filters using a Skatron filtration apparatus and the filters were washed with cold 10 mM Na/K phosphate butter, pH 7.4. Scintillation cocktail was added to the filters and the vials were incubated overnight. The bound radioligand was quantified in a liquid scintillation counter (50% efficiency). The resulting data were analyzed for $IC_{50}$ values (i.e. the concentration of compound required to inhibit binding by 50%) using the EBDA computer program (McPherson, 1985). Affinity values ($K_i$) were then determined using the following formula (Cheng and Prusoff, 1973);

$$K_i = \frac{IC_{50}}{1 + \left[\frac{\text{concentration of radioligand}}{\text{affinity}(K_D)\text{ of radioligand}}\right]}$$

Hence a lower value of $K_i$ indicates greater binding affinity.

The following publications, the entire contents of which are incorporated herein by reference, explain the procedure in more detail.

Cheng, Y.-C. and Prusoff, W. H., Relationship between the inhibitory constant ($K_i$) and the concentration of inhibitor which causes 50 per cent inhibition ($IC_{50}$) of an enzymatic reaction. Biochem. Pharmacol. 22: 3099–3108, 1973.

McPherson, G. A. Kinetic, EBDA, Ligand, Lowry: A Collection of Radioligand Binding Analysis Programs. Elsevier Science Publishers BV, Amsterdam, 1985.

Watson, M. J, Roeske, W. R. and Yamamura, H. I. [$^3$H] Pirenzepine and (-)[$^3$H)quinuclidinyl benzilate binding to rat cerebral cortical and cardiac muscarinic cholinergic sites. Characterization and regulation of antagonist binding to putative muscarinic subtypes. J. Pharmacol. Exp. Ther. 237: 411–418, 1986.

To determine the degree of selectivity of a compound for binding the m2 receptor, the $K_i$ value for m1 receptors was divided by the $K_i$ value for m2 receptors. A higher ratio indicates a greater selectivity for binding the m2 muscarinic receptor.

MICRODIALYSIS METHODOLOGY

The following procedure is used to show that a compound functions as an m2 antagonist.

Surgery: For these studies, male Sprague-Dawley Rats (250–350 g) were anesthetized with sodium pentobarbital (54 mg/kg, ip) and placed on a Kopf sterotaxic apparatus. The skull was exposed and drilled through to the dura at a point 0.2 mm anterior and 3.0 mm lateral to the bregma. At these coordinates, a guide cannula was positioned at the outer edge of the dura through the drilled opening, lowered perpendicularly to a depth of 2.5 mm, and permanently secured with dental cement to bone screws. Following the surgery, rats were given ampicillin (40 mg/kg, ip) and individually housed in modified cages. A recovery period of approximately 3 to 7 days was allowed before the microdialysis procedure was undertaken.

Microdialysis: All of the equipment and instrumentation used to conduct in vivo microdialysis was obtained from Bioanalytical Systems, Inc. (BAS). The microdialysis procedure involved the insertion through the guide cannula of a thin, needle-like perfusable probe (CMA/12,3 mm×0.5 mm) to a depth of 3 mm in striatum beyond the end of the guide. The probe was connected beforehand with tubing to a microinjection pump (CMA-/100). Rats were collared, tethered, and, following probe insertion, were placed in a large, clear, plexiglass bowl with litter material and access to food and water. The probe was perfused at 2 µl/min with Ringer's buffer (NaCl 147 mM; KCl 3.0 mM; $CaCl_2$ 1.2 mM; $MgCl_2$ 1.0 mM) containing 5.5 mM glucose, 0.2 mM L-ascorbate, and 1 µM neostigmine bromide at pH 7.4). To achieve stable baseline readings, microdialysis was allowed to proceed for 90 minutes prior to the collection of fractions. Fractions (20 µl) were obtained at 10 minute intervals over a 3 hour period using a refrigerated collector (CMA170 or 200). Four to five baseline fractions were collected, following which the drug or combination of drugs to be tested was administered to the animal. Upon completion of the collection, each rat was autopsied to determine accuracy of probe placement.

Acetylcholine (ACh) analysis: The concentration of ACh in collected samples of microdialysate was determined using HPLC/electrochemical detection. Samples were auto-injected (Waters 712 Refrigerated Sample Processor) onto a polymeric analytical HPLC column (BAS, MF-6150) and eluted with 50 mM $Na_2HPO_4$, pH 8.5. To prevent bacterial growth, Kathon CG reagent (0.005%) (BAS) was included in the mobile phase. Eluent from the analytical column, containing separated ACh and choline, was then immediately passed through an immobilized enzyme reactor cartridge (BAS, MF-6151) coupled to the column outlet. The reactor contained both acetylcholinesterase and choline oxidase covalently bound to a polymeric backbone. The action of these enzymes on ACh and choline resulted in stoichiometric yields of hydrogen peroxide, which was electrochemically detected using a Waters 460 detector equipped with a platinum electrode at a working potential of 500 mvolts. Data acquisition was carried out using an IBM Model 70 computer equipped with a microchannel IEEE board. Integration and quantification of peaks were accomplished using "Maxima" chromatography software (Waters Corporation). Total run time per sample was 11 minutes at a flow rate of 1 ml/min. Retention times for acetylcholine and choline were 6.5 and 7.8 minutes, respectively. To monitor and correct for possible changes in detector sensitivity during chromatography, ACh standards were included at the beginning, middle and end of each sample queue.

Increases in ACh levels are consistent with presynaptic m2 receptor antagonism.

RESULTS OF THE TESTS

For compoud numbers 169, 227(-), 289, 269, 214, 232, 123, 236, 296, 300, 301, 302, 304, and 305:

Ki, nM, m1: 2.1 to 224

Ki, nM, m2: 0.05 to 16.6 m2 selectivity ration (Ki, m1/Ki, m2)=9.3 to 42

Ki, nM, m4: 0.33 to 36 m4 selectivity ration (Ki, m1/Ki, m4): 3 to 12

For the persenly preferred compounds, compound numbers 615, 633, 622, 650, 667, 656, 658, 757, 763, 760, 690, 711, 719, 726, 714, 777, 795, and 801:

Ki, nM, m2=0.03 to 0.48

Selectivity:

m1/m2=30 to 68 m3/m2=5 to 66 m4/m2=2 to 10.

Presently the most preferred compounds are numbers 667, 760, 801, and 805.

Numerous other compounds in accordance with formula I were tested with the following range of results:

$K_i$ binding to m1 receptor, nM: 0.01 to 4770 with undetermined values up to >4200. An undetermined value occurred when a $K_i$ was not completely determined, but was found to be above some value of up to 4200 nM.

$K_i$ binding to m2 receptor, nM: 0.01 to 1525 with undetermined values up to >4600. An undetermined value occurred when a $K_i$ was not completely determined, but was found to be above some value of up to 4600 nM.

m2 Selectivity Ratio [$K_i$ for m1/$K_i$ for m2]

0.3 to 41.5 without regard to any undetermined $K_i$ values.

When compound No. 169 from the table of compounds was administered the following increases in ACh release above baseline levels were measured.

Figure 2:
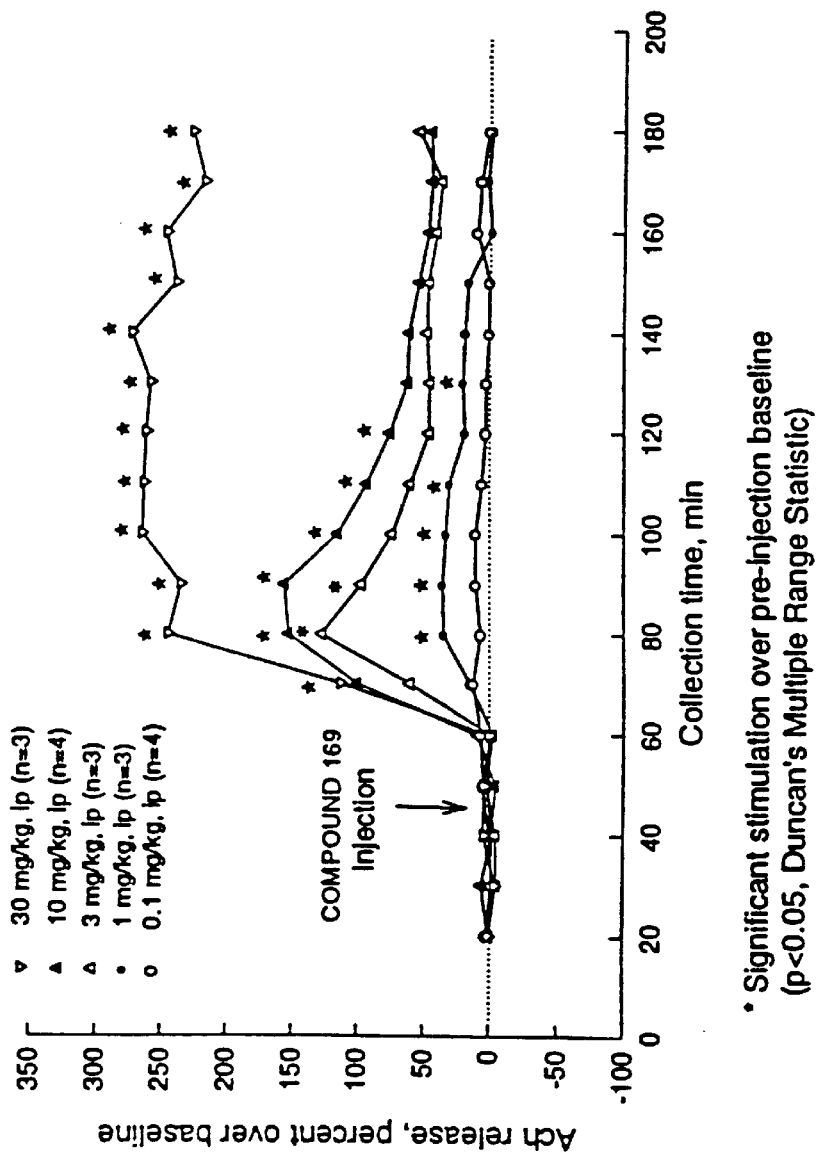
FIG. 2 is a plot similar to FIG. 1 for ACh release from the striatum following i.p. administration.

| Dosage mg/kg (Compound 169) | Peak ACh release as % increase over Baseline |
|---|---|
| From Cortex Of Conscious Rat (i.p. administration) | |
| (FIG. 1) | |
| 30 | 1500 |
| 10 | 400 |
| 1 | 75 |
| From Striatum of Conscious Rat (i.p. Administration) | |
| (FIG. 2) | |
| 30 | 270 |
| 10 | 150 |
| 3 | 125 |
| 1 | 30 |
| 0.1 | 10 |

Oral administration of compound 169 also caused a significant increase in ACh release.

We have made the surprising discovery that compounds of formula I in combination with an acetylcholinesterase (ACh' ase) inhibitor have a synergistic effect on ACh release, as shown below. Here Tacrine was used as the ACh'ase inhibitor.

Figure 3:
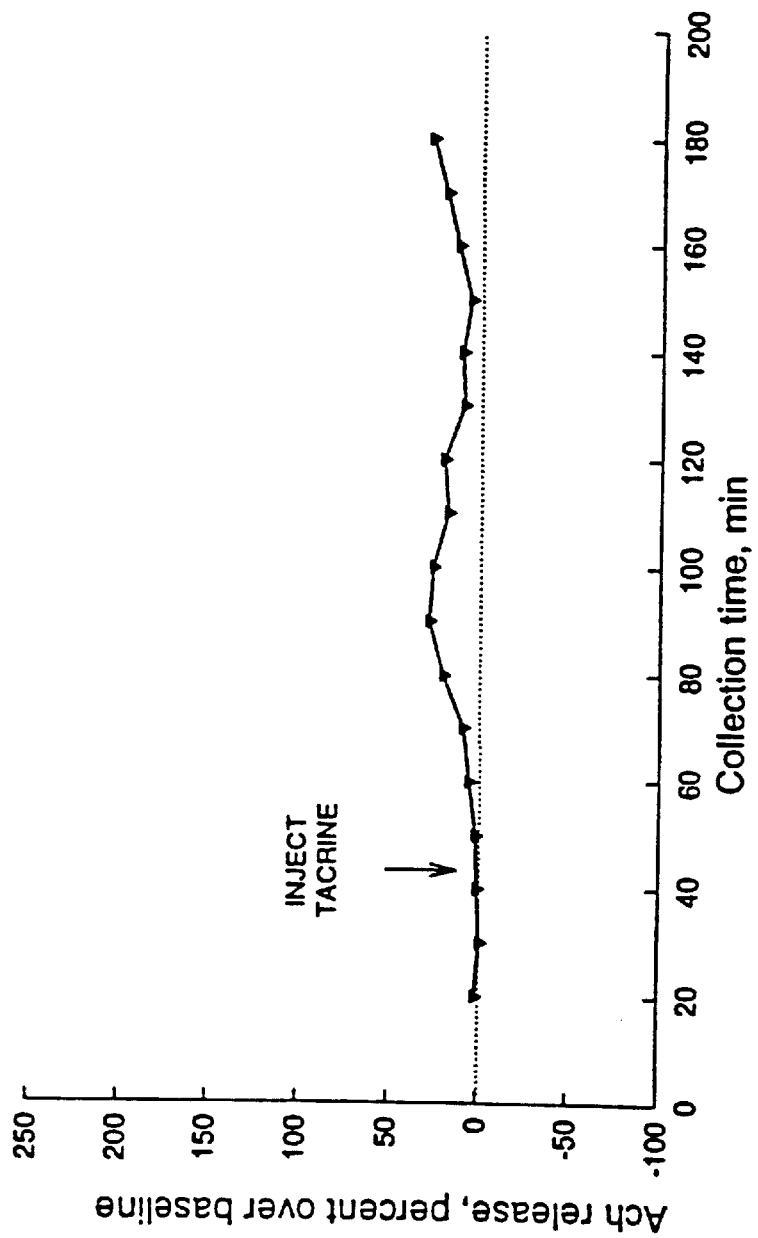
FIG. 3 illustrates the effect of 3 mg/kg of Tacrine (i.p. administration) on ACh release from striatum of conscious rat.
Figure 4:
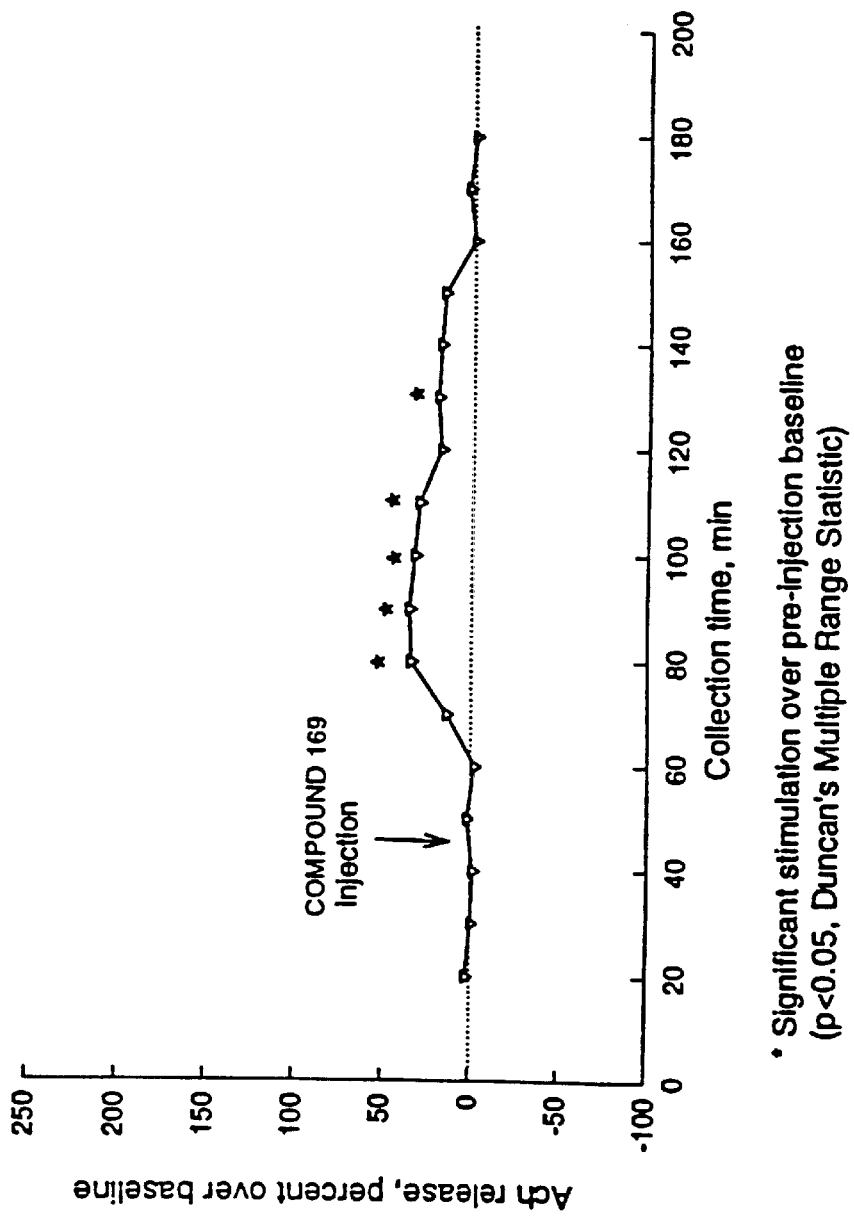
FIG. 4 is a plot similar to FIG. 4 for 1 mg/kg of a compound of this invention (i.p. administration).
Figure 5:
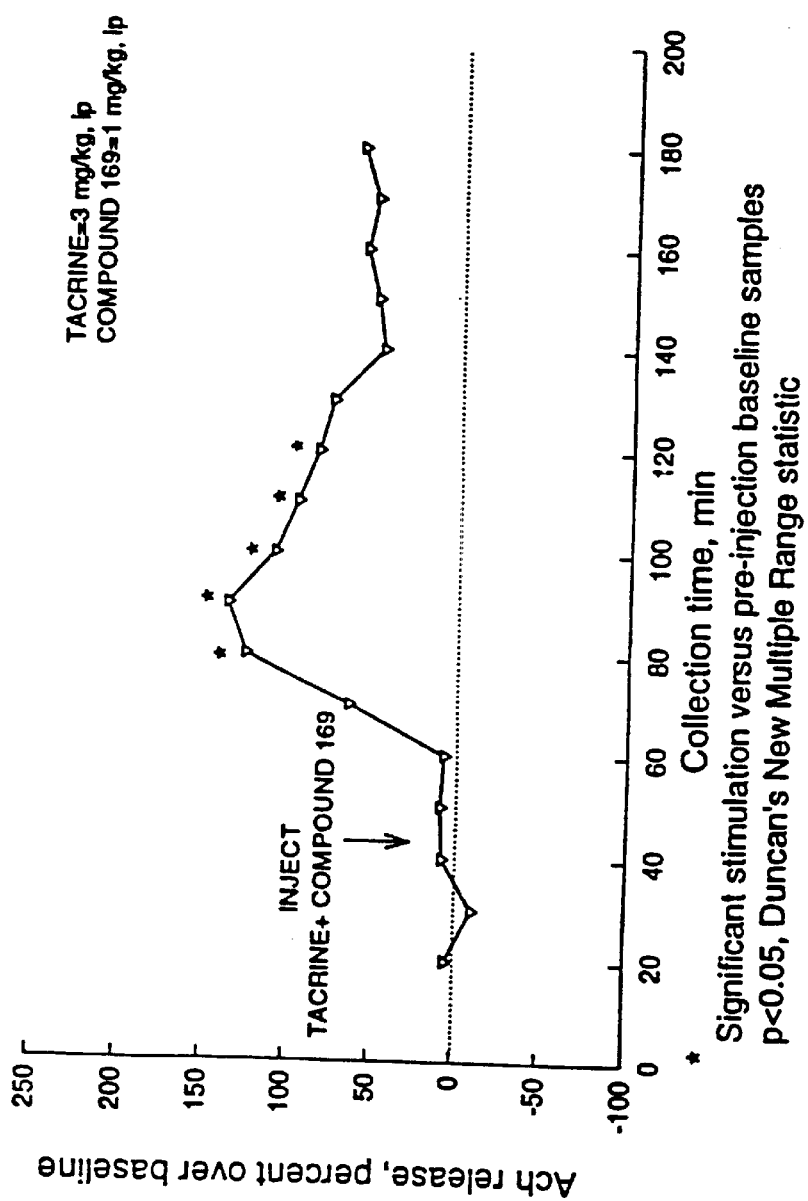
FIG. 5 is a plot similar to FIG. 4 for 1 mg/kg of a compound of this invention in combination with 3 mg/kg of Tacrine (both i.p. administration).

| Dose | Peak ACh release as % increase over Baseline (FIGS. 3 to 5) |
|---|---|
| From Striatum of Conscious Rat | |
| Tacrine 3 mg/kg (i.p.) | 30 (FIG. 3) |
| Compound 169 1 mg/kg (i.p.) | 40 (FIG. 4) |
| Tacrine 3 mg/kg and Compound 169 1 mg/kg (i.p.) | 130 (FIG. 5) |

As shown immediately above, when administered in combination, compound 169 and tacrine produce a synergistic increase in ACh release.

The present invention also relates to achieving similar synergistic results by administering a compound of formula I in combination with any other ACh' ase inhibitor including, but not limited to, E-2020 (available from Eisai Pharmaceutical) and heptylphysostigmine.

The present invention also relates to achieving similar synergistic results by administering any compound capable of enhancing ACh release, such as scopolamine or QNB in combination with an ACh'ase inhibitor. Preferably the ACh release enhancing compound is an m2 selective muscarinic antagonist, i.e. one having a ($K_i$ for m1/$K_i$ for m2) ratio greater than 1 or an m4 selective muscarinic antagonist (Ki for m1/Ki for m4 greater than 1). The m2 or m4 selective muscarinic antagonists for practicing this aspect of the invention include without limitation 3-α-chloroimperialine, AF-DX 116, AF-DX 384, BIBN 99 (these three compounds being available from Boehringer-Ingleheim), tripitramine, and himbacine.

For preparing pharmaceutical compositions from the compounds of formula I, compounds capable of enhancing ACh release, and ACh'ase inhibitors, pharmaceutically acceptable, inert carriers are admixed with the active compounds. The pharmaceutically acceptable carriers may be either solid or liquid. Solid form preparations include powders, tablets, dispersible granules, capsules, cachets and suppositories. A solid carrier can be one or more substances which may also act as dilutents, flavoring agents, solubilizers, lubricants, suspending agents, binders or tablet disintegrating agents; it may also be an encapsulating material.

Liquid form preparations include solutions, suspensions and emulsions. As an example may be mentioned water or water-propylene glycol solutions for parenteral injection.

Also included are solid form preparations which are intended to be converted, shortly before use, to liquid form preparations for either oral or parentertal administration. Such liquid forms include solutions, suspensions and emulsions. These particular solid form preparations are most conveniently provided in unit dose form and as such are used to provide a single liquid dosage unit.

The invention also contemplates alternative delivery systems including, but not necessarily limited to, transdermal delivery. The transdermal compositions can take the form of creams, lotions and/or emulsions and can be included in a transdermal patch of the matrix or reservoir type as are conventional in the art for this purpose.

Preferably, the pharmaceutical preparation is in unit dosage form. In such form, the preparation is subdivided into unit doses containing appropriate quantities of the active components. The unit dosage form can be a packaged preparation, the package containing discrete quantities of preparation such as packeted tablets, capsules and powders in vials or ampules. The unit dosage form can also be a capsule, cachet or tablet itself, or it may be the appropriate number of any of these in a packaged form.

The quantity of active compound in a unit dose preparation may be varied or adjusted from 1 mg to 100 mg according to the particular application and the potency of the active ingredient and the intended treatment. This would correspond to a dose of about 0.001 to about 20 mg/kg which may be divided over 1 to 3 administrations per day. The composition may, if desired, also contain other therapeutic agents.

The dosages may be varied depending on the requirement of the patient, the severity of the condition being treating and the particular compound being employed. Determination of the proper dosage for a particular situation is within the skill of those in the medical art. For convenience, the total daily dosage may be divided and administered in portions throughout the day or by means providing continuous delivery.

When a compound of formula I or a compound capable of enhancing ACh release is used in combination with an acetylcholinesterase inhibitor to treat cognitive disorders these two active components may be co-administered simultaneously or sequentially, or a single pharmaceutical composition comprising a compound of formula I or a compound capable of enhancing ACh release and an acetylcholinesterase inhibitor in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the acetylcholinesterase inhibitor may range from 0.001 to 100 mg/kg body weight.

The invention disclosed herein is exemplified by the following preparation and examples which should not be construed to limit the scope of the disclosure. Alternative mechanistic pathways and analogous structures may be apparent to those skilled in the art.

PREPARATIONS

Preparation 1

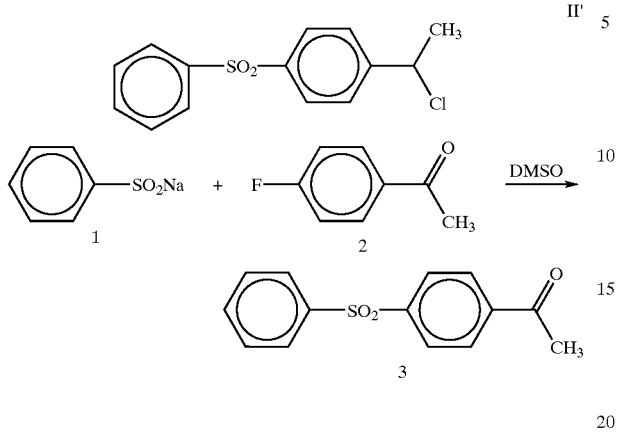

21.4 g (130 mmol) of 1 and 15.0 g (108.6 mmol) of 2 were placed in a round bottom flask. DMSO (100 ml) was added and the mixture was warmed to 130° C. where it was stirred for 70 hours. The reaction was cooled and poured into 400 g of ice and stirred thoroughly. The mixture was filtered and a white precipitate was collected which was washed with water. The solid was recrystallized from ethanol.

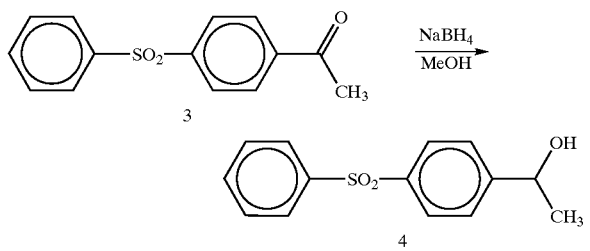

Compound 3 (13.72 g, 52.7 mmol) was dissolved in methanol (100 ml) and cooled to 0° C. where NaBH$_4$ (1.2 g, 31.6 mmol) was added in small portions. The mixture was stirred for one half hour, then warmed to reflux, stirred for 4 hours, and cooled to room temperature. The solvent was removed on a rotary evaporator. The residue was dissolved in ethyl acetate (400 ml) and washed with water and brine, dried over Na$_2$SO$_4$ and then filtered. The solvent was removed with a rotary evaporator.

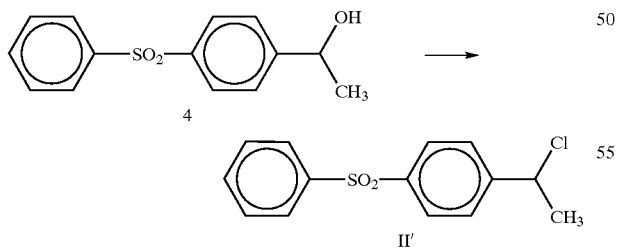

A CH$_2$Cl$_2$ (120 ml) solution of 4 (14 g, 53 mmol) was cooled to 0° C. and SOCl$_2$ (7.8 ml, 107 mmol), in 20 ml CH$_2$Cl$_2$ was added over a 30 minute period. The mixture was warmed to room temperature and stirred overnight. The volatiles were removed on a rotary evaporator and the residue dissolved in 500 ml ethyl acetate. The organic solution was washed with water, saturated with NaHCO$_3$, and brine. The mixture was dried over Na$_2$SO$_4$, filtered and the solvent was removed on a rotary evaporator.

Preparation 2

Compound 6 (25 g, 180 mmol) was dissolved in 80 ml DMF and cooled to 0° C. Sodium hydride (7.2 g 60% dispersion in mineral oil) was added under nitrogen. Stirring was continued for 20 minutes then the reaction mixture was warmed to room temperature when compound 5 (20 g, 180 mmol), dissolved in 40 ml DMF, was added with syringe. The solution was heated to 100° C. and stirred for 3 hours, then cooled to room temperature. DMF was removed with a rotary evaporator, then 250 ml water was added and the pH adjusted with NaOH to 12. The solution was extracted with ethyl acetate, dried over Na$_2$SO$_4$ and filtered. The solvent was then removed with a rotary evaporator.

Compound 7 (22 g, 100 mmol) was dissolved in 450 ml EtOH, and cooled to 0° C. NaBH$_4$ (1.9 g, 51 mmol) was added in portions. The mixture was warmed to room temperature and stirred overnight. Water (300 ml) was added and then removed on a rotary evaporator. Ethyl acetate was added to the residue which was then washed with water. The organic layer was dried over Na$_2$SO$_4$, filtered, and removed with a rotary evaporator.

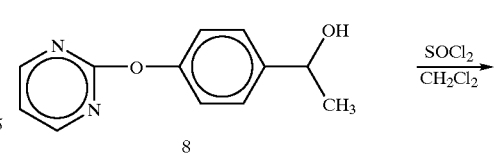

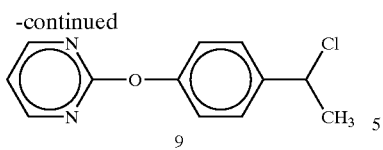

Compound 8 (22 g, 100 mmol) was dissolved in 400 ml $CH_2Cl_2$ and cooled to 0° C. $SOCl_2$ (9 ml, 120 mmol) was dissolved in $CH_2Cl_2$ (50 ml) and added to compound 8 with a dropping funnel, under nitrogen. After addition was complete, the mixture was stirred at 0° C for ½ an hour, then at room temperature for 2 hours. The solution was decanted into an Erlenmeyer flask to remove the precipitate. 10% $NaHCO_3$ was added until the pH of the aqueous layer was 8. The layers were separated and the $CH_2Cl_2$ layer was dried with $MgSO_4$. The layer was then filtered and the solvent was removed on a rotary evaporator.

Preparation 3

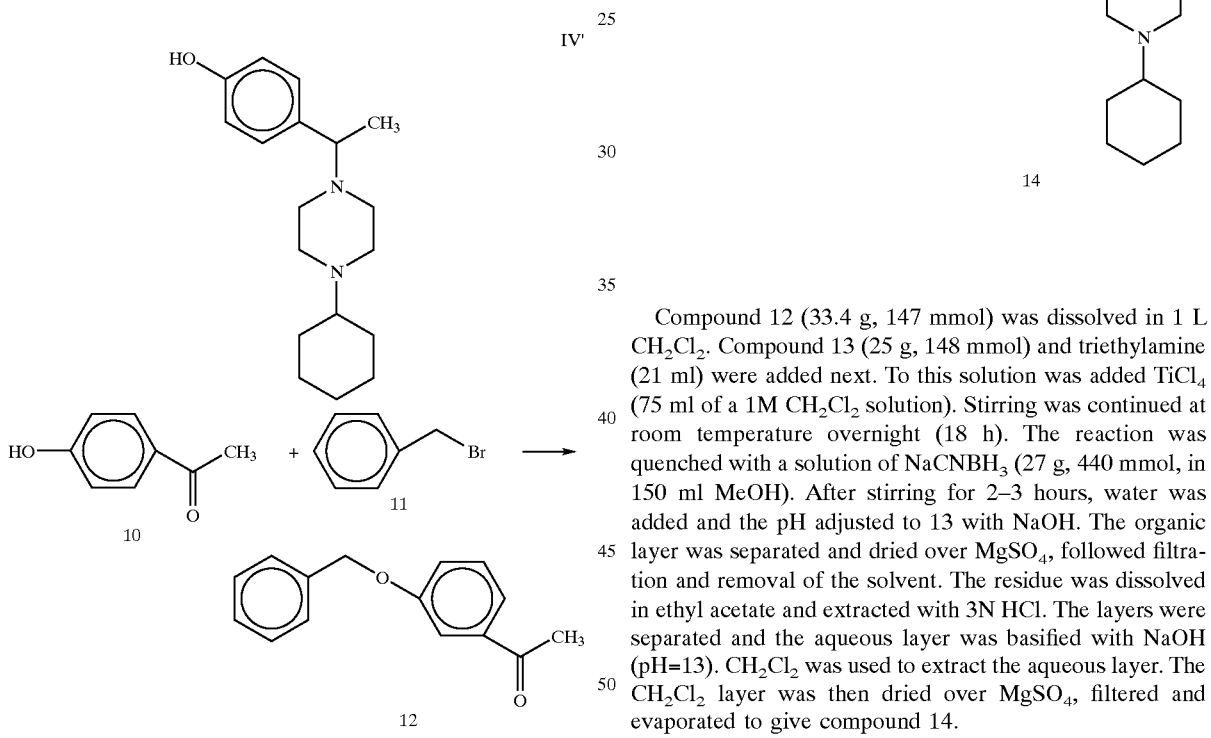

Compound 10 (54 g, 400 mmol) was dissolved in 500 ml DMF and cooled to 0° C. $NaOCH_3$ (20.5 g) was added in portions with stirring. The ice bath was removed and compound 11 (68.4 g, 400 mmol) was added with stirring. The mixture stirred at room temperature for 3 hours, then at 80° C. for 1 hour, and cooled to room temperature. The DMF solution was concentrated to 200 ml, then 400 ml water and 300 ml ethyl acetate was added with stirring by a mechanical stirrer. The pH was made basic with NaOH, and the organic layer was separated, and dried over $MgSO_4$. The solution was filtered and the solvent was then removed by a rotary evaporator.

Compound 12 (33.4 g, 147 mmol) was dissolved in 1 L $CH_2Cl_2$. Compound 13 (25 g, 148 mmol) and triethylamine (21 ml) were added next. To this solution was added $TiCl_4$ (75 ml of a 1M $CH_2Cl_2$ solution). Stirring was continued at room temperature overnight (18 h). The reaction was quenched with a solution of $NaCNBH_3$ (27 g, 440 mmol, in 150 ml MeOH). After stirring for 2–3 hours, water was added and the pH adjusted to 13 with NaOH. The organic layer was separated and dried over $MgSO_4$, followed filtration and removal of the solvent. The residue was dissolved in ethyl acetate and extracted with 3N HCl. The layers were separated and the aqueous layer was basified with NaOH (pH=13). $CH_2Cl_2$ was used to extract the aqueous layer. The $CH_2Cl_2$ layer was then dried over $MgSO_4$, filtered and evaporated to give compound 14.

-continued

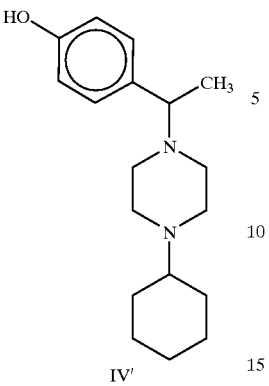

IV'

Ethanol (300 ml) was added to compound 14 (17 g, 45 mmol), followed by 2.5 g Pd(OH)₂/C. The mixture was placed on a Parr shaker for 1 to 8 hours monitored by TLC at 60 psi of hydrogen then filtered through Celite and the EtOH was removed. The residue was dissolved in ethyl acetate and washed in NaOH. The pH of the aqueous layer was then adjusted to 7, then the aqueous layer was extracted with CH₂Cl₂, dried with Na₂SO₄, then evaporated to produce compound IV'. This was then recrystalized from CH₃CN to produce pure IV'.

Preparation 4
(Process C)

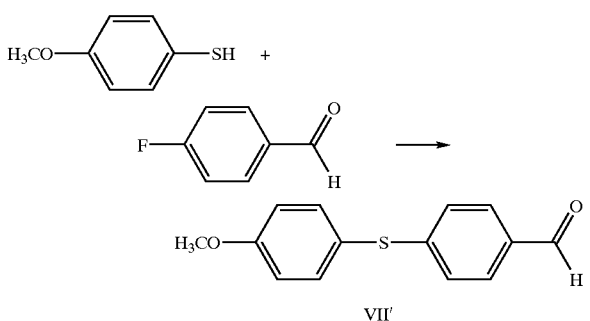

VII'

4.3 g (1 equivalent) of 60% sodium hydride dispersion in mineral oil was weighed into a flame-dried 250 ml flask under nitrogen. The mineral oil was removed by washing with hexane, and 100 ml of dry N,N-dimethylformamide was added by syringe. The suspension was cooled in an ice water bath while 15 g (1 equiv.) of 4-methoxythiophenol was added in portions. The mixture was stirred for 1 hour at room temperature after addition was complete, and 14.6 g (12.6 mL, 1.1 equiv.) of 4-fluorobenzaldehyde was added in one portion. The mixture was stirred for 3 days at room temperature, then poured slowly into 600 mL of ice water with vigorous stirring. The yellow solid was separated by filtration, then triturated twice with 150 mL portions of hexane by vigorous stirring. The product obtained is a light yellow powder, 23 g (88% yield), sufficiently pure for further reaction.

Preparation 5

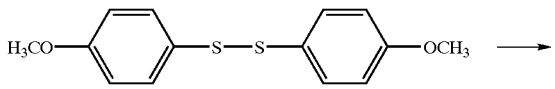

-continued

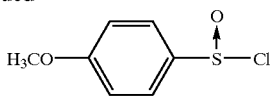

6.75 grams of bis(paramethoxyphenyl)disulfide were stirred with 3.6 mL of glacial acetic acid, and the mixture was cooled to −40° C. Sulfuryl chloride (7.5 mL) was added in portions, and the solution was maintained at −40° C. while the solid dissolved. The brown solution was warmed gradually to −20° C. and stirred for five hours, then warmed to 0° C. Gas was evolved during this period, and the solution darkened to green. The volatiles were removed in vacuo, and the crude material was used in the next reaction without delay.

Preparation 6

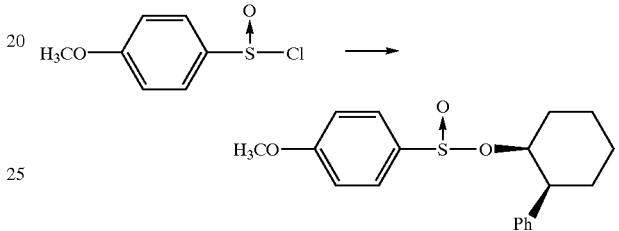

6.9 grams (39.1 mm) of (1R,2S)-2-phenylcyclohexanol (prepared in accordance with J. K. Whitesell, M-S Wong, J. Org. Chem, 56(14), p. 4552, 1991) were dissolved in 150 mL dry THF with 6 mL dry pyridine. The solution was cooled to −78° C,, and para-methoxyphenyl sulfinyl chloride (derived from 6.75 g of the corresponding disulfide) was added slowly. The solution developed a white precipitate as it was stirred at −78° C. for one hour. The reaction was quenched with saturated sodium bicarbonate, diluted with ethyl acetate, and extracted with bicarbonate solution and brine. The organic layers were dried over sodium sulfate, concentrated, and purified by column chromatography in a gradient of 10% ethyl acetate/hexane to 25% ethyl acetate/hexane, yielding 10 grams (78%) of the desired sulfinate, slightly contaminated with the minor diastereomer. This diastereomer was purified by crystallization from hexane/ethyl acetate, a procedure also applicable to the crude product.

Preparation 7

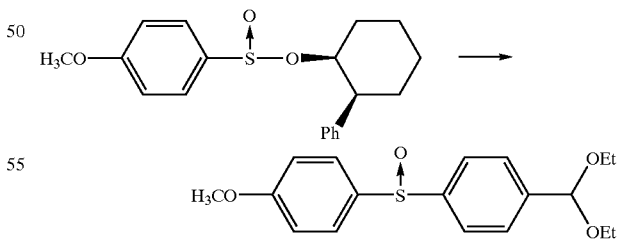

1.25 grams of magnesium turnings (52 mm, 2.3 equivalents) were stirred in 5 mL of dry THF. One drop of 1,2-dibromoethane was added, followed by a small portion (roughly one gram) of 4-bromobenzaldehyde diethyl acetal. The solution was heated to initiate formation of the Grignard reagent, and the remaining acetal (to a total of 11.2 grams, 45 mm, 2 equivalents) was added in portions, along with THF (to a total of 25 mL.) The mixture was heated to reflux for 45 minutes, then cooled to room temperature. The Grignard solution thus obtained was added in portions to a solution of the starting sulfinate ester (7.5 grams, 22.6 mm) in 150 mL dry toluene at 0° C. After one hour, the reaction was quenched with saturated sodium bicarbonate solution, diluted with ethyl acetate, and extracted with brine. The organic layers were dried over sodium sulfate, concentrated, and purified by brief column chomatography in 25% ethyl acetate/hexane to give recovered chiral alcohol and the desired acetal, which was used directly in the next reaction.

Preparation 8

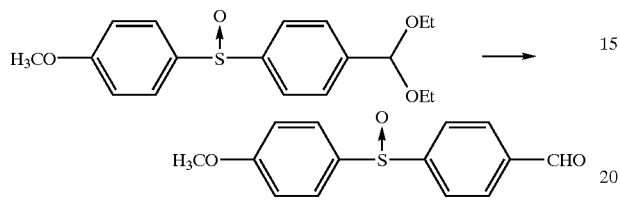

The acetal obtained from the reaction of 7.5 grams of sulfinate ester was taken up in 60 mL of THF with 10 mL distilled water. A catalytic amount of paratoluene sulfonic acid was added, and the solution was warmed to 60°. After three hours, the mixture was cooled to room temperature, diluted with ethyl acetate, and extracted with saturated sodium bicarbonate solution. The organic layers were dried over sodium sulfate and concentrated to give the desired aldehyde as a crystalline solid, 5.42 grams (97% over two steps).

Preparation 9

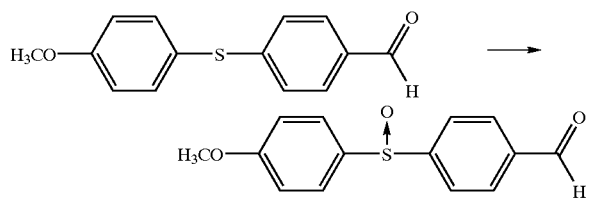

2 grams (8.17 mm) of the starting 4-(4-methoxyphenyl) thiobenzaldeyde and 1.75 g (1 equivalent of 80%) meta-chloroperbenzoic acid were taken up in 40 mL of dichloromethane at 0°. After 30 minutes, 300 mg of additional MCPBA was added, and the reaction stirred 30 minutes more. The solution was diluted with ethyl acetate and extracted with saturated sodium bicarbonate. The organic layers were dried over sodium sulfate, concentrated, and the product was crystallized from ethyl acetate/hexane to give a first crop of 1.65 grams.

EXAMPLE 1

(Process A)

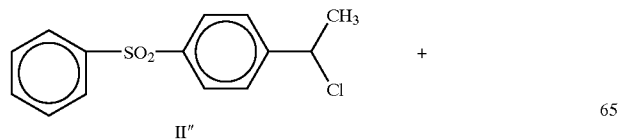

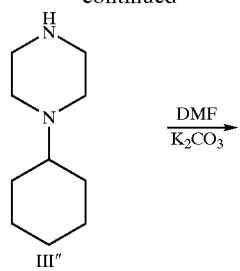

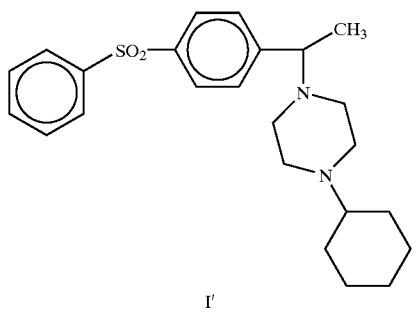

Compound II' (1.0 g, 3.5 mmol) was dissovled in DMF (10 ml), followed by addition of $K_2CO_3$ (1.5 g). Compound III' (0.66 g, 3.9 mmol) was next added. The mixture was warmed to 50° C. and maintained for 18 hours with stirring. The mixture was cooled to room temperature and ethyl acetate (EtOAc) (150 ml) was added. The organic layer was washed with water (5×50 ml) and saturated NaCl (1×25 ml). The organic layer was dried over $Na_2SO_4$, filtered, and the volatiles removed with a rotary evaporator. The resulting oil was purified by column chromatography, on silica gel, with ethyl acetate as solvent.

EXAMPLE 2

(Process A)

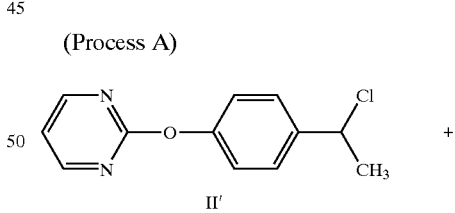

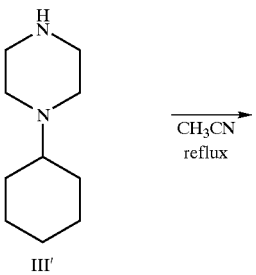

-continued

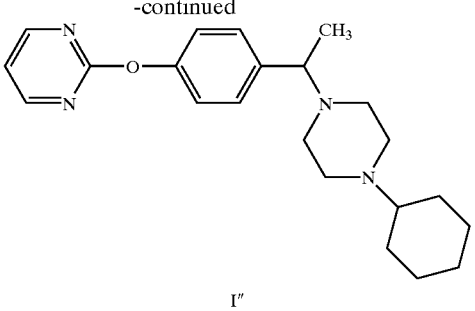

I″

To the solid chloride (770 mg) was added a solution of 2 equivalents of cyclohexylpiperazine in 5 mL CH₃CN. The mixture was heated with stirring at reflux for 2 hours then allowed to stand for 18 hours. The resulting solid was suspended in 1:1 EtOAc:water. The aqueous layer was basified with solid K₂CO₃. The organic layer was washed several times with water, dried with MgSO₄ and evaporated to obtain the crude product. This was purified by chromatography on a column of silica gel, (TLC grade), and 50:3:1 CH₂Cl₂:EtOH:NH₄OH as the eluant.

EXAMPLE 3
(Process B)

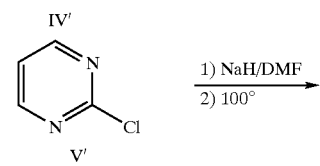

IV′

V′

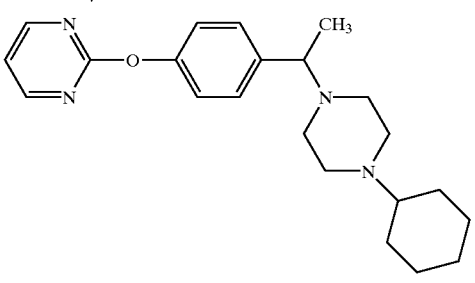

I‴

To an ice cold solution of compound IV′ (1 equivalent) in dry DMF under nitrogen was added 0.9 equivalents of NaH, (60% dispersion in mineral oil). After 20 minutes 2-chloropyrimidine was added (0.9 equivalents). The solution was heated at 100° C. for 4 hours. After cooling to room temperature water was added (10 mls per 1 ml DMF) and the solution extracted with ethyl acetate. The organic extracts were dried with MgSO₄ and evaporated to obtain the crude product which was then purified by column chromatography, (Silica gel, TLC grade and 50:3:1 CH₂Cl₂:EtOH:NH₄OH as eluant).

EXAMPLE 4
(Process C)

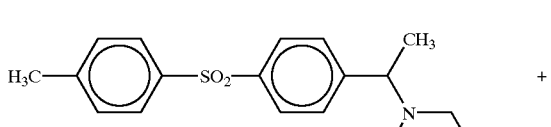

VI′

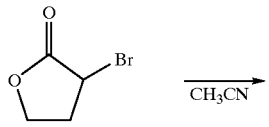

VII′

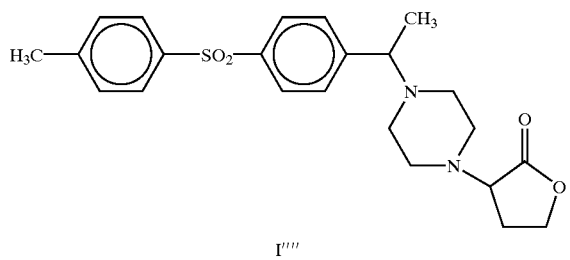

I″″

To a solution of VI′ (0.25 g, 0.73 mmol) in 5 ml acetonitrile was added a solution of VII′ (0.12 g, 0.73 mmol, dissolved in 3 ml acetonitrile). The mixture was stirred at room temperature (20° C.) for 0.5 hours, then warmed to 45° C. and stirred for 6 hours. The mixture was cooled to room temperature and ethyl acetate (150 ml) was added and the organic layer was washed with saturated NaCl (1×50 ml). The organic layer was dried over Na₂SO₄. The organic layer was filtered and the volatiles removed with a rotary evaporator. The resulting oil was purified by flash chromatography using 50 g silica gel and 9:1 CH₂Cl₂/MeOH (saturated with NH₄OH) as solvent. 0.19 g of a syrup was collected.

EXAMPLE 5
(process D)

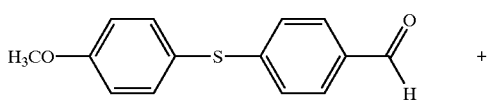

VIII′

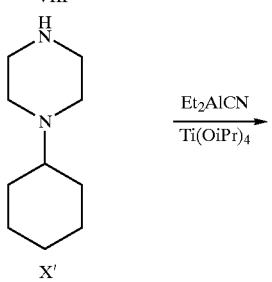

X′

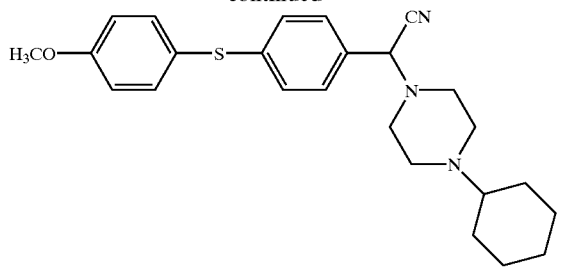

2 grams (8.17 mmol) of the starting 4-(4-methoxyphenyl)thiobenzaldehyde, VIII', and 1.65 g (10 ml, 1.2 equivalents) of N-cyclohexylpiperazine, X', were taken up under a nitrogen atmosphere in 1 mL of dry dichloromethane at room temperature. 2.9 mL (10 mmol, 1.2 equivalents) of titanium tetraisopropoxide were added by syringe, and the resulting solution was stirred at room temperature for 18 hours. The reaction developed a white precipitate during this period. The reaction was cooled in an ice water bath while 16.3 mL of a 1 molar toluene solution (2 equivalents) of diethylaluminum cyanide were added in portions by syringe. The resulting homogeneous red/brown solution was stirred for 30 minutes at room temperature. The reaction was diluted by the addition of 100 mL ethyl acetate, and quenched by the slow addition of 25 mL water, with vigorous stirring. After 1 hour, the inorganic solids were removed by filtration through Celite, and the filtrate was washed with a saturated brine solution and dried by anhydrous sodium sulfate. The product was concentrated, then purified by column chromatography in a gradient of acetate/hexane, yielding 3.29 grams of the desired product (95% yield.)

EXAMPLE 6

Hydrolysis of cyano compound to amide

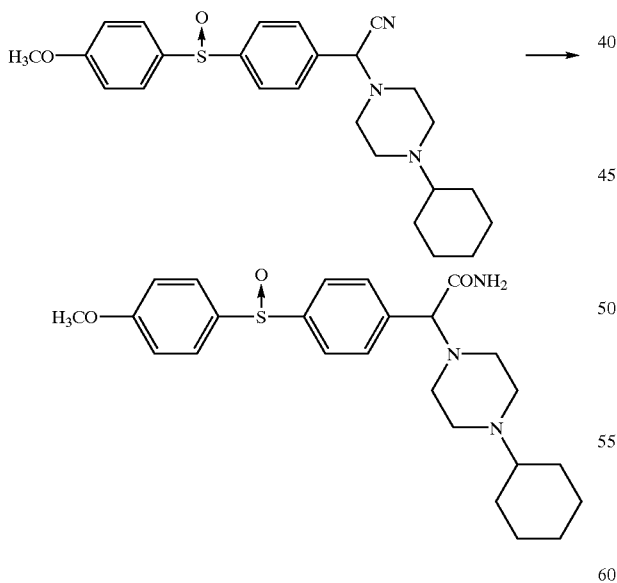

2 grams (4.6 mm) of the starting nitrile were stirred in 25 mL of tertiary butanol with 1.2 grams (21 mm) of powdered potassium hydroxide. The mixture was heated to reflux for 30 minutes, cooled to room temperature, and diluted with 250 mL of water. The solution was extracted twice with ethyl acetate, and the organic layers were dried over sodium sulfate. Evaporation gave the amide (2 grams, 96%) as an amorphous solid which can be used in subsequent reactions without further purification.

EXAMPLE 7

Hydrolysis of amide to acid

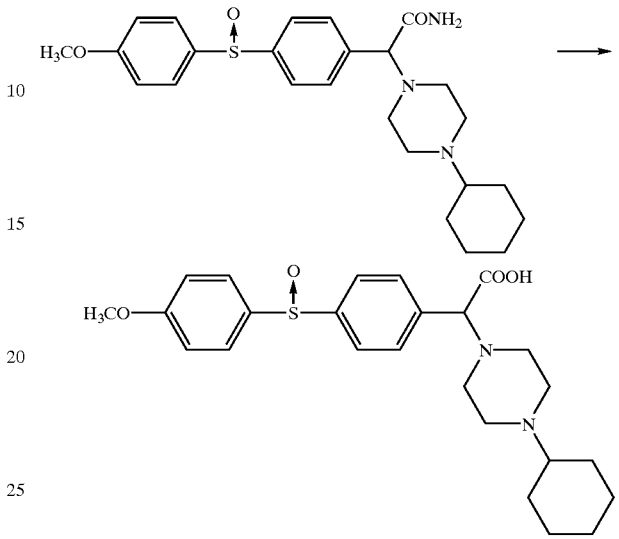

0.95 grams of starting amide (2.1 mm) were taken up in 20 mL of 4N hydrochloric acid. The reaction was heated to reflux for 16 hours. The volume of the solution was reduced in vacuo, whereupon the dihydrochloride salt of the desired product precipitated. The solid was isolated by filtration and washed with dry ethyl ether to give 0.85 grams of product, 77% yield. This solid was suitable for use without further purification.

EXAMPLE 8

Formation of Methyl Ester

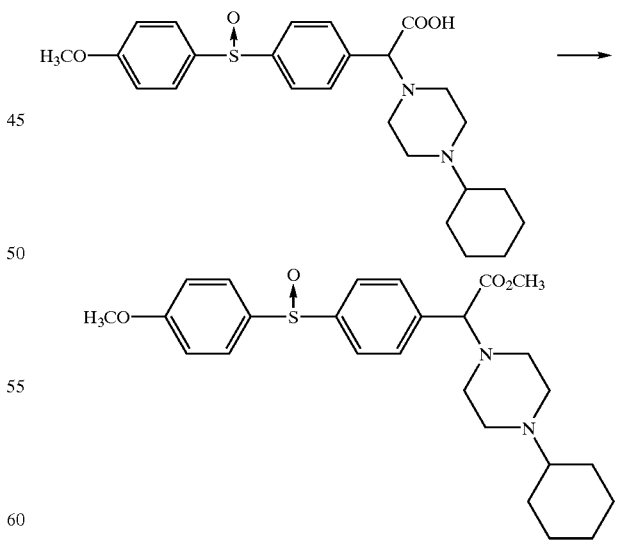

A solution of methanolic HCl was prepared by the addition of 3 mL of acetyl chloride to 50 mL of dry methanol. To this solution was added 400 milligrams (0.88 mm) of the starting acid. The flask was fitted with a Soxhlet extraction thimble containing freshly activated molecular sieves (3 Å), and the solution was heated to reflux for 16 hours. The reaction was cooled to room temperature, and the acid was neutralized with solid sodium carbonate. The solution was diluted with 300 mL of dichloromethane and washed with distilled water. The organic layers were dried over magnesium sulfate and purified by column chromatography in 3% methanol/dichloromethane to give 310 milligrams (76%) of the desired product.

EXAMPLE 9

Formation of tetrazole

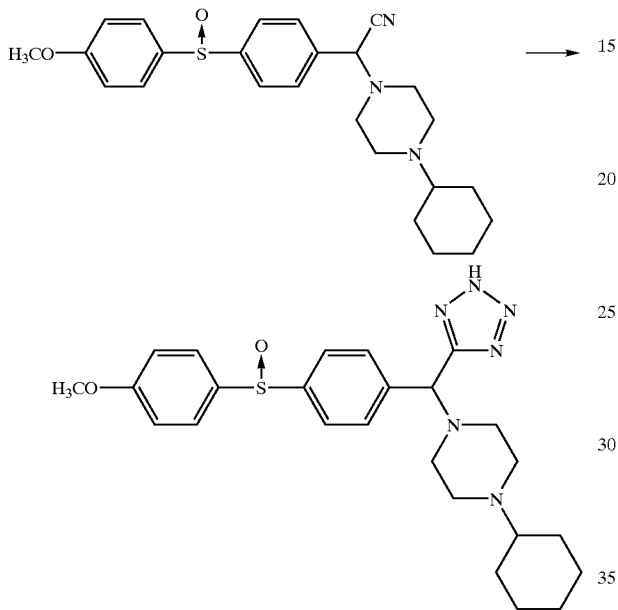

250 milligrams (0.57 mm) of the starting nitrile were taken up under a nitrogen atmosphere in 4 mL of dry toluene with 0.15 mL trimethylsilyl azide (2 equivalents) and 14 milligrams of dibutyltin oxide (1 equivalent). The solution was heated at 100° for 48 hours, whereupon additional equivalents of the azide and tin reagents were added and the solution was heated an additional 24 hours. The reaction was cooled to room temperature and evaporated to a brown solid, which was purified by preparative thin-layer chromatography in 20% methanol/dichloromethane. 27 milligrams of the desired tetrazole were isolated.

EXAMPLE 10

Alkylation of tetrazole

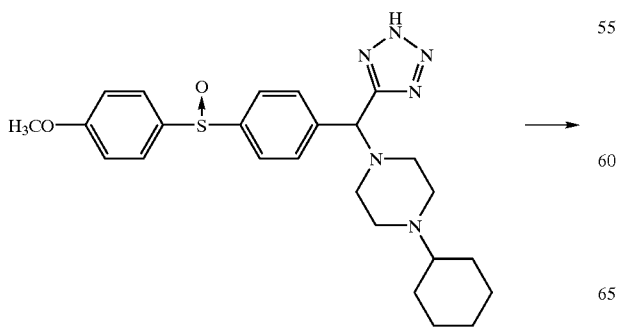

-continued

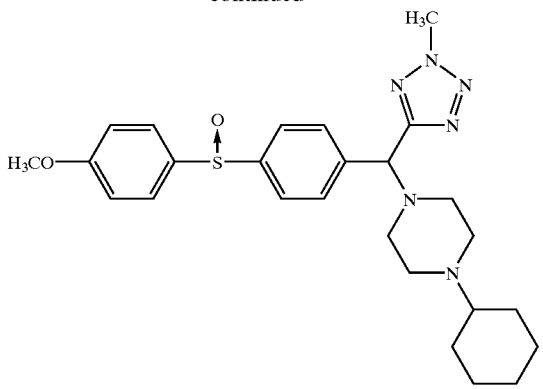

20 milligrams (0.57 mm) of the starting tetrazole were treated with an ethereal solution of diazomethane (excess) at 0°. The solution became homogeneous after ten minutes, and after an additional thirty minutes the solution was evaporated and purified by preparative thin-layer chromatograpy in 7.5% methanol/dichloromethane. 10 milligrams of product were isolated.

EXAMPLE 11

(Process E)

Alkylation of methyl ester

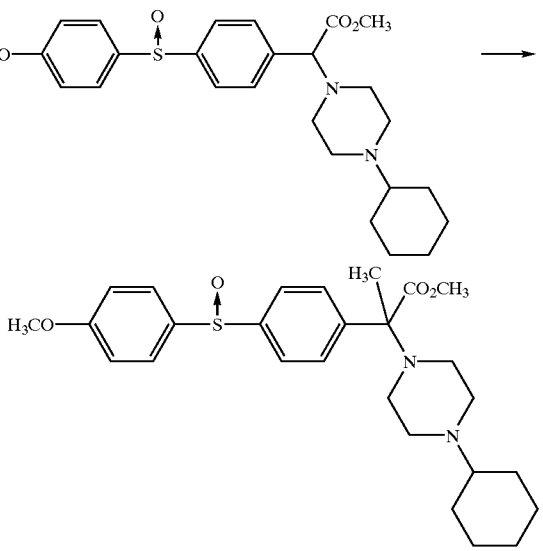

100 milligrams (0.2 mm) of the starting ester were taken up under a nitrogen atmosphere in 4 mL of dry tetrahydrofuran at 0°. 0.53 mL (0.26 mm, 1.3 equivalents) of potassium hexamethyldisilazide solution (0.5 M in toluene) were added by syringe, and the resulting solution was stirred for ten minutes. 0.02 mL of iodomethane (1.3 equivalents) were then added by syringe The reaction was stirred for 20 minutes while warming to room temperature, then diluted by the addition of 50 mL ethyl acetate, and extracted with saturated sodium bicarbonate solution and brine. The organic layers were dried by anhydrous sodium sulfate, concentrated, and purified by preparative thin-layer chromotography in 5% methanol/dichloromethane, giving 24 milligrams of the desired product.

EXAMPLE 12

Alpha-alkylation of cyano compounds

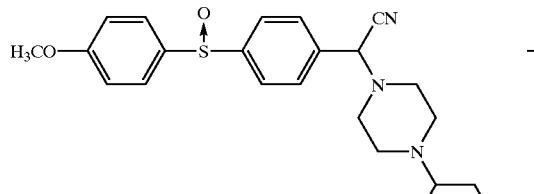

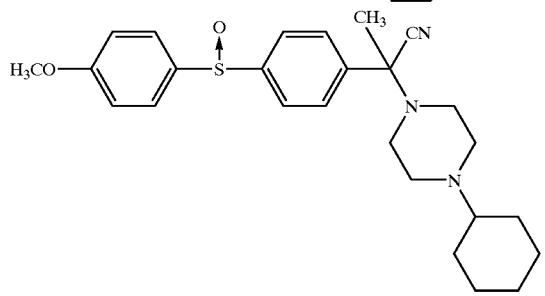

200 milligrams (0.46 mm) of the starting nitrile were taken up under a nitrogen atmosphere in 10 mL of dry tetrahydrofuran at 0°. 1.2 mL (0.6 mm, 1.3 equivalents) of potassium hexamethyldisilazide solution (0.5 M in toluene) were added by syringe, and the resulting orange solution was stirred for ten minutes. 0.05 mL of iodomethane (1.3 equivalents) were added by syringe, which decolorized the solution. The reaction was stirred for 20 minutes while warming to room temperature, then diluted by the addition of 100 mL ethyl acetate, and extracted with saturated sodium bicarbonate solution and brine. The organic layers were dried by anhydrous sodium sulfate, concentrated, and purified by column chromatography in a gradient of hexane/ethyl acetate, giving 190 milligrams of the desired product (92% yield) as an oil that slowly solidified.

EXAMPLE 13

Oxidation of Sulfide to Sulfoxide

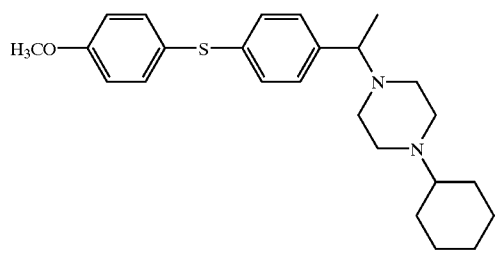

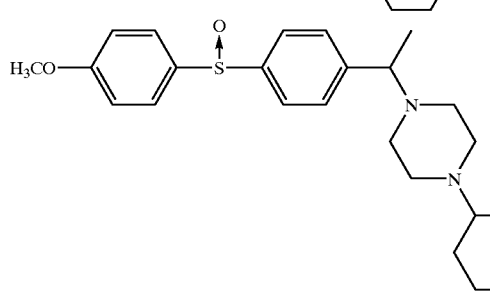

1.82 grams of the starting sulfide (4.4 mm) were dissolved in 20 mL of dichloromethane and 17 mL of a 0.5 N solution of methanesulfonic acid in dichloromethane. 1.15 grams of commercial MCPBA (60–80% pure) were added at 0°, and the solution was stirred for thirty minutes. The reaction mixture was diluted with ethyl acetate and extracted with saturated sodium bicarbonate. The organic layers were dried over sodium sulfate, concentrated, and purified by column chromatography in a gradient of 75% ethyl acetate/hexane to 5% methanol/ethyl acetate to give 1.22 grams of the desired sulfoxide and 0.4 grams of the corresponding sulfone.

EXAMPLE 14

Synthesis of compounds 300, 301, 302, 304, and 760.

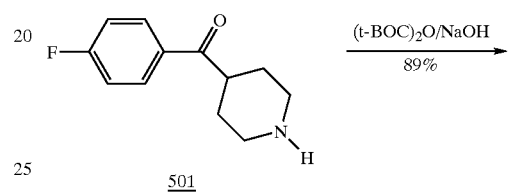

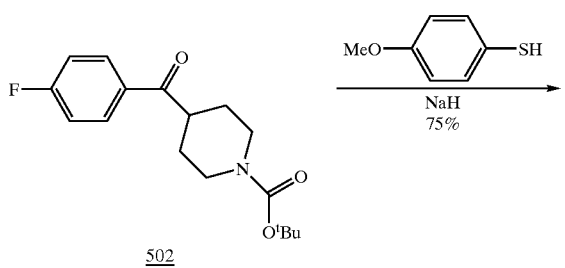

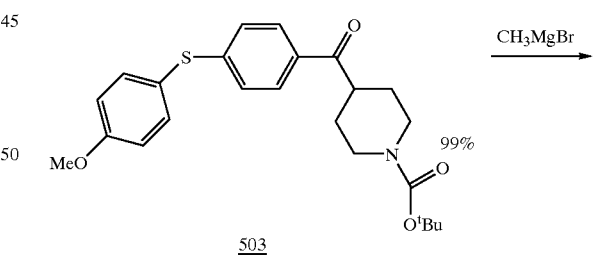

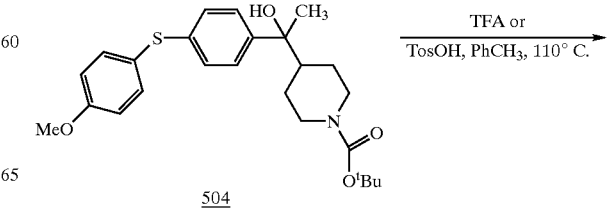

-continued

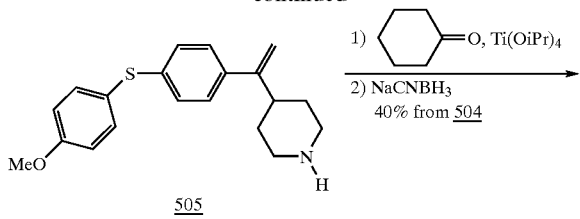
505

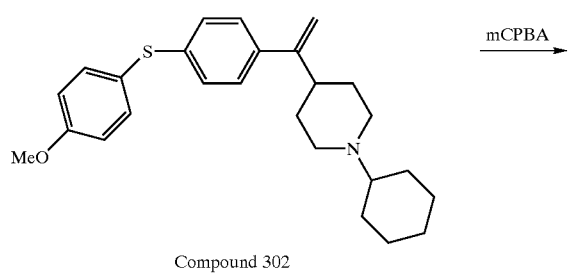
Compound 302

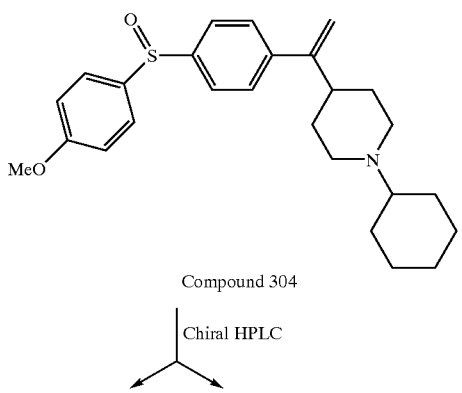
Compound 304

| Chiral HPLC

Compound 300   Compound 301

Step 1

To a stirred mixture of 501 (5.0 g) in 50 ml of aqueous NaOH (20% w/w) was added, at 0° C., Di-tert-butyloxy dicarbonate (3.4 g, 1.2 eq.) dissovled in 50 ml of diethyl ether. The cooling bath was removed and the mixture was stirred at room temperature for 2 hours. Two phases were separated and the aqueous phase was extracted with 2×50 ml of ethyl acetate. The combined organic phases were dried over $Na_2SO_4$, filtered and concentrated to give a crude product. Purification by flash chromatography on silica gel (10% EtOAc-Hex.) afforded 3.5 g (89%) of 502 as a white solid (m.p.=89–90° C.).

Step 2

NaH (460 mg, 60% in mineral oil) was washed with dry hexanes and was stirred with 8 ml of dry DMF. To this mixtue was added 4-methoxythiophenol by syringe. The mixture was stirred at RT for 20 min. while the slurry became a clear solution. Compound 502 dissolved in 8 ml of DMF was added dropwise and the mixture was stirred at room temperature over night. Water (80 ml) was added and the mixture was extracted with 3×100 ml of EtOAc. The combined organic phases were dried over $Na_2SO_4$, filtered and concentrated to give a crude. Purification by flash chromatography on silica gel (20% EtOAc-Hex.) afforded 3.6 g (74%) of 503 as a white solid (m.p.=105–107° C.).

Step 3

To a solution of 503 (1.5 g) in 40 ml of dry THF at 0° C., was added MeMgBr (1.15 ml, 3.0 M in ether). The mixture was stirred at 0° C. for 1 h. and was quenched with 20 ml of a 10% $KHSO_4$. The aqueous phase was extracted with 2×50 ml of ethyl acetate. The combined organic phases were dried over $Na_2SO_4$, filtered and concentrated to give a crude. Purification by flash chromatography on silica gel (30% EtOAc-Hex.) afforded 1.3 g (96%) of 504 as a solid, mp 129–130°.

Step 4

At 0° C., 1.3 g of 504 was dissolved in a mixture of 5 ml TFA and 15 ml $CH_2Cl_2$. The cooling bath was removed and the mixture was stirred at RT for 2 h, quenched with saturated bicarbonate at 0° C., and the aqueous layer extracted with EtOAc. The combined organic phases were dried over $Na_2SO_4$, filtered and concentrated to give a white solid compound 505 which was used in the next step without further purification.

Step 5

The white solid from step 4 was dissolved in 10 ml methylene chloride and to this solution was added 350 mg of cyclohexanone followed by 1.3 g of titanium (IV) iso-propoxide. The mixture was stirred at RT over night. At 0° C., 440 mg of $NaCNBH_3$, dissolved in 2 ml of methanol was added and the mixture was stirred at RT for an additional 3 h. The mixture was quenched with water and extracted with EtOAc. The combined organic phases were dried over $Na_2SO_4$, filtered and concentrated to give a crude product. Purification by flash chromatography on silica gel (100% EtOAc) afforded 0.5 g (40%) of Compound 302 as a white solid. The solid was dissolved in ethyl acetate, and treated with 2–3 equivalents of ethereal dry HCl. The mixture was evaporated to dryness in vacuo to give the hydrochloride, m.p. 227–30°.

Step 6

To a stirred solution of 350 mg of compound 302 in 60 ml EtOAc and 60 ml $CH_2Cl_2$ were added 1.7 ml of $MeSO_3H$ (0.5 M in $CH_2Cl_2$), followed by 262 mg of mCPBA (50–60%) at −40° C. The mixture was allowed to reach 0° C. and was quenched with saturated bicarbonate solution (100 ml). The mixture was extracted with 3×100 ml of EtOAc. The combined organic phases were dried over $Na_2SO_4$, filtered and concentrated to give a crude product. Purification by flash chromatography on silica gel (15% EtOH-EtOAc) afforded 0.2 g (55%) of compound 304 as a white solid.

HPLC Separation of compound 304 on a Chiralcel OJ column; (Chiral Technologies, Inc., Exton, Pa.):

Compound 304 was separated on a 100–200 mg scale under the following conditions:
Solvent system: 0.1% diethyl amine/3% ethanol/hexane
Flow rate: 160 ml/min
Retention Time:
70 min for enantiomer A (compound 300, mp=141–142)
90 min for enantiomer B (compound 301, mp=141)

Synthesis of Compound 760:

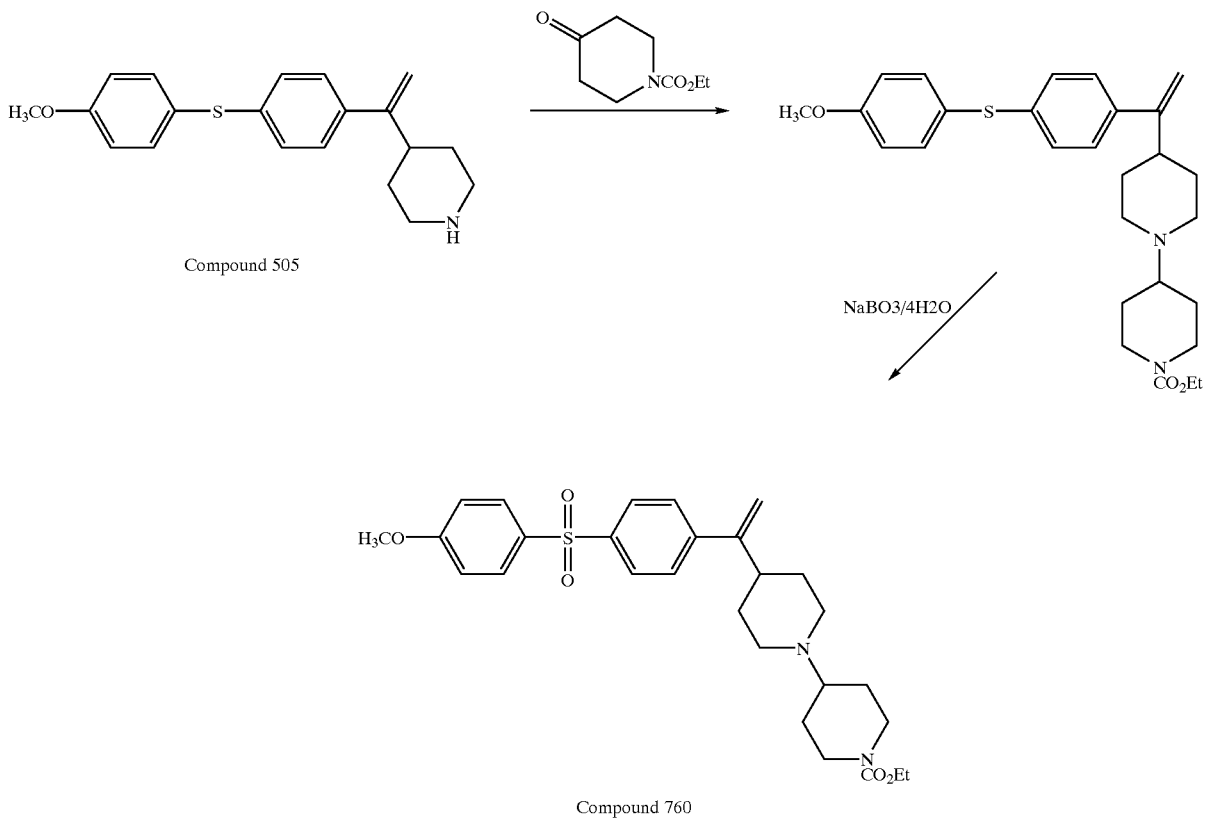

Compound 505

Compound 760

Compound 505 (0.375 g, 1.15 mmol) and 4-carboethoxycyclohexanonone (0.294 g, 1.72 mmol) were dissolved in 6 mL of $CH_2Cl_2$. The reaction mixture was then cooled to 0° C. followed by addition of Ti(i-PrO)$_4$ (1.3 mL, 4.42 mmol). The reaction mixture was stirred at room temperature overnight, when TLC indicated there was no starting material. To the reaction mixture was slowly added a solution of NaCNBH$_3$ (0.364 g, 5.8 mmol) in MeOH (2 mL). The reaction mixture was then stirred at room temperature for 2 h. The reaction was quenched by addition of 50 mL of 1N NaOH followed by 50 mL of ethyl acetate. The reaction mixture was stirred at room temperature for 1 h then was extracted with ethyl acetate (50 mL×3). The organic layer was dried with NaHCO$_3$. Solvent was removed and the residue was separated on a silica gel column (5% methanol/ $CH_2Cl_2$) to afford the sulfide (0.46 g, 83% yield) as an oil.

The sulfide (0.038 g, 0.08 mmol) was dissolved in 2 mL of HOAc followed by addition of NaBO$_3$/4H$_2$O (0.037 g, 0.24 mmol). The reaction mixture was stirred at room temperature overnight, when TLC indicated there was no starting material. To the reaction mixture was then added 1N NaOH until basic. The reaction mixture was extracted with ethyl acetate (20 mL×3). The organic layer was dried with NaHCO$_3$. Solvent was removed and the residue was separated on a silica gel column (5% methanol/CH$_2$Cl$_2$) to afford Sch 65546 (0.007 mg, 17% yield) as an oil.

EXAMPLE 15

Synthesis of Compound 306

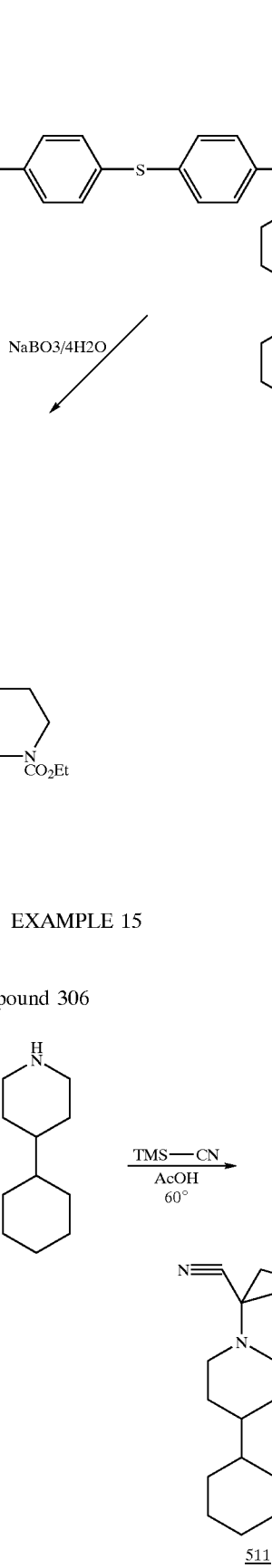

511

Preparation of 511

To a solution of 25 mmol of cyclohexanone in 20 ml of acetic acid is added 62.5 mmol of cyclohexylpiperazine. The system is blanketed with $N_2$ and 31.3 mmol of TMS-cyanide, is added. The solution is then heated at 60° C. under $N_2$ for approximately 20 hours. Acetic acid is removed on a rotary evaporator and the residue treated with 100 ml of water. This is extracted with EtOAc, (3×, 50 ml). Organic layers are washed with 100 ml. of water, dried with $Na_2SO_4$ and evaporated to give the crude product as an oil which is purified by column chromatograpy using 100:3:1 $CH_2Cl_2$:EtOH:$NH_4OH$ as eluant. An oil was obtained, 10 g of which was dissolved in 100 ml $CH_2Cl_2$ and 50 ml water, then basified to pH 8 with $K_2CO_3$. The organic layer was dried with $Na_2SO_4$ and evaporated to obtain a light yellow powder, 6.6 g.

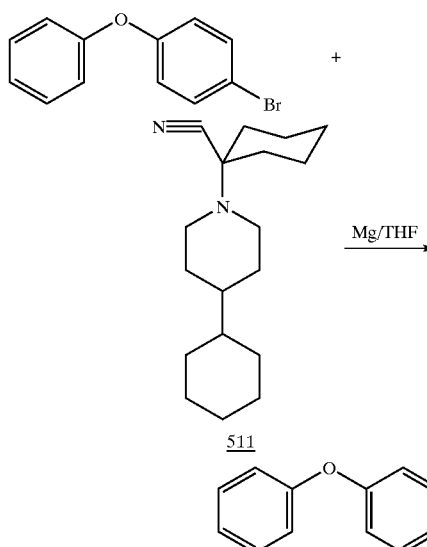

Preparation of Compound 306

In a three necked round bottomed flask is placed 5.4 mmol of Mg and the flask is fitted with a condenser, dropping funnel and nitrogen inlet. The system is flame dried under nitrogen. Bromodiphenyylether (5.4 mmol), is dissolved in anhydrous THF, (10 ml), and added drop-wise. Addition of a drop of ethylene dibromide, iodine and occasional warming may be necessary to initiate Grignard formation. Once initiated the mixture is heated at reflux until all the Mg dissolves. Next, 1.8 mmol of cyanoamine 511 as a solution in 5 ml of dry THF is added, reflux is continued, and the reaction monitored by TLC.

The reaction mixture is cooled to room temperature and quenched by addition of a saturated $NH_4Cl$ solution, (10 ml). This is diluted with 10 ml of water and extracted with 15 ml EtOAc, (3×). The organic extracts are dried with $Na_2SO_4$ and evaporated to give the crude product as an oil which is purified by column chromatography using ether/EtOAc as eluant. 370 ml of clear colorless oil was obtained.

The dimaleate salt was prepared by dissolving the oil in 10 ml of EtOAc and treating with 200 mg of maleic acid. A white powder was obtained (510 mg, mp=144–146).

EXAMPLE 16

Synthesis of Compound 303

Example 15 is repeated except in place of cyclohexanone there is used a compound of the formula

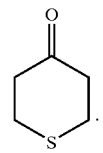

Compound 303 is obtained as a di-maleate:

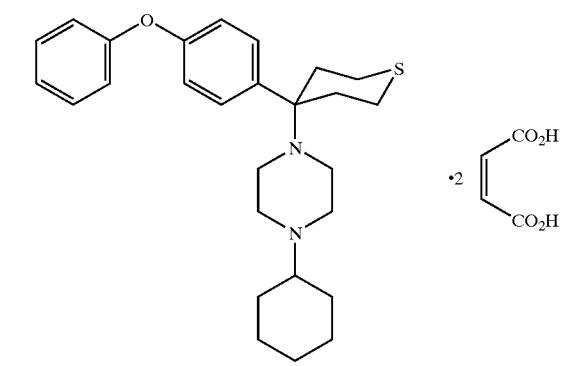

Compound 303
mp: 137–139

EXAMPLE 17

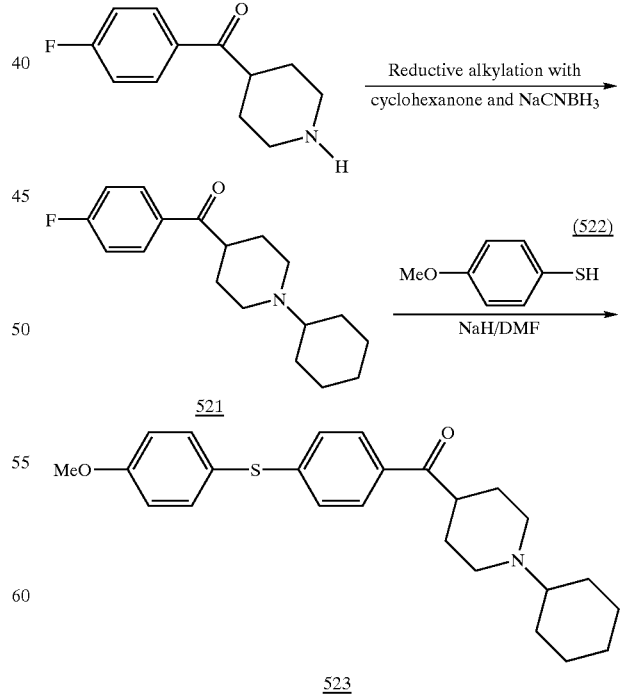

NaH (334 mg., 60% oil suspension) was washed with 15 ml of hexane, then stirred with 5 ml of DMF. Compound 522

(1.03 ml) was added without solvent, the mixture stirred at room temperature for 20 min, a solution of 521 (2.42 g obtained by reductive alkylation) in 1.7 ml of hot DMF added, and the resulting mixture stirred at room termperature for two days. The mixture was quenched with water, and extracted with ethyl acetate. The extracts were purified by flash chromoatography over $SiO_2$ to give 3.0 g of product 523, mp 128–9°.

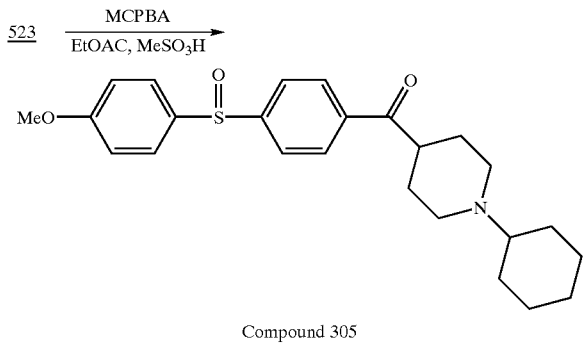

Compound 305 m-Chloroperbenzoic acid (MCPBA, 81 mg) was added to a solution of 523 (105 mg) and $MeSO_3H$ (0.5 M in $CH_2Cl_2$, 1.0 ml) in 50 ml of ethyl acetate at −40°. Sufficient $CH_2Cl_2$ was added at this temperature to effect dissolution of solids, and the mixture allowed to warm to room temperature. The mixture was quenched with excess $NaHCO_3$ solution, and extracted with ethyl acetate. The extracts were concentrated and purified by preparative thin-layer chromatography, developing with 20% ethanol-ethyl acetate to give Compound 305 N-oxide. This material was dissolved in $CH_2Cl_2$, $CS_2$ added, and the resulting mixture stirred for 3 hrs. at room temperature. Evaporation of volatiles and purification of the residue by preparative TLC as above gave Compound 305, mp 125°.

EXAMPLE 18

(Process F)
Preparation of Compounds 3–10 Shown in Process F. where R is 4-methoxyphenyl, R3 and R4 are H, R1 is (S)—$CH_3$, and R27 is (R)—$CH_3$ and
  Preparation of Compound (3)
  To an ice cooled solution of trifluoroacetic anhydride (19 mL) in $CH_2Cl_2$ (100 mL) add over 15 min (S)-(−)-α-methylbenzylamine (12.2 9) in $CH_2Cl_2$ (25 mL) with stirring, then stir at RT for 1 h. Cool in ice and add methanesulfonic acid (40 mL) then powdered dibromodimethyl hydantoin (15 g). Stir till dissolved, then store for 20 h at RT, protected from light. Add to a stirred solution of $NaHSO_3$ (5 g) in ice-$H_2O$ (100 mL), stir 5 min., separate, extract with $CH_2Cl_2$, wash the combined organics with $H_2O$ and dry ($MgSO_4$). Filter on 30 g flash silica and elute with $CH_2Cl_2$ (300 mL). Evaporate the total eluates to dryness, add $Et_2O$ (100 mL), stir 10 min. and add hexanes (500 mL). Stir 0.5 h, filter, wash with hexanes and dry to obtain the 4-bromocompound (12.3 g) as white crystals.
  Mp: 153–155°. Mass spectrum: MH+=296/298.
  Preparation of Compound (4)
  Cool a solution of compound (3) (11.95 g) in dry THF (160 mL) to −70° under $N_2$ and add methyllithium (1.4M in $Et_2O$, 28.8 mL). Stir 5 min. then add n-butyllithium (2.5M in hexanes, 17 mL). Stir 5 min. then add 4-methoxybenzenesulfonyl fluoride (16 g). remove the cooling bath, stir for 0.5 h, add 1N-HCl aq. (200 mL) and exteract with $CH_2Cl_2$. Wash with $H_2O$, dry ($MgSO_4$) and filter on a 15 g pad of flash silica gel, wash with 5% $Et_2O$—$CH_2Cl_2$ and evaporate. Recrystallise with $Et_2O$-hexanes and dry to give the sulfone (13.4 g) as off-white crystals.
  Mp: 97–100°. Mass specrtum: MH+=388.
  Preparation of Compound (5)
  Reflux on a steam bath for 2 h a mixture of compound (4) (17.5 9) and NaOH (6 g) in $H_2O$ (15 mL) and ethanol (120 mL). Cool, add $H_2O$ and extract with $CH_2Cl_2$. Dry over $K_2CO_3$, filter and evaporate. Triturate with $Et_2O$-hexanes till solid, filter and dry to afford the amine (10.4 g), as a white solid.
  Mp: 113–115°. Mass spectrum: MH+=292
  Preparation of Compound (6)
  To solution of compound (5) (1.46 g) in $CH_2Cl_2$ (20 mL) and potassium carbonate (2 g) in $H_2O$ (10 mL) add ethyl (S)-lactate trifluoromethanesulfonate (1.1 g) and stir at RT for 5 h. Wash with water, dry ($MgSO_4$), evaporate and chromatograph on flash silica gel, eluting with a 0–15% gradient of $Et_2O$ in $CH_2Cl_2$. Evaporate the pure fractions and triturate in hexanes to obtain the crystalline ester (1.90 g)
  Mp: 56–58°. Mass spectrum: MH+=392.
  Preparation of Compound (7)
  Reflux a mixture of compound (6) (1.73 g), acetonitrile (15 mL), anhydrous sodium carbonate (1.5 g) and ethyl iodoacetate (1.4 mL) for 48 h., work up in $H_2O$—$CH_2Cl_2$, dry ($MgSO_4$) and evaporate. Chromatograph on silica, using a 0 to 10% gradient of $Et_2O$ in $CH_2Cl_2$ and evaporate appropriate pure fractions to separately obtain the solid product (1.46 g) and recovered starting aminoester (0.53 g).
  Mp: 69–71°. Mass spectrum: MH+=478.
  Preparation of Compound (8)
  Stir lithium aluminum hydride (0.45 g) in THF (15 mL) under $N_2$ with ice cooling and add over 2–3 min. a solution of diester (7) (1.30 g) in THF (25 mL). Stir in ice for 0.5 h., add EtOAc (5 mL) dropwise, then add the solution to stirred, ice cooled 2N-NaOH solution (50 mL). Separate, extract the aq. with 3:1 $Et_2O$—$CH_2Cl_2$, combine, dry and evaporate the organics and triturate with a little $Et_2O$ to obtain the diol as a white powder (0.88 g).
  Mp: 123–125°. Mass spectrum: MH+=394.
  Preparation of mixture (10)
  Reflux a mixture of compound (8) (0.125 g), thionyl chloride (0.25 mL) and 1,2-dichloroethane (5 mL) for 1.5 h., evaporate, co-evaporate with 3 mL dichloroethane and dry at high vacuum to obtain the mixture of dichlorocompounds as a pale yellow foam, suitable for use in the next step.
  Preparation of compound numbers 730 and 803
  These compounds are examples of compounds 11 and 12 as shown for process f.
  Convert diol (0.125 g) to the dichlorides as described above, then reflux this product for 2 h. in acetonitrile (2.5 mL) with trans-4-aminocyclohexanol hydrochloride (0.32 g), sodium iodide (0.5 g) and diisopropylethylamine (0.6 mL). Cool, and partition in $H_2O$—$CH_2Cl_2$. Dry and evaprorate the organic phase, and subject the residue to preparative TLC, eluting with acetone. Extract the separated bands with 1:1 $CH_2Cl_2$-MeOH, evaporate and dry at high vacuum to obtain the free bases as foams.
  The less polar band (0.056 g) is compound no.730. Dissolve this in $CH_2Cl_2$ (2 mL) and add to stirred $Et_2O$ (15 mL) containing 4M HCl-dioxan (0.4 mL). Centrifuge, wash by suspension-centrifugation in ether (2×15 mL) and dry under $N_2$ to obtain the dihydrochloride as a white powder.
  Mp: 195–205°, with decomposition. Mass spectrum: MH+=473.

The more polar band (0.076 g) is compound 803. Convert this to the hydrochloride as above.

Mp: 215–225 C., with decomposition. Mass Spectrum MH+=473

EXAMPLE 19

(Process G)

Preparation of compound 667 and 656

Step 1(a)

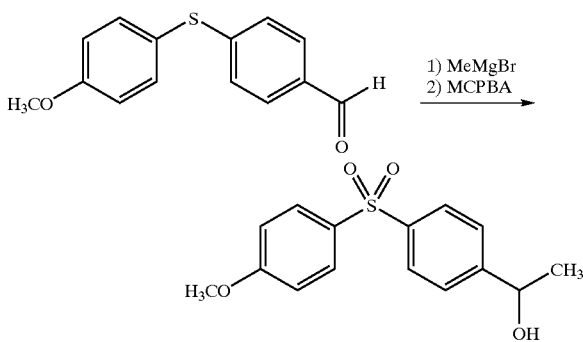

A solution of the aldehyde (Compound VII' of preparation 4, Process C, 4.9 g, 0.02 mol) in 50 mL THF was cooled in an ice water bath and methylmagnesium bromide (8.5 mL, 3.0 M) was slowly added. After 0.5 h the temperature was warmed to room temperature where stirring was continued for 16 h. After dilution with ethyl acetate and addition of water the organic layer was washed with water, brine, and concentrated. Drying under vacuum produced a yellow oil (5.1 g) which was used without further purification.

A dichloromethane (150 mL) solution of the sulfide was cooled in an ice water bath where MCPBA (11.7 g, 60%) was added. After stirring for 1 h the temperature was warmed to room temperature and stirred for 16 h. After diluting with ethyl acetate the reaction was washed with 10% sodium carbonate, water, and brine. The solution was concentrated and purified by chromatography with ethyl acetate to the sulfone alcohol.

To a clear pale yellow solution of the p-anisylthioacetophenone 1 (0.8 g; 3.1 mmol) in anhydrous tetrahydrofuran (5 mL) was added (S)-oxaborolidine catalyst 2 (0.168 g; 0.6 mmol) and stirred at room temperature for 15 minutes. A solution of borane-methyl sulfide in tetrahydrofuran (2M from Aldrich Chemicals; 1.86 mmol; 0.93 mL) was added dropwise over 6 minutes to the solution of ketone 1 and catalyst 2 at room temperature. After 10 minutes of stirring, thin layer chromatography (TLC) showed absence of starting material and formation of a new, slightly more polar spot. The reaction was quenched by adding methanol (5 mL) and stirring for 15 minutes. Volatiles were removed on the rotary evaporator and the residue was dissolved in methylene chloride (50 mL). The organic extract was washed with water, 1N.HCl, water, 10% $NaHCO_3$, brine and dried over magnesium sulfate. Concentration of the organic extract gave the carbinol 3 as a clear pale yellow oil (0.76 g; yield=94%).

HPLC: AS-Column (5% i-PrOH in Hexanes); $R_t$~19 min; R:S=97:3 (94% ee/R-Alcohol)

$[\alpha]D=+26.1$ (c=0.1; $CHCl_3$)

A clear pale yellow solution of 3 (0.76 g; 2.92 mmol) in anhydrous dichloroethane (8 mL) at room temperature was treated sequentially with solid $NaHCO_3$ (0.6 g, 7 mmol) and solid meta-chloroperoxybenzoic acid (1.1 g; 6.43 mmol). The flask was fitted with a reflux condensor and the reaction mixture was heated to reflux. TLC at the end of 8 hours showed absence of 3 and formation of a more polar spot. Reaction mixture was allowed to cool to room teperature. The organic layer was decanted away from the white precipitate of sodium salts, washing the solid residue with methylene chloride (2×20 mL). The combined organic extract was washed with water, 10% $Na_2S_2O_3$ solution, water, 10% $NaHCO_3$ solution and brine. Dried the organic layer over magnesium sulfate and concentrated to obtain ~0.8 g of a pale yellow solid. Flash silicagel chromatography (20% $EtOAc-CH_2Cl_2$) gave 0.75 g (88% from 1) of sulfone as a white solid, mp: 125–126° C. $[\alpha]D=+22.1$ (C=0.095; $CHCl_3$)

Step 1(b)

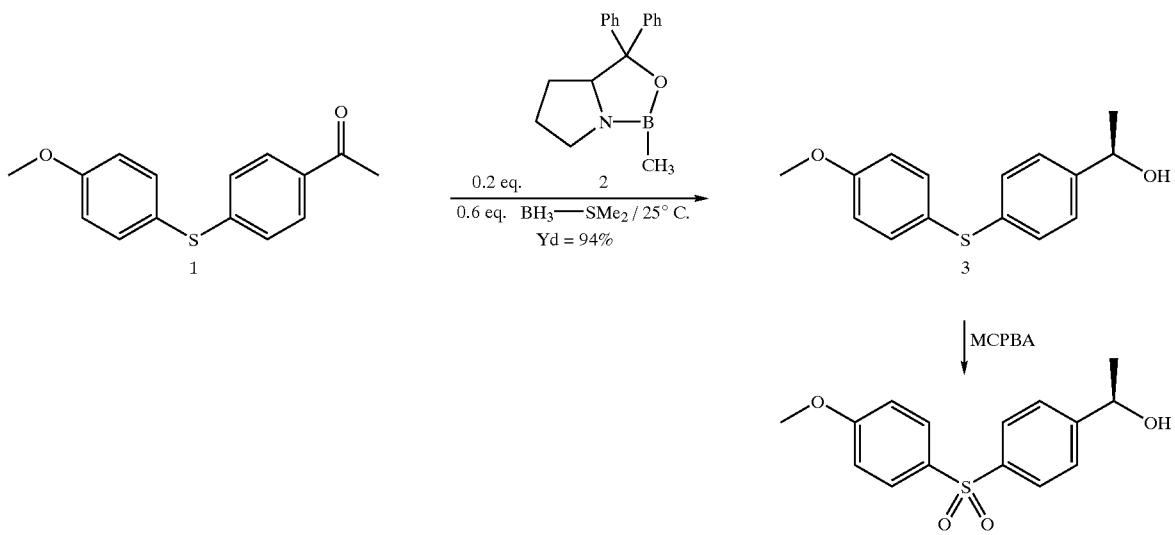

Step 2:

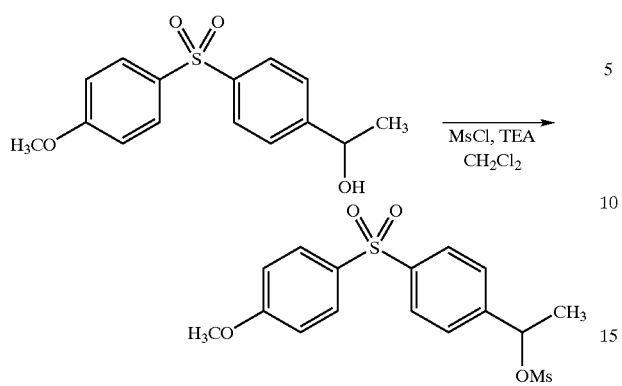

To a suspension of the alcohol (4.0 g, 13.6 mmol) in dichloromethane (30 mL) was added triethylamine (2.75 g, 27.2 mmol). The mixture was cooled in an ice/water bath and methanesulfonyl chloride (1.87 g, 16.3 mmol) was added dropwise. After 1 h the mixture was diluted with dichloromethane and washed with water, 2% HCl, water, 10% NaHCO$_3$ and brine. After drying over sodium sulfate the solvent was evaporated to afford the crude product as a gum. It was used without further purification.

Step 3:

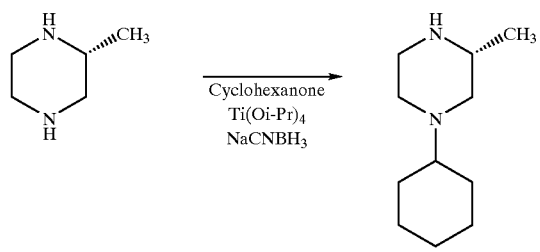

2-(R)-Methylpiperazine (30 g, 0.3 mol) and cyclohexanone (32 g, 0.33 mol) were dissolved in methylene chloride (60 mL) and cooled in an ice/water bath where titanium (IV) isopropoxide (93 g, 0.33 mol) was added dropwise. Stirring was continued for 1 h at $_0°$ C. then at room temperature for 16 h. A solution of sodium cyanoborohydride (21 g, 0.33 mol) in methanol (200 mL) was added with stirring continued for 24 h. The mixture was diluted with 1 L ethyl acetate and stirred with 400 mL 10% NaOH for 1 h. The aqueous solution containing a white precipitate was discarded. The organic layer was washed with water and brine, followed by concentration on a rotary evaporator. The residue purified by flash chromatography with 25:1 CH$_2$Cl$_2$/MeOH (saturated with aqueous ammonia), yield=50%.

Step 4

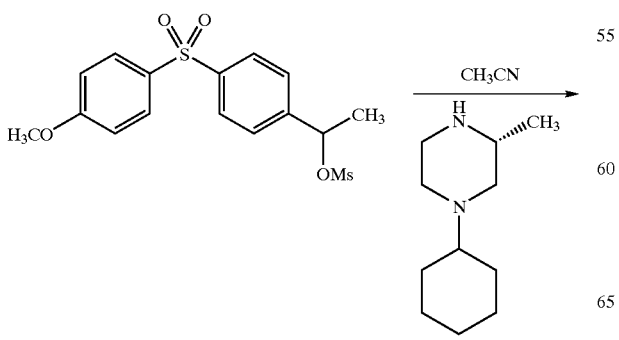

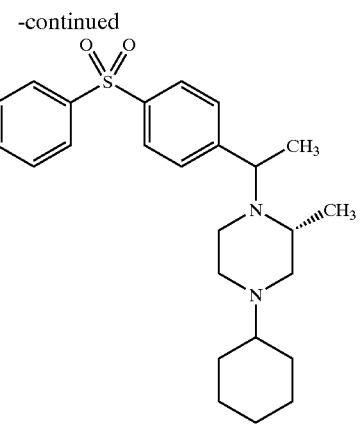

The mesylate from step 2 (4.8 g, 13 mmol) and 1-cyclohexyl-3(R)-methylpiperazine (3.5 g, 19.4 mmol) were dissolved in 40 mL CH$_3$CN and heated to 60 C. where stirring was continued for 24 h, then refluxed for 8 h. The solvent was removed and the residue dissolved in ethyl acetate. The organic layer was washed with 10% sodium carbonate and brine. The solvent was evaporated and the residue chromatographed with 4:1 dichloromethane/acetone. When step 1a is used, two diastereomers (compounds 656 and 667) were collected in a 1:1 ratio (656: R$_f$ 0.40, ethyl acetate: Anal. calc. C, 68.39; H, 7.95; N, 6.13; S, 7.02; found C, 68.01; H, 8.02; N, 6.09; S, 7.05. 667: R$_f$ 0.30, ethyl acetate: found C, 68.06; H, 8.08; N, 6.18; S, 6.84). When step 1b is used starting with the (S)-oxaborolidine shown, then the product is 656 while (R)-oxaborolidine catalyst gives 667.

Isomer A

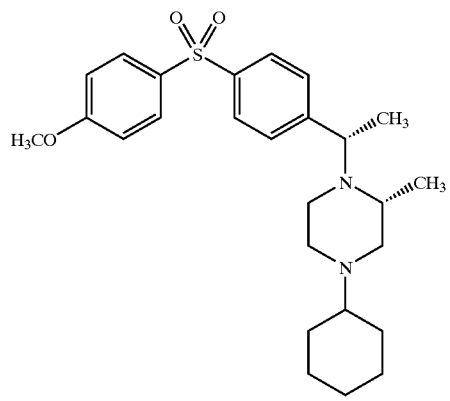

Compound 656

Isomer B

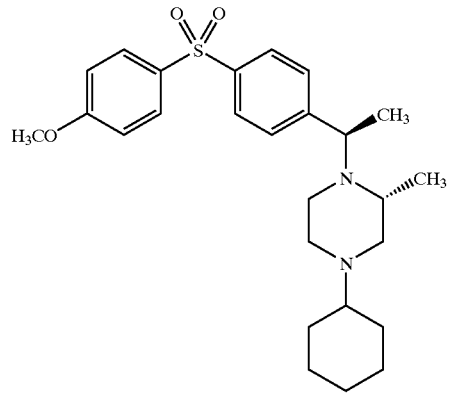

Compound 667

By appropriate choice of starting materials, the following compounds were prepared. In these tables the following notes apply.

t-BOC means t-butloxycarbonyl. The compound numbering is not consecutive. A (+) or (−) after a compound number indicates the optical rotation of the stereoisomer for which data is given. "IsoA" or "IsoB" after a compound number indicates an assignment of A or B to different stereoisomers of a compound having the same structural formulas without regard to optical rotation. When the chiral atom has been identified, "isoA" or isoB" is listed after a substituent for that atom. NBA is nitrobenzyl alcohol, G/TG is glycerol/thioglycerol. Chex means cyclohexyl.

Compounds having the formula

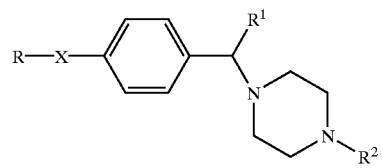

| # | R | X | $R^1$ | $R^2$ | Mass Spectrum or MP |
|---|---|---|---|---|---|
| 1 | $C_6H_5$ | S | $CH_3$ | $CH_3$ | MP = 254–256 (di-HCl) |
| 2 | $C_6H_5$ | $SO_2$ | $CH_3$ | $CH_3$ | MP = 226–230 (di-HCl) |
| 3 | $C_6H_5$ | SO | $CH_3$ | $CH_3$ | MP = 240–242 (di-HCl) |
| 4 | $C_6H_5$ | SO | $CH_3$ | H | MP = 80–85 (dimaleate) |
| 5 | $C_6H_5$ | S | $CH_3$ | H | MP = 227–229 (di-HCl) |
| 6 | $C_6H_5$ | $SO_2$ | $CH_3$ | H | MP = 180–220 (di-HCl hydrate) |
| 7 | $C_6H_5$ | $SO_2$ | $CH_3$ | $(CH_2)_2OH$ | MP = 236–238 (di-HCl) |
| 8 | 4-Cl—$C_6H_4$ | $SO_2$ | $CH_3$ | $(CH_2)_2OH$ | MP = 242–244 (di-HCl) |
| 9 | $C_6H_5$ | O | $CH_3$ | $(CH_2)_2OH$ | $Cl(CH_4)$:327(M + 1), 309, 197 |
| 10 (+) | $C_6H_5$ | $SO_2$ | $CH_3$ | $(CH_2)_2OH$ | FAB-NBA-G/TG-DMSO: 375(M + 1) |
| 11(−) | $C_6H_5$ | $SO_2$ | $CH_3$ | $(CH_2)_2OH$ | FAB-NBA-G/TG-DMSO: 375(M + 1) |
| 12 | 2-pyridyl | O | $CH_3$ | $CH_3$ | MP = 172–175 (Dimaleate) |
| 13 | $C_6H_5$ | O | $CH_3$ | $(CH_2)_2O(CH_2)_2OH$ | EI: 370 (M+), 197, 99 |
| 14 | $C_6H_5$ | $SO_2$ | i-Pr | $(CH_2)_2OH$ | EI: (M + 1)402, 359, 329, 128, |
| 15 | $C_6H_5$ | $SO_2$ | $CH_3$ | 2-$CH_3O$—$C_6H_4$ | FAB-NBA-G/TG-DMSO: 437 (M + 1) |
| 16 | $C_6H_5$ | $SO_2$ | $CH_3$ | cyclohexyl | $Cl(CH_4)$: (M + 1) 413 |
| 17 | $C_6H_5$ | $SO_2$ | i-Pr | cyclohexyl | $Cl(CH_4)$: (M + 1) 441, 397, 299 |
| 18 | 4-$CH_3C_6H_4$ | $SO_2$ | $CH_3$ | cyclohexyl | EI: 427(M + 1), 383, 167 |
| 19 | $C_6H_5$ | $SO_2$ | $CH_3$ | $C_6H_5$ | SIMS-NBA-G/TG-DMSO: 407 (M + 1), 232 |
| 20 | 3-pyridyl | O | $CH_3$ | $(CH_2)_2OH$ | MP = 165–168 (Dimaleate) |
| 21 | 3-pyridyl | O | $CH_3$ | cyclohexyl | MP = 219–222 (Dimaleate) |
| 22 | 3-pyridyl | S | $CH_3$ | $(CH_2)_2OH$ | MP = 155–158 (Dimaleate) |
| 23 | 3-pyridyl | S | $CH_3$ | cyclohexyl | MP = 157–159 (Dimaleate) |
| 24 | 2-$CH_3$-4-pyridyl | O | $CH_3$ | $(CH_2)_2OH$ | MP = 165–166 (Dimaleate) |
| 25 | 2-$CH_3$-4-pyridyl | O | $CH_3$ | cyclohexyl | MP = 90–91 |
| 26 | $C_6H_5$ | O | $CH_3$ | cyclohexyl | EI: 364 (M+), 349, 197, 167 |
| 27 | $C_6H_5$ | $SO_2$ | $C_6H_5$ | cyclohexyl | FAB-NBA-G/TG-DMSO: (M + 1) 475, 335, 307, 257 |
| 28 | $C_6H_5$ | $SO_2$ | i-Pr | $(CH_2)_3OH$ | FAB-G/TG-DMSO: (M + 1) 417, 373, 315, 273 |
| 29 | $C_6H_5$ | $SO_2$ | i-Pr | $(CH_2)_2O(CH_2)_2OH$ | FAB-NBA-G/TG-DMSO: (M + 1) 447, 404, 329, 315 |
| 30 | $C_6H_5$ | $SO_2$ | n-Bu | cyclohexyl | MP = 217–220 |
| 31 | 4-Cl—$C_6H_4$ | $SO_2$ | i-Pr | cyclohexyl | MP = 134–137 (dec) |
| 32 | 4-$CH_3$—$C_6H_4$ | $SO_2$ | i-Pr | cyclohexyl | MP = 208–210 |
| 33 | $C_6H_5$ | $SO_2$ | $CH_3$ | 4-$NO_2$—$C_6H_4$ | FAB-NBA-G/TG-DMSO: 452(M + 1) |
| 34 | $C_6H_5$ | $SO_2$ | $CH_3$ | $(CH_2)_3OH$ | FAB-NBA-G/TG-DMSO: 389(M + 1) |
| 35 | 4-$CH_3$—$C_6H_4$ | $SO_2$ | $CH_3$ | 2,3-$(CH_3)_2$—$C_6H_3$ | $Cl(CH_4)$: 449(M + 1), 191, 148 |
| 36 | 4-Cl—$C_6H_4$ | $SO_2$ | $CH_3$ | cyclohexyl | FAB-NBA-G/TG-DMSO: 447(M + 1) |
| 37 | 3-pyridyl | O | i-Pr | cyclohexyl | MP = 150–153 (Difumarate) |
| 38 | 4($CH_3O$)$C_6H_4$ | $SO_2$ | i-Pr | cyclohexyl | $Cl(CH_4)$: (M + 1)471, 427, 305, 289, 144, |
| 39 | 4-Cl—$C_6H_4$ | $SO_2$ | $C_6H_5$ | cyclohexyl | FAB-NBA-G/TG-DMSO: 510 (M + 1), 399, 341 |
| 40 | 4-Cl—$C_6H_4$ | $SO_2$ | n-Bu | cyclohexyl | FAB-NBA-G/TG-DMSO: 489 (M + 1), 349, 314 |
| 41 | 4-(t-Bu)$C_6H_4$ | $SO_2$ | i-Pr | cyclohexyl | FAB-NBA-G/TG-DMSO: 497 (M + 1), 453, 371, 329, 301, 223 |
| 42 | 3-Cl—$C_6H_4$ | $SO_2$ | $CH_3$ | cyclohexyl | $Cl(CH_4)$: 447 (M + 1) |
| 43 | $C_6H_5$ | $SO_2$ | cyclohexyl | cyclohexyl | $Cl(CH_4)$: 481 (M + 1), 341, 315, 219, 169, 167, 111, 79 |
| 44 | $C_6H_5$ | $SO_2$ | CN | cyclohexyl | $Cl(CH_4)$: 424 (M + 1), 397, 328, 286, 258, 233, 197, 169, 167, 111, 79 |
| 45 | $C_6H_5$ | O | $CH_3$ | $(CH_2)_2$—O-t-BOC | FAB-SIMS-NBA-G/TG-DMSO: 411 (M + 1), 308, 197 |

-continued

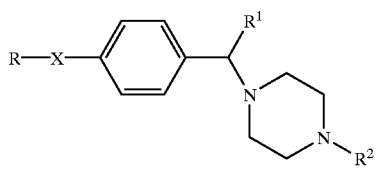

| # | R | X | R$^1$ | R$^2$ | Mass Spectrum or MP |
|---|---|---|---|---|---|
| 46 (+) | 4-CH$_3$—C$_6$H$_4$ | SO$_2$ | CH$_3$ | cyclohexyl | EI: 427 (m + 1), 388, 167 |
| 47 (−) | 4-CH$_3$—C$_6$H$_4$ | SO$_2$ | CH$_3$ | cyclohexyl | EI: 427 (m + 1), 388, 167 |
| 48 | C$_6$H$_5$ | O | CH$_3$ | (CH$_2$)$_3$—O-t-BOC | Cl(Isobutane): 425 (M + 1) |
| 49 | 4-t-Bu—C$_6$H$_4$ | SO$_2$ | CH$_3$ | cyclohexyl | Cl(CH$_4$): (M + 1) 469, 456 |
| 50 | 4(CH$_3$O)C$_6$H$_4$ | SO$_2$ | CH$_3$ | cyclohexyl | Cl(CH$_4$): (M + 1) 443, 399, 167, 125 |
| 51 | 4-CH$_3$—C$_6$H$_4$ | SO$_2$ | CN | cyclohexyl | Cl(Isobutane): 438(M + 1), 411, 272, 261, 169 |
| 52 | 2,4-(Cl)$_2$—C$_6$H$_3$ | O | CH$_3$ | cyclohexyl | Cl(Isobutane): 435(M + 2), 434, 433, 314, 312, 267, 265, 195, 169, 167 |
| 53 | 4-CH$_3$—C$_6$H$_4$ | SO$_2$ | CH$_3$ | (CH$_2$)$_2$NHCOCH$_3$ | Cl(CH$_4$): 430 (M + 1), 357 |
| 54 | 4-t-Bu-C$_6$H$_4$ | O | CH$_3$ | cyclohexyl | Cl(Isobutane): 421 (M + 1) 349, 335, 261, 259, 91 |
| 55 | n-Bu | O | CH$_3$ | cyclohexyl | Cl(Isobutane): 345 (M + 1), 177, 169 |
| 56 | 4-CH$_3$—C$_6$H$_4$ | SO$_2$ | CH$_3$ | CH$_2$CONH$_2$ | Cl(CH$_4$): 402 (M + 1) |
| 57 | 2-pyrimidyl | O | CH$_3$ | cyclohexyl | MP = 191–193 (Dimaleate) |
| 58 | 4-CH$_3$-3-pyridyl | O | CH$_3$ | cyclohexyl | MP = 168–170 (Dimaleate) |
| 59 | 4-CH$_3$—C$_6$H$_4$ | SO$_2$ | CH$_3$ | CH$_2$-cyclohexyl | Cl (CH$_4$) : 441 (M + 1) |
| 60 | 3-pyridyl | O | CH$_3$ | CH$_2$-cyclohexyl | MP = 187–189 (Dimaleate) |
| 61 | 2-benzoxazolyl | O | CH$_3$ | cyclohexyl | MP = 165–168 (Maleate) |
| 62 | 3-pyridyl | O | CH$_3$ | CH$_2$CH(OH)C$_6$H$_5$ | MP = 162–164 (Dimaleate) |
| 63 | 3-pyridyl | O | CH$_3$ | bicyclo[2.2.1]hept-2-yl | MP = 168–175 (Dimaleate) |
| 64 | C$_6$H$_5$ | O | CH$_3$ | (CH$_2$)$_2$OCOCH$_2$-tBu | Cl(CH$_4$): 425 (M + 1), 309, 197 |
| 65 | 1-Me-2-imidazolyl | S | CH$_3$ | cyclohexyl | MP = 155–158 (Dimaleate) |
| 66 | 2-pyrimidyl | O | CH$_3$ | cyclopentyl | MP = 178–181 (Dimaleate) |
| 67 | 2-pyrimidyl | O | CH$_3$ | cycloheptyl | MP = 167–171 (Dimaleate) |
| 68 | 2-pyrimidyl | O | CH$_3$ | tetrahydrothiapyran-4-yl | MP = 157–160 (Dimaleate) |
| 69 | 2-pyrimidyl | O | CH$_3$ | 3-Me-2-butenyl | MP = 180–182 (Dimaleate) |
| 70 | 2-pyrimidyl | O | CH$_3$ | 2-cyclohexenyl | MP = 171–174 (Dimaleate) |
| 71 | 2,4-(MeO)$_2$-6-pyrimidyl | O | CH$_3$ | cyclohexyl | MP = 196–199 (Dimaleate) |
| 72 | 4-CF$_3$-2-pyridyl | O | CH$_3$ | cyclohexyl | MP = 178–182 (Dimaleate) |
| 73 | 3-Me-2-butenyl | O | CH$_3$ | cyclohexyl | MP = 194–197 (Dimaleate) |
| 74 | 2-pyrimidyl | S | CH$_3$ | cyclohexyl | MP = 182–184 (Dimaleate) |
| 75 | 4-Me-2-pyrimidyl | S | CH$_3$ | cyclohexyl | MP = 163–165 (Dimaleate) |
| 76 | 3-pyridyl | O | CH$_3$ | 1-azabicyclo[2.2.2]-oct-3-yl | MP = 182–184 |
| 77 | 3,4-(MeO)$_2$—C$_6$H$_3$ | SO$_2$ | CH$_3$ | cyclohexyl | SIMS-NBA-G/TG-DMSO: 473 (M + 1), 399, 337, 305, 273, 214 |
| 78 | 4-Me-2-pyrimidyl | O | CH$_3$ | cyclohexyl | MP = 179–181 (Dimaleate) |
| 79 | 4-HO—C$_6$H$_4$ | O | CH$_3$ | cyclohexyl | Cl(CH$_4$): (M + 1) 381, 287, 241, 213, 195, 167, |
| 80 | 4-Et—C$_6$H$_4$ | O | CH$_3$ | cyclohexyl | Cl(CH$_4$): (M + 1) 393, 377, 253, 225, 195, 169, |
| 81 | 1-piperidyl | CH$_2$ | CH$_3$ | cyclohexyl | Cl(Isobutane): (M + 1) 370, |
| 83 | 4-CH$_3$—C$_6$H$_4$ | SO$_2$ | CH$_3$ | 2-ketocyclohexyl | Cl(CH$_4$): 441 (M + 1), 345, 261 |
| 84 | 4-CH$_3$—C$_6$H$_4$ | SO$_2$ | CH$_3$ | (CH$_2$)$_2$OH | SIMS-NBA-G/TG-DMSO: 389 (M + 1) |
| 85 | 3,5-(CH$_3$)$_2$—C$_6$H$_3$ | O | CH$_3$ | cyclohexyl | EI: (M + 1) 392, 377, 343, 327, 225, 155, |
| 86 | 4-CH$_3$O—C$_6$H$_4$ | O | CH$_3$ | cyclohexyl | Cl(Isobutane): 395 (M + 1), 269, 227, 181, 169 |
| 87 | 2-cyclohexenyl | O | CH$_3$ | cyclohexyl | Cl(Isobutane): 369 (M + 1), 288 |
| 88 | 4-Cl-2-pyrimidyl | O | CH$_3$ | cyclohexyl | MP = 160–161 (Dimaleate) |
| 89 | 4,6-(Cl)$_2$-2-pyrimidyl | O | CH$_3$ | cyclohexyl | MP = 180–182.5 (Dimaleate) |
| 90 | 2,4-(MeO)$_2$-1,3,5-triazin-6-yl | O | CH$_3$ | cyclohexyl | MP = 198–200 (Dimaleate) |
| 91 (−) | 2-pyrimidyl | O | CH$_3$ | cyclohexyl | Cl(CH$_4$): 367 (M + 1), 199, 142 |
| 92 (+) | 3-Cl—C$_6$H$_4$ | SO$_2$ | CH$_3$ | cyclohexyl | Cl(CH$_4$): 449, 447 (M + 1), |
| 93 (−) | 3-Cl—C$_6$H$_4$ | SO$_2$ | CH$_3$ | cyclohexyl | Cl(CH$_4$): 449, 447 (M + 1)1, |
| 94 (+) | 2-pyrimidyl | O | CH$_3$ | cyclohexyl | Cl(CH$_4$): 367 (M + 1), 199, 142 |
| 95 | tetrahydropyran-4-yl | O | CH$_3$ | cyclohexyl | MP = 218–220 (diHCl) |
| 96 | 2,3,5-(Me)$_3$—C$_6$H$_2$ | O | CH$_3$ | cyclohexyl | EI(M + 1): 406, 266, 239, 167 |
| 97 | 4-CH$_3$—C$_6$H$_4$ | SO$_2$ | CH$_3$ | 1-methylbutyl | SIMS-NBA-G/TG-DMSO: 415 (M + 1) |
| 98 | C$_6$H$_5$ | S | CH$_3$ | cyclohexyl | Cl(CH$_4$): 381 (M + 1) |
| 99 | 6-Cl-3-pyridazinyl | O | CH$_3$ | cyclohexyl | MP = 115–117 |
| 100 | 6-MeO-3-pyridazinyl | O | CH$_3$ | cyclohexyl | MP = 123–127 |

-continued

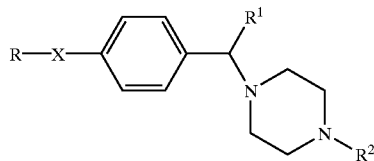

| # | R | X | R¹ | R² | Mass Spectrum or MP |
|---|---|---|---|---|---|
| 101 | 3-pyridazinyl | O | CH₃ | cyclohexyl | MP = 113–115 |
| 102 | 2-MeS-4-pyrimidinyl | O | CH₃ | cyclohexyl | MP = 185–187 (Dimaleate) |
| 103 | 2-thiazolyl | O | CH₃ | cyclohexyl | MP = 184–186 (Dimaleate) |
| 104 | pivaloyl | O | CH₃ | cyclohexyl | Cl(CH₄): 373 (M + 1), 205, 169, 167, 121 |
| 106 | 4-CH₃O—C₆H₄ | S | CH₃ | cyclohexyl | Cl(Isobutane): (M + 1) 411, 243, 169, |
| 107 | 3,4-(MeO)₂C₆H₃ | S | CH₃ | cyclohexyl | Cl(CH₄): (M + 1) 441, 273 164, |
| 108 | C₆H₅ | C(CH₃)(OH) | CH₃ | cyclohexyl | MP = 185–18 Dimaleate |
| 109 | N-morpholinyl | CH₂ | CH₃ | cyclohexyl | Cl(CH₄): 372 (M + 1), 285, 249, 204, 191, 169, 167, 119 |
| 110 | 4-Me-piperazin-1-yl | CH₂ | CH₃ | cyclohexyl | Cl(CH₄): 385 (M + 1), 217, 195, 169, 113, 89 |
| 111 | C₆H₅ | C=CH₂ | CH₃ | cyclohexyl | MP = 189–191 (Dimaleate) |
| 112 | C₆H₅ | CHOH | CH₃ | cyclohexyl | Cl(CH₄): 379 (M + 1), 362, 301, 273, 211, 195, 169, 166 |
| 113 | pyrazinyl | O | CH₃ | cyclohexyl | MP = 110–111 |
| 114 | 2-propynyl | O | CH₃ | cyclohexyl | MP = 173–175 (Dimaleate) |
| 115 | 2-hydroxyethyl | O | CH₃ | cyclohexyl | Cl(CH₄): (M + 1) 333, 317, 205, 165, 121 |
| 116 | benzyl | O | CH₃ | cyclohexyl | EI: (M + 1) 470, 455, 330, 303, 167 |
| 117 | H | CO | CH₃ | cyclohexyl | Cl(CH₄): 301 (M + 1), 385, 195, 169, 135, 119 |
| 118 | CH₃ | CO | CH₃ | cyclohexyl | MP = 158–161 (dimaleate) |
| 119 | 4-CH₃O—C₆H₄ | CHOH | CH₃ | cyclohexyl | EI: 408, 279, 268, 241, 167, 135, 126. |
| 120 | (Me)₂NCO | O | CH₃ | cyclohexyl | Cl(CH₄): (M + 1) 360, 273, 220, 192, 108 |
| 121 | 4-NO₂—C₆H₄ | O | CH₃ | cyclohexyl | SIMS-NBA-G/TG-DMSO: 409 (M + 1), 393, 366, 338, 283, 270, 242, 196, 167 |
| 122 | 4-HO—C₆H₄ | S | CH₃ | cyclohexyl | Cl(CH₄): (M + 1) 397, 257, 229, 195, 167 |
| 123 | 4-CH₃O—C₆H₄ | SO | CH₃ | cyclohexyl | SIMS-NBA-G/TG-DMSO: 427.2 (M + 1), 343 |
| 124 | C₆H₅ | CH=CH | CH₃ | cyclohexyl | MP = 108–111 |
| 125 | 4-CH₃O—C₆H₄ | CO | CH₃ | cyclohexyl | Cl(CH₄): 407 (M + 1), 299, 269, 241, 197, 169, 167, 135. |
| 126 | 3-CH₃O—C₆H₄ | S | CH₃ | cyclohexyl | Cl(CH₄): 411, (M + 1), 271, 245, 243, 195, 169, 166. |
| 127 | 4-Br-2,3,5,6-tetrafluoro-phenyl | O | CH₃ | cyclohexyl | Cl(CH₄): 515 (M + 1), 437, 435, 271, 269, 191, 167. |
| 128 | 3-CH₃O—C₆H₄ | SO | CH₃ | cyclohexyl | MP = 231–234 |
| 129 | 4-CHO—C₆H₅ | O | CH₃ | cyclohexyl | SIMS-NBA-G/TG-DMSO: 393 (M + 1), 365, 307, 289, 273, 262, 257, 246, 225 |
| 130 | 4-HO—C₆H₅ | SO | CH₃ | cyclohexyl | Cl(CH₄): (M + 1) 413, 397, 271, 229, 167 |
| 131 | 3,4-(CH₃O)₂C₆H₄ | SO | CH₃ | cyclohexyl | Cl(Isobutane): (M + 1) 457, 441, |
| 132 | 3-phenyl-2-propynyl | O | CH₃ | cyclohexyl | MP = 191–194 (Dimaleate) |
| 133 | 3-phenyl-2-propenyl | O | CH₃ | cyclohexyl | MP = 145–148 (HCl) |
| 134 | 2-butynyl | O | CH₃ | cyclohexyl | MP = 190–192 (dimaleate) |
| 135 | 4-CH₃O—C₆H₄ | SO₂ | CN | cyclohexyl | SIMS-NBA-G/TG DMSO 454: (M + 1), 427, 399, 346, 299, 274, 257, 238, 215 |
| 136 | 2-pyrimidinyl | SO₂ | CH₃ | cyclohexyl | MP = 194–195 (dimaleate) |
| 137 | 2-pyrimidinyl | SO | CH₃ | cyclohexyl | MP = 165–167 (dimaleate) |
| 138 | 3-pyridyl | SO | CH₃ | cyclohexyl | MP = 123–125 |
| 139 | 3-pyridyl | SO₂ | CH₃ | cyclohexyl | MP = 142–145 |
| 140 | 3-CH₃O—C₆H₄ | O | CH₃ | cyclohexyl | SIMS-NBA-G/TG-DMSO: 395.4 (M + 1), 258, 238, 227, |
| 142 | 4-CH₃O—C₆H₄ | C=NOH ISO 1 | CH₃ | cyclohexyl | EI: (M + 1) 421, 405, 378, 265, 239, |
| 143 | 4-CH₃O—C₆H₄ | C=NOH ISO 2 | CH₃ | cyclohexyl | EI: (M + 1) 421, 405, 377, 265, 254 |
| 144 | 4-CH₃O—C₆H₄ | S | CN | cyclohexyl | SIMS-NBA-G/TG-DMSO: 422 (M + 1), 395, 300, 273, 257, 254, 238 |
| 145 | 4-CH₃O—C₆H₄ | SO | CN | cyclohexyl | Cl(CH₄): 438.2 (M + 1), 411.3, 331, 254.2 |
| 146 | benzyl | C≡C | CH₃ | cyclohexyl | MP = 180–183 (dimaleate) |
| 147 | 1-Me-1-propynyl | O | CH₃ | cyclohexyl | MP = 174–176 (dimaleate) |
| 148 | 4-CH₃O—C₆H₄ | C=NOCH₃ | CH₃ | cyclohexyl | Cl(Isobutane): (M + 1) 436, 404, |
| 150 | 2-(CH₃O)C₆H₄ | CHOH | CH₃ | cyclohexyl | EI: (M + 1) 408, 393, 282, 241, 167 |
| 151 | 2-thienyl | C(CH₃)(OH) | CH₃ | cyclohexyl | MP = 147–149 |

-continued

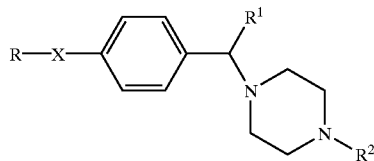

| # | R | X | R¹ | R² | Mass Spectrum or MP |
|---|---|---|----|----|---------------------|
| 152 | 4(CF$_3$O)C$_6$H$_4$ | SO$_2$ | CH$_3$ | cyclohexyl | SIMS-NBA-G/TG-DMSO: 497 (M + 1), 481, 413, 329, 257, 238 |
| 153 | 2(CH$_3$O)C$_6$H$_4$ | CO | CH$_3$ | cyclohexyl | FAB(+ve)-HMR: (M + 1) 407, 397, 329, 307, 260, 237, |
| 154 | CH$_3$COOC$_6$H$_4$ | S | CH$_3$ | cyclohexyl | EI: (M + 1) 438, 395, 298, 271, 229, 167, |
| 155 | 4-CH$_3$SO$_2$—C$_6$H$_4$ | SO$_2$ | CH$_3$ | cyclohexyl | FAB(+ve)-HMR: (M + 1) 491, 475, 391, 365, 273, 257 |
| 156 | C$_6$H$_5$ | SO iso A | CH$_3$ | cyclohexyl | Cl(CH$_4$): 397 (M + 1), 382, 213, 167 |
| 158 | C$_6$H$_5$ | SO iso B | CH$_3$ | cyclohexyl | Cl(CH$_4$): 397 (M + 1), 382, 213, 167 |
| 159 | 2-pentynyl | O | CH$_3$ | cyclohexyl | 191–193 (dimaleate) |
| 160 | 2-thienyl | C=CH$_2$ | CH$_3$ | cyclohexyl | MP = 173–176 (dimaleate) |
| 161 | C$_6$H$_5$ | O | CH$_3$ | (CH$_2$)$_2$OCOC(Me)$_2$ n-C$_3$H$_7$ | Cl(CH$_4$): 439 (M + 1) |
| 162 | 3-butenoyl | NH | CH$_3$ | cyclohexyl | MP = 155–156 |
| 163 | 4(CH$_3$O)C$_6$H$_4$ | CH$_2$ | CH$_3$ | cyclohexyl | Cl(Isobutane): 393 (M + 1), 379, 285, 225, 169 |
| 164 | 3-(3,4-methylenedioxy-phenyl)-2-propenoyl | NH | CH$_3$ | cyclohexyl | SIMS-NBA-G/TG-DMSO: 462 (M + 1), 294, 174, 169, 120 |
| 165 | trifluoroacetyl | NH | CH$_3$ | cyclohexyl | MP = 127–130 |
| 166 | CH$_3$ | C=N—O-2-pyrimidyl | CH$_3$ | cyclohexyl | MP = 173–174 (dimaleate) |
| 167 | 4(CH$_3$S)C$_6$H$_4$ | S | CH$_3$ | cyclohexyl | Cl(CH$_4$): (M + 1) 427, 303, 259, 195, 167, |
| 168 | 4(CH$_3$)C$_6$H$_4$ | SO$_2$ | CH$_3$ | (CH$_2$)$_3$N(Et)COC(Me)$_2$ n-C$_3$H$_7$ | Cl(CH$_4$): 514 (M + 1) |
| 169 | 4(CH$_3$O)C$_6$H$_4$ | SO IsoA | CN | cyclohexyl | SIMS-NBA-G/TG-DMSO: 438 (M + 1), 411, 395, 331, 254, 246, 214 |
| 170 | 4-CH$_3$SO$_2$—C$_6$H$_4$ | SO | CH$_3$ | cyclohexyl | Cl(Isobutane): (M+1) 475, 459 |
| 171 | 4-CH$_3$SO—C$_6$H$_4$ | SO | CH$_3$ | cyclohexyl | FAB(+ve)-HMR: (M + 1) 458, 443, 365, 307, 273, 257 |
| 172 | p-toluenesulfonyl | NH | CH$_3$ | cyclohexyl | EI: 441, 301, 273, 167, 118 |
| 173 | methanesulfonyl | NH | CH$_3$ | cyclohexyl | Cl(CH$_4$): 399 (M + 1), 260, 169 |
| 174 | 2-propynyl | NH | CH$_3$ | cyclohexyl | Cl(CH$_4$): 326 (M + 1), 195, 158 |
| 175 | 2-pyrimidinyl | S | CN | cyclohexyl | Cl(CH$_4$): 394 (M + 1), 367, 257, 217, 167. |
| 176 | 4-Me-1-piperazinyl | SO$_2$ | CH$_3$ | cyclohexyl | Cl(CH$_4$): 435 (M + 1), 269, 217, 183, 170, 167. |
| 177 | 4(CH$_3$O)C$_6$H$_4$ | SO Iso B | CN Iso B | cyclohexyl | SIMS-NBA-G/TG-DMSO: 438 (M + 1), 411, 395, 331, 254, 246, 214 |
| 178 | C$_6$H$_4$ | SO ISO B | CN | cyclohexyl | Cl(Isobutane): (M + 1) 408, 381, 233, 169 |
| 179 | 2-pyrimidinyl | SO | CN | cyclohexyl | SIMS-NBA-G/TG-DMSO) 410 (M + 1), 383, 331, 307 |
| 180 | 1-piperidyl | SO$_2$ | CH$_3$ | cyclohexyl | Cl(Isobutane): 420 (M + 1), 376, 188, 167, 140, 125, 112, 85 |
| 181 | N-morpholino | SO$_2$ | CH$_3$ | cyclohexyl | Cl(Isobutane): 372, (m + 1) 370, 285, 249, 204, 191, 170, 167, 119, 100, 88 |
| 182 | 2-thiazolyl | S | CH$_3$ | cyclohexyl | 178–180 (dimaleate) |
| 183 | 2-thiazolyl | SO | CH$_3$ | cyclohexyl | MP = 179–180 (dimaleate) |
| 184 | 6-Cl-3-pyridazinyl | S | CH$_3$ | cyclohexyl | MP = 123–125 |
| 185 | 6-Cl-3-pyridazinyl | SO$_2$ | CH$_3$ | cyclohexyl | MP = 154–156 |
| 186 | 6-Cl-3-pyridazinyl | SO | CH$_3$ | cyclohexyl | MP = 135–137 |
| 187 | 4-(CH$_3$SO)C$_6$H$_4$ | S | CH$_3$ | cyclohexyl | FAB(+ve)-HMR: (M + 1) 433, 427, 275, 259, 169, |
| 188 | t-BOCNH(CH$_2$)$_7$CO | NH | CH$_3$ | cyclohexyl | SIMS-NBA-G/TG-DMSO: 529 (M + 1), 261 |
| 189 | 4(CH$_3$O)C$_6$H$_4$ | S | CH$_2$NH$_2$ | cyclohexyl | Cl(Isobutane): (M + 1) 426, 395, |
| 190 | propadienyl | S | CH$_3$ | cyclohexyl | MP = 175–177 (dimaleate) |
| 191 | propadienyl | SO$_2$ | CH$_3$ | cyclohexyl | MP = 143–145 (dimaleate) |
| 192 | propadienyl | SO | CH$_3$ | cyclohexyl | MP = 159–161 (dimaleate) |
| 193 | 2-propynyl | SO | CH$_3$ | cyclohexyl | MP = 153–156 (dimaleate) |
| 194 | 1-propynyl | S | CH$_3$ | cyclohexyl | MP = 180–183 (dimaleate) |
| 195 | 2-pyrimidinyl | O | C$_6$H$_5$ | cyclohexyl | SIMS-NBA-G/TG-DMSO: 429 (M + 1), 308, 261 |
| 196 | propadienyl | O | CH$_3$ | cyclohexyl | MP = 149–152 (dimaleate) |
| 197 | 4(CH$_3$O)C$_6$H$_4$ | SO Isomer A | CN Isomer B | cyclohexyl | SIMS-NBA-G/TG-DMSO: 438 (M + 1), 411, 395, 331, 254, 246, 214 |
| 198 | 4(CH$_3$O)C$_6$H$_4$ | SO Isomer A | CH$_3$ | cyclohexyl | SIMS-NBA-G/TG-DMSO: 427 (M + 1), 343 |

-continued

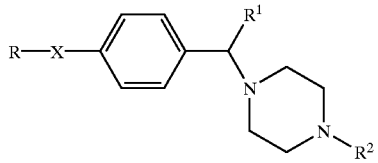

| # | R | X | R¹ | R² | Mass Spectrum or MP |
|---|---|---|----|----|----|
| 200 | 4(CH$_3$O)C$_6$H$_4$ | SO iso B | CN iso A | cyclohexyl | SIMS-NBA-G/TG-DMSO: 438 (M + 1), 411, 395, 331, 254, 246, 214 |
| 201 | C$_6$H$_5$ | O | H | cyclohexyl | Cl(CH$_4$): 351 (M + 1) |
| 202 | C$_6$H$_5$ | O | CN | cyclohexyl | SIMS-NBA-G/TG-DMSO: 375 (M + 1) |
| 203 | 6-(MeNH)-3-pyridazinyl | SO$_2$ | CH$_3$ | cyclohexyl | MP = 177–179 |
| 204 | 6-(MeNH)-3-pyridazinyl | SO | CH$_3$ | cyclohexyl | MP = 113–135 |
| 205 | 2-propynyl | S | CH$_3$ | cyclohexyl | 170–173 (dimaleate) |
| 207 | 4-(CH$_3$O)C$_6$H$_4$ | S | H | cyclohexyl | Cl(Isobutane): (M + 1) 397, |
| 208 | 2-propynyl | NMe | CH$_3$ | cyclohexyl | MP = 73–76 |
| 209 | 2-propynyl | O | CN | cyclohexyl | MP = 128–130 (maleate) |
| 210 | 6-(MeO)-3-pyridazinyl | SO$_2$ | CH$_3$ | cyclohexyl | MP = 165–167 (dimaleate) |
| 211 | 4(CH$_3$O)C$_6$H$_4$ | SO iso A | CN iso A) | cyclohexyl | SIMS-NBA-G/TG-DMSO: 438 (M + 1), 411, 395, 331, 254, 246, 214 |
| 212 | 2-pyrimidinyl | O | cyclohexyl | cyclohexyl | Cl(Isobutane): 435 (M + 1), 351 |
| 213 | 2-pyrimidinyl | O | CN | cyclohexyl | FAB-NBA-G/TG-DMSO: 378 (M + 1), 351 |
| 214 | 4(CH$_3$O)C$_6$H$_4$ | SO$_2$ | CO$_2$CH$_3$ | cyclohexyl | FAB-NBA-G/TG-DMSO: (m + 1) 487, 455, 429, 391, 232 |
| 215 | C$_6$H$_5$ | O | CN | cyclohexyl | Cl(CH$_4$): 376 (M + 1), 349 |
| 216 | 4-HO—C$_6$H$_4$ | SO | CN | cyclohexyl | SIMS-G/TG-DMSO-30% TFA: (M + 1) 424, 408, 397, 381 |
| 217 | 4-(CH$_3$O)C$_6$H$_4$ | SO$_2$ | cyclohexyl | cyclohexyl | EI: 510, 427 |
| 218 | 4-(CH$_3$O)C$_6$H$_4$ | SO | cyclohexyl | cyclohexyl | EI: 494, 411 |
| 219 | 4-(CH$_3$O)C$_6$H$_4$ | S | cyclohexyl | cyclohexyl | EI: 478, 395, 328, 245, 229 |
| 220 | 4-(CH$_3$O)C$_6$H$_4$ | SO$_2$ | CONH$_2$ | cyclohexyl | SIMS-NBA-G/TG-DMSO (M + 1) 472, 456, 427, 345, 232 |
| 221 | 4-(CH$_3$O)C$_6$H$_4$ | SO | C(NH$_2$)=NOH | cyclohexyl | FAB-NBA-G/TG-DMSO: (m + 1) 471, 411, 391, 293, 257, 232, |
| 222 | 4-(CH$_3$O)C$_6$H$_4$ | SO | CONH$_2$ | cyclohexyl | FAB-NBA-G/TG-DMSO: 456 (M + 1), 411, 349, 272 |
| 223 | 1-propynyl | S | CN | cyclohexyl | MP = 173–175 (maleate) |
| 224 | 4-(CH$_3$O)C$_6$H$_4$ | SO | CO$_2$CH$_3$ | cyclohexyl | FAB-NBA-G/TG-DMSO: 471 (M + 1), 455, 411, 364, 287, 273 |
| 225 | cyclopropylmethyl | O | CH$_3$ | cyclohexyl | MP = 197–198 (dimaleate) |
| 226 | 2-propynyl | S | CN | cyclohexyl | 123–125 (maleate) |
| 227 (−) | 2-pyrimidinyl | O | cyclohexyl | cyclohexyl | Cl(CH$_4$): 435 (M + 1), 267 |
| 228 (+) | 2-pyrimidinyl | O | cyclohexyl | cyclohexyl | Cl(CH$_4$): 435 (M + 1), 267 |
| 229 | 1-propynyl | S | cyclohexyl | cyclohexyl | MP = 159–162 (dimaleate) |
| 230 | 2-butynyl | O | CN | cyclohexyl | MP = 137–140 (maleate) |
| 231 | 2-pyrimidinyl | O | 1-Me-4-piperidynyl | cyclohexyl | EI: 449, 351, 282, 185. |
| 232 | 2-pyrimidinyl | O | i-Pr | cyclohexyl | SIMS-NBA-G/TG-DMSO: 395 (M + 1), 227 |
| 233 | 4(CH$_3$O)C$_6$H$_4$ | S | CO$_2$CH$_3$ | cyclohexyl | SIMS-NBA-G/TG-DMSO: 455 (M + 1), 395, 287, 246 |
| 234 | 4(CH$_3$O)C$_6$H$_4$ | SO | 5-tetrazolyl | cyclohexyl | SIMS-NBA-G/TG-DMSO: (M + 1), 481, 465, 456, 411, 395 |
| 235 | 2-pyrimidinyl | O | cyclopentyl | cyclohexyl | M.P. = 165–8 (HCl) |
| 236 | 4(CH$_3$O)C$_6$H$_4$ | SO | 2-Me-5-tetrazolyl | cyclohexyl | FAB-NBA-G/TG-DMSO: 495 (M + 1), 471, 438, 411, 283, 273, 246, 232 |
| 237 | 4(CH$_3$O)C$_6$H$_4$ | S | allyl | cyclohexyl | FAB-NBA-G/TG-DMSO: 437 (M + 1), 395, 313, 264, 246, 242 |
| 238 | 2-propynyl | O | CN | cyclohexyl | M.P. = 115–117 |
| 239 | 2-propynyl | O | CH$_3$ | cyclohexyl | M.P. = 178–180 (Dimaleate) |
| 240 | 4(CH$_3$O)C$_6$H$_4$ | SO | 3-TMS-4-(1,2,3)-tri-azolyl | cyclohexyl | FAB-NBA-G/TG-DMSO: 552 (M + 1), 536, 368, 356, 214 |
| 241 | 2-pyrimidinyl | O | allyl | cyclohexyl | M.P. = 225–7 (HCL) |
| 199 | 4-(CH$_3$)—C$_6$H$_4$ | SO | CON(Me)2 | cyclohexyl | FAB-NBA-G/TG-DMSO: 468 (M + 1), 431, 395, 304, 300 |

Compounds having the formula

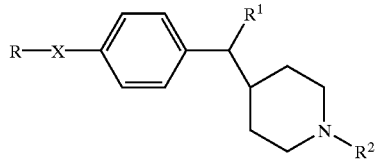

| # | R | X | R¹ | R² | Mass Spectrum or MP |
|---|---|---|---|---|---|
| 242 | $C_6H_5$ | $SO_2$ | $CH_3$ | $CH_3$ | EI: 343 (M), 125 |
| 243 | 2-pyrimidinyl | O | CN | chex | SIMS-NBA-G/TG-DMSO: 377 (M + 1) |
| 141 | $C_6H_5$ | O | H | chex | FAB-NBA-G/TG-DMSO: 350 (M + 1) |
| 149 | 3-Cl—$C_6H_5$ | $SO_2$ | =$CH_2$ | $CH_3$ | FAB-NBA-G/TG-DMSO: 376 (M + 1) |

Compounds having the formula

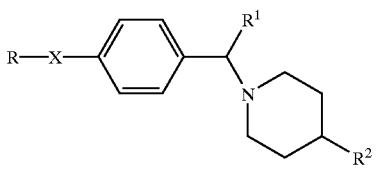

| # | R | X | R¹ | R² | Mass Spectrum or MP |
|---|---|---|---|---|---|
| 244 | $C_6H_5$ | $SO_2$ | i-Pr | $N(CH_3)_2$ | FAB-NBA-G/TG-DMSO: (M + 1) 401, 356, 312, 273 |
| 245 | $C_6H_5$ | $SO_2$ | $C_6H_5$ | 1-piperidyl | Cl($CH_4$): (M + 1) 475, 307 |
| 246 | 4-$CH_3$—$C_6H_4$ | $SO_2$ | i-Pr | 1-piperidyl | |
| 247 | 2-pyrimidinyl | O | $CH_3$ | $CH_3$ | Cl($CH_4$): 298 (M + 1), 282, 199, 126. Cl(City) |
| 248 | 4-$CH_3$—$C_6H_4$ | $SO_2$ | $CH_3$ | $CH_3$ | EI: 358 (M + 1), 342 |
| 249 | 4-$CH_3$—$C_6H_4$ | $SO_2$ | $CH_3$ | $CO_2Et$ | SIMS-NBA-G/TG-DMSO: 416 (M + 1) |
| 250 | 4-$CH_3$—$C_6H_4$ | $SO_2$ | $CH_3$ | benzyl | SIMS-NBA-G/TG-DMSO: 434 (M + 1) |
| 251 | 2-pyrimidinyl | O | $CH_3$ | 1-piperidyl | Cl($CH_4$): 367 (M + 1) 281, 199, 167 |
| 252 | 2-pyrimidinyl | O | $CH_3$ | chex | SIMS-NBA-G/TG-DMSO: 366 (M + 1), 350 |
| 253 | $C_6H_5$ | $SO_2$ | H | $(CH_2)_3N(Et)COC(Me)_2$ n-$C_3H_7$ | SIMS-NBA-G/TG-DMSO: 513 (M + 1) |
| 254 | $C_6H_5$ | $SO_2$ | $CH_3$ | $CH_3$ | Cl($CH_4$): 344 (M + 1) |
| 255 | $C_6H_5$ | $SO_2$ | $CH_3$ | chex | Cl($CH_4$): 412 (M + 1) |
| 256 | $C_6H_5$ | O | $CH_3$ | $CH_3$ | Cl($CH_4$): 296 (M + 1) |
| 82 | 4-$CH_3$—$C_6H_6$ | $SO_2$ | $CH_3$ | chex | Cl($CH_4$): 426 (M + 1) 342, 270, 166 |

Compounds having the formula

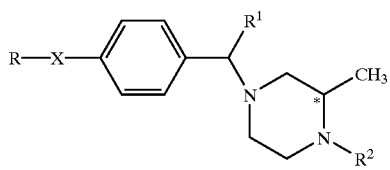

| # | R | X | R¹ | R² | * | Mass Spectrum or MP |
|---|---|---|---|---|---|---|
| 257 | $C_6H_5$ | $SO_2$ | H | chex | | SIMS-G/TG-DMSO: 413 (M + 1) |
| 258 | $C_6H_5$ | $SO_2$ | H | chex | Isomer A | SIMS-NBA-G/TG-DMSO: 413 (M + 1) |
| 259 | $C_6H_5$ | $SO_2$ | H | chex | Isomer B | Cl($CH_4$): 413 (M + 1) |
| 260 | 3-Cl—$C_6H_4$ | $SO_2$ | $CH_3$ | chex | Isomer B | SIMS-NBA-G/TG-DMSO: 463, 461 (M + 1) |
| 261 | 2-pyrimidinyl | O | $CH_3$ | chex | Isomer A | Cl($CH_4$): 381 (M + 1), 199. |
| 262 | 2-pyrimidinyl | O | $CH_3$ | chex | Isomer B | SIMS-NBA-G/TG-DMSO: 381 (M + 1) |
| 263 iso A | 4($CH_3O)C_6H_4$ | SO | CN | chex | Isomer A | SIMS-NBA-G/TG-DMSO: 452 (M + 1) |
| 206 IsoB | 4-$CH_3O$—$C_6H_4$ | SO | CN | chex | Isomer B | Cl(Isobutane): 452 (M + 1), 425 |

Compounds having the formula

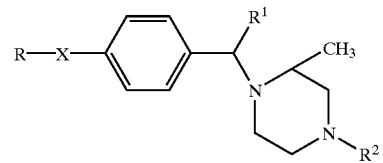

| # | R | X | R¹ | R² | * | Mass Spectrum or MP = |
|---|---|---|---|---|---|---|
| 265 | $C_6H_5$ | $SO_2$ | H | chex | | EI: 412, 369, 181, 126. |
| 266 | $C_6H_5$ | $SO_2$ | H | chex | Isomer A | SIMS-NBA-G/TG-DMSO: 413 (M + 1) |
| 267 | $C_6H_5$ | $SO_2$ | H | chex | Isomer B | Cl($CH_4$): 413 (M + 1) |
| 268 | $C_6H_5$ | $SO_2$ | $CH_3$ | chex | | Cl($CH_4$): 427 (M + 1) |
| 269 | 2-pyrimidinyl | O | $CH_3$ | chex | | SIMS-NBA-G/TG-DMSO: 381 (M + 1), 199 |
| 270 | 2-pyrimidinyl | O | 1-Me-4-piperidinyl | chex | | Cl($CH_4$): 464 (M + 1), 462, 282 |
| 271 | 2-pyrimidinyl | O | i-Pr | chex | | SIMS-NBA-G/TG-DMSO: 409 (M + 1), 227 |
| 272 | 2-pyrimidinyl | O | H | chex | | Cl($CH_4$): 367 (M + 1) |
| 273 | 2-pyrimidinyl | O | n-hexyl | chex | | SIMS-NBA-G/TG-DMSO: 451 (M + 1), 269 |
| 274 Iso.A | 2-pyrimidinyl | O | chex | chex | | Cl($CH_4$): 449 (M + 1), 365, 267 |
| 275 Iso.B | 2-pyrimidinyl | O | chex | chex | | Cl($CH_4$): 449 (M + 1), 365, 267 |
| 157 | $C_6H_5$ | $SO_2$ | H | 2-cyclohexenyl | | SIMS-NBA-G/TG-DMSO: 411 (M + 1) |

Compounds having the formula

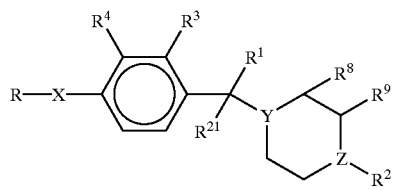

| # | Mass Spectrum or MP |
|---|---|

280 R is 4-$CH_3$—$C_6H_4$; X is $SO_2$;
$R^1$ is $CH_3$; $R^2$ is

[structure: γ-butyrolactone fragment]

$R^3$, $R^4$, $R^8$, $R^9$, and $R^{21}$ are H; Y and Z are N
mass spec Cl($CH_4$): 429 (M + 1)

281 R is 4-$CH_3$—$C_6H_4$; X is $SO_2$; $R^1$ is $CH_3$; $R^2$ is chex; $R^3$ is $OCH_3$; $R^4$, $R^8$, $R^9$, and $R^{21}$ are H; and Y and Z are N
mass spec Cl($CH_4$): 457 (M + 1)

282 R is 4-$CH_3$—$C_6H_4$; X is $SO_2$; $R^1$ is $CH_3$; $R^2$ is chex; $R^3$ is H; $R^4$ is F; $R^8$, $R^9$, and $R^{21}$ are H; Y and Z are N
mass spec Cl($CH_4$): (M + 1) 445, 289, 277, 195, 167

283 R is $C_6H_5$; X is $SO_2$; $R^1$ is $CH_3$; $R^2$ is chex; $R^3$ is Cl; $R^4$, $R^8$, $R^9$, and $R^{21}$ are H; Y and Z are N;
mass spec Cl($CH_4$): 449, 447, (M + 1)

284 R is 4-$CH_3$—$C_6H_4$; X is $SO_2$; $R^1$ is $CH_3$; $R^2$, $R^3$ and $R^4$ are H; $R^9$ is $CH_2OH$; $R^4$ and $R^{21}$ are H; Y is N; Z is $CH_2$;
mass spectrum Cl($CH_4$); 374 (M + 1), 261.

285 R is 4-($CH_3O$)$C_6H_4$; X is

[structure: 1,3-dithietane fragment]

$R^1$ is $CH_3$; $R^2$ is chex; $R^3$, $R^4$, $R^8$, $R^9$, and $R^{21}$ are H, Y and Z are N
mass spectrum EI: (M + 1) 482, 467, 439, 343, 255, 211, 167

-continued

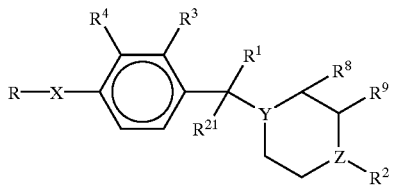

| # | Mass Spectrum or MP |
|---|---|
| 286 | R is $CH_3$; 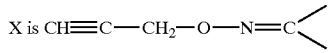 $R^1$ is $CH_3$; $R^2$ is chex; $R^3$, $R^4$, $R^8$, $R^9$ and $R^{21}$ are H; Y and Z are N MP = 173–175 dimaleate |
| 287 | R is $C_6H_5$; X is $SO_2$; $R^1$ is H, $R^2$ is chex; $R^3$ is Cl; $R^4$ and $R^5$ are H; $R^9$ is (R)—$CH_3$, $R^{21}$ is H; Y and Z are N; mass spec Cl($CH_4$): 447 (M + 1) |
| 288 | R is 4-($CH_3O$)—$C_6H_4$; X is SO; $R^1$ is CN; $R^2$ is chex; $R^3$, $R^4$, $R^8$, and $R^9$ are H; $R^{21}$ is $CH_2CO_2CH_3$; Y and Z are N; mass spec SIMS-NBA-G/TG-DMSO) 510.2 (M + 1) 483.2, 307.1, 273.1, 246.1, 214 |
| 289 | R is 4-($CH_3O$)—$C_6H_4$; X is SO; $R^1$ is CN; $R^2$ is chex; $R^3$, $R^4$, $R^8$, and $R^9$ are H; $R^{21}$ is $CH_3$; Y and Z are N mass spec SIMS-NBA-G/TG-DMSO: 452.2 (M + 1), 425.2, 293.1, 268.1, 257.1 |
| 290 | R is 4-($CH_3O$)—$C_6H_4$; X is SO; $R^1$ is CN; $R^2$ is chex; $R^3$, $R^4$, $R^8$, and $R^9$ are H; $R^{21}$ is $CO_2Me$; Y and Z are N mass spec FAB-NBA-G/TG-DMSO: 496 (M + 1), 480, 469, 454, 389, 312 |
| 291 | R is 2-pyrimidinyl; X is O; $R^1$ is $CH_3$; $R^2$ is chex; $R^3$ and $R^4$ are H; $R^8$ is (S)—$CH_3$; $R^9$ and $R^{21}$ are H; Y and Z are N; mass spec FAB-NBA-G/TG-DMSO: 381 (M + 1), 199. |
| 292 | R is 2-pyrimidinyl; X is O; $R^1$ is H; $R^2$ is chex; $R^3$ and $R^4$ are H; $R^8$ is (S)—$CH_3$; $R^9$ and $R^{21}$ are H; Y and Z are N; mass spec FAB-NBA-G/TG-DMSO: 267 (M + 1) |
| 293 | R is 2-pyrimidinyl; X is O; $R^1$ is H; $R^2$ is chex; $R^3$ and $R^4$ are H; $R^8$ is (R)—$CH_3$; $R^9$ and $R^{21}$ are H; Y and Z are N; mass spec FAB-NBA-G/TG-DMSO: 367 (M + 1) |
| 294 | R is 2-pyrimidinyl; X is O; $R^1$ is $CH_3$; $R^2$ is chex; $R^3$ and $R^4$ are H; $R^8$ is (R)—$CH_3$; $R^9$ and $R^{21}$ are H; Y and Z are N; M.P. = 170–173 (HCL) |
| 295 | R is 4-($CH_3O$)—$C_6H_4$; X is SO; $R^1$ is CN; $R^2$ is chex; $R^3$, $R^4$, $R^8$ and $R^9$ are H; $R^{21}$ is CN; Y and Z are N; mass spec FAB-NBA-G/TG-DMSO: 463 (M + 1), 436, 356, 307, 273 |
| 296 | R is 4($CH_3O$)—$C_6H_4$; X is SO; $R^1$ is $CH_3$; $R^2$ is chex; $R^3$, $R^4$, $R^8$, and $R^9$ are H; $R^{21}$ is $CO_2Me$; Y and Z are N; mass spec FAB-NBA-G/TG-DMSO: 485 (M + 1), 471, 425, 381, 365, 338, 320 |
| 297 | R is 2-propynyl; X is O; $R^1$ is $CH_3$; $R^2$ is chex; $R^4$ is Cl; $R^3$, $R^8$, $R^9$, and $R^{21}$ are H; Y and Z are N M.P. = 172–174 (dimaleate) |
| 298 | R is 4-($CH_3O$)—$C_6H_4$; X is SO; $R^1$ is CN; $R^2$ is chex; $R^3$, $R^4$, $R^8$ and $R^9$ are H; $R^{21}$ is allyl; Y and Z are N; mass spec FAB-NBA-G/TG-DMSO: 478 (M + 1), 451, 354, 294, 246 |
| 299 | R is 2-propynyl; X is O; $R^1$ is CN; $R^2$ is chex; $R^4$ is Cl; $R^3$, $R^8$, $R^9$ are $R^{21}$ are H; Y and Z are N M.P. = 132–134 (maleate) |
| 300 | R is 4($CH_3O$)—$C_6H_4$; X is SO; $R^1$ and $R^{21}$ together form =$CH_2$; $R^2$ is cyclohexxyl, y is CH, Z is N, $R^3$, $R^4$, $R^8$ and $R^9$ are H - sulfoxide isomer A |
| 301 | R is 4($CH_3O$)—$C_6H_4$; X is SO; $R^1$ and $R^{21}$ together form =$CH_2$; $R^2$ is cyclohexxyl, y is CH, Z is N, $R^3$, $R^4$, $R^8$ and $R^9$ are H - sulfoxide isomer B; mp = 141–142 |
| 302 | R is 4($CH_3O$)—$C_6H_4$; X is S; $R^1$ and $R^{21}$ together form =$CH_2$; $R^2$ is cyclohexyl, Y is CH, Z is N, $R^3$, $R^4$, $R^8$ and $R^9$ are H; mp = 227–230 (HCl) |
| 303 | $R^1$ is $C_6H_5$; X is O; $R^1$ and $R^{21}$ together form  ; Y and Z are N; $R^2$ is cyclohexyl; $R^3$, $R^4$, $R^8$ and $R^9$ are H; mp = 137–139 |
| 304 | R is 4($CH_3O$)—$C_6H_4$; X is SO; $R^1$ and $R^{21}$ together form =$CH_2$; $R^2$ is cyclohexyl, y is CH, Z is N, $R^3$, $R^4$, $R^8$ and $R^9$ are H - racemic mixture; mp = 122 |
| 305 | R is 4($H_3CO$)—$C_6H_4$; X is SO; $R^1$ and $R^{21}$ together form =O; $R^2$ is cyclohexyl; Y is CH; Z is N; $R^3$, $R^4$, $R^8$ and $R^9$ are H. |
| 306 | R is $C_6H_5$, X is O, $R^1$ and $R^{21}$ together form  , and Y and Z are N, $R^3$, $R^4$, $R^8$ and $R^9$ are H; mp = 144–146 (dimaleate) |

In like manner compounds 600 to 804 from the previous table were produced with the following physical data:

| Compound Number | Melting Point or Mass Spectral Data |
|---|---|
| 600 | FAB (NBA-G/TG-DMSO): 435 (M + 1), 391, 338, 324 |
| 601 | mp = 164–167 |
| 602 | MS CALC'D 461.2030 FOUND 461.2040 |
| 603 | MS CALC'D 425 FOUND 425 |
| 604 | FAB (NBA-G/TG-DMSO): 471 (M + 1), 455, 411, 364, 287 |
| 605 | mp = 64–68 |
| 606 | mp = 194–195 |
| 607 | Mass Spec CI (ISOB): 408 (M + 1), 381, 365, 231, 169 |
| 608 | MS CALC'D 453 FOUND 453 |
| 609 | Mass Spec SIMS (NBA-G/TG-DMSO): 452 (M + 1), 425, 409, 293, 232 |
| 610 | Mass Spec FAB (NBA-G/TG-DMSO): 544 (M + 1), 543, 516, 232 |
| 611 | MS CALC'D 467 FOUND 467 |
| 612 | mp = 142–145 |
| 613 | Mass Spec CI: 452 (M + 1) |
| 614 | MS CALC'D 437 FOUND 437 |
| 615 | Mass Spec SIMS (NBA-G/TG-DMSO): 452 (M + 1), 425, 409, 293, 232 |
| 616 | MS CALC'D 389 FOUND 390 |
| 617 | Mass Spec FAB (NBA-G/TG-DMSO): 560 (M + 1), 559, 532, 433, 363 |
| 618 | mp = 143–145 |
| 619 | |
| 620 | mp = 123–124 |
| 621 | Mass Spec FAB (NBA-G/TG-DMSO): 495 (M + 1), 411, 299, 283 |
| 622 | mp = 205 |
| 623 | mp = 212 |
| 624 | Mass Spec FAB (NBA-G/TG-DMSO): 544 (M + 1), 543, 516 |
| 625 | mp = 132–134 |
| 626 | Mass Spec FAB (NBA-G/TG-DMSO): 514 (M + 1), 513, 486, 240 |
| 627 | Mass Spec FAB (SIMS9CAL): 530 (M + 1), 425, 398 |
| 628 | mp = 141–145 |
| 629 | mp = 151–154 |
| 630 | Mass Spec FAB (NBA-G/TG-DMSO): 560 (M + 1), 559, 532 |
| 631 | Mass Spec FAB (SIMS4CAL): 515 (M + 1), 514, 487, 307, 289, 238 |
| 632 | mp = 121–124 MS CALC'D 410 FOUND 410 |
| 633 | MS CALC'D 438.2200 FOUND 438.2215 |
| 634 | Mass Spec CI: 436 (M + 1), 409 |
| 635 | mp = 190 (dec) |
| 636 | MS CALC'D 381 FOUND 382 |
| 637 | mp = 225 |
| 638 | MS CALC'D 441 FOUND 442 |
| 639 | mp = 253–255 |
| 640 | Mass Spec FAB (NBA-G/TG-DMSO): 409 (M + 1), 381 |
| 641 | MS CALC'D 454 FOUND 455 |
| 642 | mp = 245 |
| 643 | mp = 209 |
| 644 | MS CALC'D 419.2698 FOUND 419.2706 |
| 645 | mp = 248–250 |
| 646 | mp = 132–133 MS CALC'D 439 FOUND 439 |
| 647 | MS CALC'D 454 FOUND 455 |
| 648 | mp = 210–211 |
| 649 | mp = 250 |
| 650 | mp = 200–203 |
| 651 | MS CALC'D 380.2048 FOUND 380.2047 |
| 652 | mp = 129–131 MS CALC'D 439 FOUND 439 |
| 653 | mp = 188–189 |
| 654 | MS CALC'D 394.2205 FOUND 394.2199 |
| 655 | MS CALC'D 451.2419 FOUND 451.2404 |
| 656 | mp = 227–230 |
| 657 | MS CALC'D 452 FOUND 452 |
| 658 | mp = 53–55 |
| 659 | MS CALC'D 412.2110 FOUND 412.2111 |
| 660 | MS CALC'D 412.1946 FOUND 412.1950 |
| 661 | HRMS Calcd 455.2368 Found 455.2370 |
| 662 | MS CALC'D 430.1852 FOUND 430.1856 |
| 663 | mp = 159–163 MS CALC'D 439 FOUND 440 |
| 664 | MS CALC'D 471.2318 FOUND 471.2327 |
| 665 | MS CALC'D 381.2001 FOUND 381.2000 |
| 666 | MS CALC'D 410.2154 FOUND 410.2158 |
| 667 | mp = 241–242 |
| 668 | MS CALC'D 470.2367 FOUND 470.2367 |
| 669 | mp = 168–170 MS CALC'D 440 FOUND 441 |
| 670 | MS CALC'D 414.1903 FOUND 414.1899 |
| 671 | mp = 130.5–131.5 |
| 672 | Mass Spec CI (CH4): 481 (M + 1), 465, 445, 357, 297, 249, 167 |
| 673 | MS CALC'D 379.2208 FOUND 379.2210 |
| 674 | MS:calcd for C28H35NO4: 481 found 481.7. |
| 675 | MS CALC'D 395.2157 FOUND 395.2161 |
| 676 | MS:calcd for C29H37NO4: 495; found 494 (M + 1). |
| 677 | mp = 150–151 |
| 678 | Mass Spec CI (CH4): 497 (M + 1), 477, 325, 167 |
| 679 | MS CALC'D 387 FOUND 388 |
| 680 | MS CALC'D 413.1899 FOUND 413.1892 |
| 681 | MS CALC'D 411.2106 FOUND 411.2100 |
| 682 | MS:calcd for C32H37NO2: 499; found 500 (M + 1). |
| 683 | MS CALC'D 381.2001 FOUND 381.1996 |
| 684 | MS CALC'D 478.2028 FOUND 478.2014 |
| 685 | MS:calcd for C29H37NO3: 479; found 480.4 (M + 1). |
| 686 | MS CALC'D 397.1950 FOUND 397.1954 |
| 687 | MS CALC'D 462.2078 FOUND 462.2078 |
| 688 | MS:calcd for C32H37NO3: 515; found 516 (M + 1). |
| 689 | MS CALC'D 413.1899 FOUND 483.1892 |
| 690 | MS CALC'D 379.2208 FOUND 379.2203 |
| 691 | MS CALC'D 437.2263 FOUND 437.2264 |
| 692 | MS CALC'D 395.2157 FOUND 395.2169 |
| 693 | MS CALC'D 442.2052 FOUND 442.2057 |
| 694 | MS CALC'D 442.2052 FOUND 442.2057 |
| 695 | MS CALC'D 456.2572 FOUND 456.2580 |
| 696 | MS CALC'D 391 FOUND 391 |
| 697 | MS CALC'D 397.1950 FOUND 397.1954 |
| 698 | MS CALC'D 516.2572 FOUND 516.2572 |
| 699 | MS CALC'D 410.2154 FOUND 410.2154 |
| 700 | mp = 215–218 |
| 701 | MS CALC'D 456 FOUND 457 |
| 702 | MS CALC'D 437.2263 FOUND 437.2269 |
| 703 | MS CALC'D 411.2106 FOUND 411.2104 |
| 704 | MS CALC'D 426.2103 FOUND 426.2117 |
| 705 | MS CALC'D 440.2623 FOUND 440.2632 |
| 706 | mp = 215–218 |
| 707 | m.p. = 165.0–170.0° C. (•2HCl) |
| 708 | m.p. = 155.0–160.0° C. (•2HCl) |
| 709 | MS CALC'D 470.2001 FOUND 470.2007 |
| 710 | mp = 248–250 |
| 711 | MS:calcd for C30H40N2SO5: 540; found 541 (M + 1). |
| 712 | MS CALC'D 510.2790 FOUND 510.2787 |
| 713 | MS CALC'D 466 FOUND 467 |
| 714 | m.p. = 141.0–142.0° C. (free base) |
| 715 | Mass Spec FAB: 485 (M + 1), 441, 253, 209 |
| 716 | MS CALC'D 428.1896 FOUND 428.1904 |
| 717 | MS:calcd for C25H32N2SO3: 440; found 441.2 (M + 1). |
| 718 | MS CALC'D 420 FOUND 421 |
| 719 | MS CALC'D 514 FOUND 515 |
| 720 | m.p. = 90.0–95.0° C. (free base) |
| 721 | Mass Spec FAB: 485 (M + 1), 391, 273, 232 |
| 722 | MS CALC'D 496.1769 FOUND 496.1765 |
| 723 | MS CALC'D 497.2474 FOUND 497.2460 |
| 724 | MS CALC'D 466 FOUND 467 |
| 725 | MS CALC'D 498 FOUND 499 |
| 726 | mp = 200–210 (dec), Mass Spec MH+ = 433 |
| 727 | mp = 210 (dec) |
| 728 | mp = 220 deg (dec) |
| 729 | MS CALC'D 427.2419 FOUND 427.2427 |
| 730 | |
| 731 | mp = 180 (dec) |
| 732 | mp = 200 (dec), Mass Spec MH+ = 433 |
| 733 | mp = 180 deg (dec) |
| 734 | mp = 215 deg (dec) |
| 735 | MS CALC'D 443.2368 FOUND 443.2367 |
| 736 | mp = 210 deg (dec) |
| 737 | mp = 200 deg (dec) |

-continued

| Compound Number | Melting Point or Mass Spectral Data |
|---|---|
| 738 | mp = 205 deg (dec) |
| 739 | mp = 210 deg (dec) |
| 740 | |
| 741 | mp = 205 deg (dec) |
| 742 | mp = 185 deg (dec) |
| 743 | mp = 120–123 |
| 744 | mp = 125–128 |
| 745 | mp = 130–133 |
| 746 | Mass Spec FAB (NBA-G/TG-DMSO): 480 (M + 1), 479, 452, 311 |
| 747 | mp = 208–211 |
| 748 | MS CALC'D 427 FOUND 428 |
| 749 | mp = 131–134 |
| 750 | 161–163 |
| 751 | FAB MS 648(MH+) |
| 752 | Mass Spec FAB (NBA-G/TG-DMSO): 511 (M + 1), 484 |
| 753 | FAB: 495 (M + 1), 479, 411, 311 |
| 754 | MS CALC'D 439 FOUND 440 |
| 755 | MS CALC'D 440.2259 FOUND 440.2255 |
| 756 | MS CALC'D 470 FOUND 470 |
| 757 | mp = 131–132.5 |
| 758 | MS:calcd for C26H35NSO2; 425; found 426.3 (M + 1). |
| 759 | MS CALC'D 455 FOUND 456 |
| 760 | MS:calcd for C28H36N2SO5; 512; found 513.2 (M + 1). |
| 761 | MS CALC'D 456 FOUND 456 |
| 762 | mp = 165–166 MS CALC'D 437 FOUND 438 |
| 763 | MS:calcd for C28H36N2SO4: 496; found 497.3 (M + 1). |
| 764 | MS:calcd for C26H33NSO2: 423; found 424.3 (M + 1). |
| 765 | MS:calcd for C28H36N2SO3: 480; found 481.6 (M + 1). |
| 766 | MS:calcd for C26H35NSO4: 457; found 458 (M + 1). |
| 767 | MS:calcd for C26H35NSO3: 441; found 442 (M + 1). |
| 768 | mp = 149–150 |
| 769 | MS:calcd for C28H37NSO4: 483; found 484 (M + 1). |
| 770 | MS CALC'D 476.2071 FOUND 476.2066 |
| 771 | MS:calcd for C28H38N2SO5: 514; found 515.3 (M + 1). |
| 772 | mp = 142–143 |
| 773 | mp = 143–144 |
| 774 | MS:calcd for C28H37NSO5: 499; found 500 (M + 1). |
| 775 | MS CALC'D 460 FOUND 460 |
| 776 | MS:calcd for C29H37NSO5: 511; found 512 (M + 1). |
| 777 | MS:calcd for C28H41N3S2O5: 563; found 564.1 (M + 1). |
| 779 | m.p. = 150.0–152.0° C. (•2HCl) |
| 780 | m.p. = 187.0–189.0° C. (•2HCl) |
| 781 | MS:calcd for C25H31NSO4: 441; found 442 (M + 1). |
| 782 | MS:calcd for C25H31NSO2: 409; found 410 (M + 1). |
| 783 | MS:calcd for C28H39N3SO5: 529; found 530.7 (M + 1). |
| 784 | m.p. = 155.0–157.0° C. (•2HCl) |
| 785 | m.p. = 135.0–137.0° C. (•2HCl) |
| 786 | MS calc'd 511.2994 found: 511.3000 |
| 787 | MS:calcd for C25H31NSO3: 425; found 426 (M + 1). |
| 788 | MS:calcd for C28H39N3SO5: 529; found 530.3 (M + 1). |
| 789 | MS:calcd for C28H39N3SO3: 497; found 498.4 (M + 1). |
| 790 | MS:calcd for C28H39N3SO3: 497; found 498.3 (M + 1). |
| 791 | MS:calcd for C29H41N3SO4: 527; found 528.1 (M + 1). |
| 792 | mp = 205–210 |
| 793 | Mass Spec CI: 375 (M + 1) |
| 794 | mp = 150–152 |
| 795 | mp = 224–227 |
| 796 | MS:calcd for C30H43N3SO3: 525; found 526 (M + 1). |
| 797 | MS:calcd for C28H40N4SO4: 528; found 529.1 (M + 1). |
| 798 | Mass Spec CI: 441 (M + 1). |
| 799 | mp = 138–140 |
| 800 | mp = 143–146 |
| 801 | mp = 259 |
| 802 | mp = 120–122 |
| 803 | mp = 215–225 (dec) Mass Spec MH+ = 473 |
| 804 | mp = 195–205 (dec) Mass Spec MH+ = 473 |
| 805 | mp = 228–230 (dec) |

What is claimed:

1. A compound having the structural formula

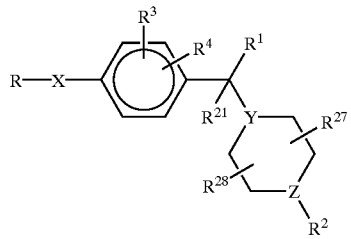

or an isomer or pharmaceutically acceptable salt or solvate thereof, wherein one of Y and Z is N and the other is CH, or C-alkyl;

X is —O—, —S—, —SO— or —SO$_2$—;

R is pyridyl;

$R^1$ and $R^{21}$ are independently selected from the group consisting of alkyl, cyano, H or —OH, (provided $R^1$ and $R^{21}$ are both not —OH and Y is not N); additionally $R^1$ and $R^{21}$ together may form the group =CH$_2$, =CH-alkyl, =O or =C(alkyl)$_2$;

$R^2$ is cycloalkyl;

$R^3$ and $R^4$ are H; and $R^{27}$ and $R^{28}$ are independently selected from the group consisting of H and alkyl.

2. A compound of claim 1 wherein $R^3$ and $R^4$ are H, and either $R^1$ is alkyl or CN and $R^{21}$ is H, or $R^1$ and $R^{21}$ together form =CH$_2$ or =O.

3. A compound of claim 1 wherein Y is CH and Z is N.

4. A compound of claim 1 selected from the group consisting of compounds represented by the formula

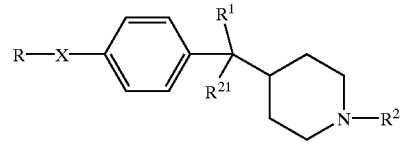

wherein R, X, $R^1$, $R^{21}$ and $R^2$ are as defined in the following table:

| R | X | $R^1$, $R^{21}$ | $R^2$ |
|---|---|---|---|
| pyridyl | —S— | =O | cyclohexyl |
| pyridyl | —S— | =CH$_2$ | cyclohexyl |
| pyridyl | —SO— | =CH$_2$ | cyclohexyl |

-continued
| R | X | R¹, R²¹ | R² |
|---|---|---------|-----|
| 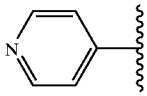 | —SO₂— | =O | 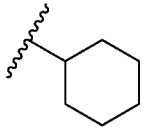 |
| 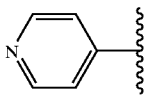 | —SO₂— | =CH₂ | 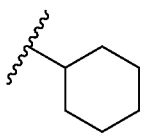 |
| 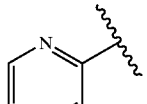 | —S— | =O | 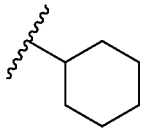 |
| 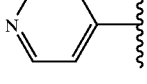 | —SO— | =O | 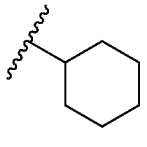 |
| 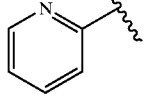 | —SO₂— | =O | 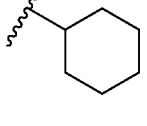 |
-continued
| R | X | R¹, R²¹ | R² |
|---|---|---------|-----|
| 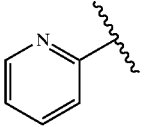 | —S— | =CH₂ | 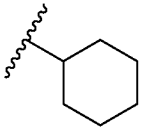 |
| 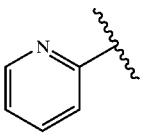 | —SO— | =CH₂ | 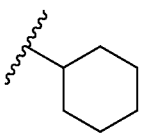 |
| 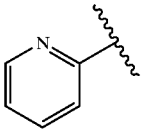 | —SO— | =O | 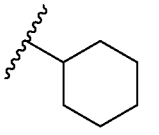 |
| 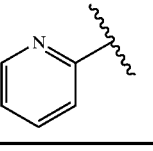 | —SO₂— | =CH₂ | 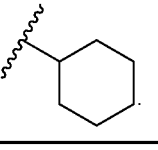 |
5. A pharmaceutical composition which comprises a compound as defined in claim 1 in combination with a pharmaceutically acceptable carrier.
* * * * *